United States Patent
Liu et al.

(10) Patent No.: US 11,661,422 B2
(45) Date of Patent: May 30, 2023

(54) TRICYCLIC UREA COMPOUNDS AS JAK2 V617F INHIBITORS

(71) Applicant: Incyte Corporation, Wilmington, DE (US)

(72) Inventors: Kai Liu, Chadds Ford, PA (US); Brent Douty, Fallowfield, PA (US); Daniel Levy, Philadelphia, PA (US); Liangxing Wu, Wilmington, DE (US); Wenqing Yao, Chadds Ford, PA (US); Eddy W. Yue, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/412,650

(22) Filed: Aug. 26, 2021

(65) Prior Publication Data

US 2022/0064165 A1 Mar. 3, 2022

Related U.S. Application Data

(60) Provisional application No. 63/071,058, filed on Aug. 27, 2020.

(51) Int. Cl.
C07D 471/14 (2006.01)
A61K 31/519 (2006.01)

(52) U.S. Cl.
CPC ........ *C07D 471/14* (2013.01); *C07B 2200/05* (2013.01)

(58) Field of Classification Search
CPC ........................... C07D 471/14; A61K 31/519
USPC .......................................... 544/251; 514/257
See application file for complete search history.

(56) References Cited

U.S. PATENT DOCUMENTS

| | | | |
|---|---|---|---|
| 4,698,341 A | 10/1987 | Satzinger et al. |
| 6,339,099 B1 | 1/2002 | Lam et al. |
| 6,951,865 B2 | 10/2005 | Hibi et al. |
| 7,429,456 B2 | 9/2008 | Vainchenker et al. |
| 7,781,199 B2 | 8/2010 | Vainchenker et al. |
| 7,879,844 B2 | 2/2011 | Inoue et al. |
| 8,163,767 B2 | 4/2012 | Inoue et al. |
| 8,524,867 B2 | 9/2013 | Bernett et al. |
| 8,637,235 B2 | 1/2014 | Vainchenker et al. |
| 8,785,639 B2 | 7/2014 | Wishart et al. |
| 8,852,931 B2 | 10/2014 | Vainchenker et al. |
| 9,233,985 B2 | 1/2016 | Van Zandt et al. |
| 9,321,730 B2 | 4/2016 | Chan et al. |
| 9,493,419 B2 | 11/2016 | Tang et al. |
| 10,065,974 B2 | 9/2018 | Sjogren et al. |
| 10,155,987 B2 | 12/2018 | Sattler et al. |
| 10,287,303 B2 | 4/2019 | Sjogren et al. |
| 10,377,759 B2 | 8/2019 | Yamamoto et al. |
| 2003/0139431 A1 | 7/2003 | Kawakami et al. |
| 2004/0209902 A1 | 10/2004 | Lin et al. |
| 2005/0182060 A1 | 8/2005 | Kelly et al. |
| 2006/0004043 A1 | 1/2006 | Bhagwat et al. |
| 2007/0049610 A1 | 3/2007 | Dillon et al. |
| 2007/0161670 A1 | 7/2007 | Staab et al. |
| 2008/0004297 A1 | 1/2008 | Cai et al. |
| 2008/0004318 A1 | 1/2008 | Chelliah et al. |
| 2008/0188467 A1 | 8/2008 | Wong et al. |
| 2008/0280879 A1 | 11/2008 | Brickner et al. |
| 2008/0293739 A1 | 11/2008 | Trede |
| 2009/0246198 A1 | 10/2009 | Dong et al. |
| 2010/0105661 A1 | 4/2010 | Shirakami et al. |
| 2010/0160355 A1 | 6/2010 | DeGoey et al. |
| 2011/0182812 A1 | 7/2011 | Szardenings et al. |
| 2011/0269740 A1 | 11/2011 | Sunny et al. |
| 2011/0313003 A1 | 12/2011 | Shi et al. |
| 2012/0065188 A1 | 3/2012 | Brickner et al. |
| 2012/0165370 A1 | 7/2012 | Tang et al. |
| 2012/0214842 A1 | 8/2012 | Donello et al. |
| 2012/0282233 A1 | 11/2012 | Rolshausen et al. |
| 2013/0267521 A1 | 10/2013 | Castro et al. |
| 2013/0281399 A1 | 10/2013 | McLure et al. |
| 2013/0302248 A1 | 11/2013 | Gangadharmath et al. |
| 2014/0142102 A1 | 4/2014 | Fairfax et al. |
| 2014/0225082 A1 | 8/2014 | Park et al. |
| 2014/0249204 A1 | 9/2014 | Vainchenker et al. |
| 2014/0286964 A1 | 9/2014 | Hubbard et al. |
| 2014/0288048 A1 | 9/2014 | Castro et al. |
| 2016/0016914 A1 | 1/2016 | Ladziata et al. |
| 2016/0118600 A1 | 4/2016 | Kim et al. |
| 2016/0220592 A1 | 8/2016 | Franz et al. |
| 2017/0107216 A1 | 4/2017 | Wu et al. |
| 2017/0121346 A1 | 5/2017 | Sprengler et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0226095 A1 | 8/2017 | Tazi et al. |
| 2017/0298040 A1 | 10/2017 | Bennett et al. |

(Continued)

FOREIGN PATENT DOCUMENTS

| | | |
|---|---|---|
| CN | 102838600 | 12/2012 |
| CN | 102838601 | 12/2012 |

(Continued)

OTHER PUBLICATIONS

Atzrodt et al., "The Renaissance of H/D Exchange," Angew Chem Int Ed., 2007, 7744-7765.

Baxter et al., "Acquired mutation of the tyrosine kinase JAK2 in human myeloproliferative disorders," Lancet., 2005, 365:1054-1061.

Bennett et al., "Proposals for the classification of the myelodysplastic syndromes," Br J Haematol., 1982, 51:189-199.

Berge et al., "Pharmaceutical Salts," Journal of Pharmaceutical Science, 1977, 66:1-19 pages.

Blom et al., "Preparative LC-MS Purification: Improved Compound Specific Method Optimization," J Combi Chem., 2004, 2004, 6:874-883.

(Continued)

*Primary Examiner* — Charanjit Aulakh
(74) *Attorney, Agent, or Firm* — Fish & Richardson P.C.

(57) ABSTRACT

The present application provides tricyclic urea compounds that modulate the activity of the V617F variant of JAK2, which are useful in the treatment of various diseases, including cancer.

55 Claims, No Drawings

Specification includes a Sequence Listing.

(56) References Cited

U.S. PATENT DOCUMENTS

| | | |
|---|---|---|
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0031557 A1 | 2/2018 | Scherrer et al. |
| 2018/0086719 A1 | 3/2018 | Chandrasekhar et al. |
| 2018/0104245 A1 | 4/2018 | Hansen |
| 2018/0179159 A1 | 6/2018 | Becknell et al. |
| 2018/0237797 A1 | 8/2018 | Loh |
| 2019/0152913 A1 | 5/2019 | Becknell et al. |
| 2019/0152988 A1 | 5/2019 | Sprengler et al. |
| 2019/0256492 A1 | 8/2019 | Tu et al. |
| 2021/0395251 A1 | 12/2021 | Shepard et al. |
| 2021/0395257 A1 | 12/2021 | Yu et al. |
| 2022/0002299 A1 | 1/2022 | Liu et al. |
| 2022/0169649 A1 | 6/2022 | Ai et al. |
| 2022/0213108 A1 | 7/2022 | Buesking et al. |
| 2022/0281887 A1 | 9/2022 | Shepard et al. |

FOREIGN PATENT DOCUMENTS

| | | |
|---|---|---|
| CN | 104311426 | 1/2015 |
| CN | 104725249 | 6/2015 |
| CN | 105461714 | 4/2016 |
| CN | 105481765 | 4/2016 |
| CN | 105732591 | 7/2016 |
| CN | 109575022 | 4/2019 |
| CN | 109608504 | 4/2019 |
| CN | 111484480 | 8/2020 |
| EP | 0329012 | 8/1989 |
| EP | 0481448 | 4/1992 |
| EP | 0652218 | 5/1995 |
| EP | 1692281 | 10/2005 |
| EP | 2309567 | 10/2010 |
| EP | 3277293 | 2/2018 |
| EP | 3277820 | 2/2018 |
| EP | 3578555 | 12/2019 |
| FR | 2996129 | 4/2014 |
| JP | 62209062 | 9/1987 |
| JP | 07089957 | 4/1995 |
| JP | 2000123973 | 4/2000 |
| JP | 2003107641 | 4/2003 |
| JP | 2004196702 | 7/2004 |
| KR | 20140111166 | 9/2014 |
| KR | 20150002266 | 1/2015 |
| KR | 20160123112 | 10/2016 |
| KR | 20170003469 | 6/2017 |
| WO | WO 93/17681 | 9/1993 |
| WO | WO 93/17682 | 9/1993 |
| WO | WO 95/18127 | 7/1995 |
| WO | WO 97/34893 | 9/1997 |
| WO | WO 97/47601 | 12/1997 |
| WO | WO 98/16184 | 4/1998 |
| WO | WO 98/40373 | 9/1998 |
| WO | WO 99/61444 | 12/1999 |
| WO | WO 99/64400 | 12/1999 |
| WO | WO 2000/041695 | 7/2000 |
| WO | WO 2000/067754 | 11/2000 |
| WO | WO 2000/068230 | 11/2000 |
| WO | WO 2001/023389 | 4/2001 |
| WO | WO 2001/042247 | 6/2001 |
| WO | WO 2001/047891 | 7/2001 |
| WO | WO 2001/058899 | 8/2001 |
| WO | WO 2001/070229 | 9/2001 |
| WO | WO 2002/000196 | 1/2002 |
| WO | WO 2002/091830 | 11/2002 |
| WO | WO 2003/062209 | 7/2003 |
| WO | WO 2003/074045 | 9/2003 |
| WO | WO 2004/014866 | 2/2004 |
| WO | WO 2004/024693 | 3/2004 |
| WO | WO 2004/030635 | 4/2004 |
| WO | WO 2004/031161 | 4/2004 |
| WO | WO 2004/039806 | 5/2004 |
| WO | WO 2004/055004 | 7/2004 |
| WO | WO 2004/080463 | 9/2004 |
| WO | WO 2005/00765 8 | 1/2005 |
| WO | WO 2005/003100 | 1/2005 |
| WO | WO 2005/009967 | 2/2005 |
| WO | WO 2005/028478 | 3/2005 |
| WO | WO 2005/061460 | 7/2005 |
| WO | WO 2005/072412 | 8/2005 |
| WO | WO 2005/080377 | 9/2005 |
| WO | WO 2005/082367 | 9/2005 |
| WO | WO 2005/110410 | 11/2005 |
| WO | WO 2005/112932 | 12/2005 |
| WO | WO 2005/117890 | 12/2005 |
| WO | WO 2005/121138 | 12/2005 |
| WO | WO 2006/021448 | 3/2006 |
| WO | WO 2006/032470 | 3/2006 |
| WO | WO 2006/039718 | 4/2006 |
| WO | WO 2006/045096 | 4/2006 |
| WO | WO 2006/045 827 | 5/2006 |
| WO | WO 2006/065 842 | 6/2006 |
| WO | WO 2006/072828 | 7/2006 |
| WO | WO 2006/074147 | 7/2006 |
| WO | WO 2006/108107 | 10/2006 |
| WO | WO 2006/122156 | 11/2006 |
| WO | WO 2007/002781 | 1/2007 |
| WO | WO 2007/007919 | 1/2007 |
| WO | WO 2007/016525 | 2/2007 |
| WO | WO 2007/022946 | 3/2007 |
| WO | WO 2007/03 8209 | 4/2007 |
| WO | WO 2007/047653 | 4/2007 |
| WO | WO 2007/051062 | 5/2007 |
| WO | WO 2007/076092 | 5/2007 |
| WO | WO 2007/077949 | 7/2007 |
| WO | WO 2007/110868 | 10/2007 |
| WO | WO 2007/112347 | 10/2007 |
| WO | WO 2007/113565 | 10/2007 |
| WO | WO 2007/125405 | 11/2007 |
| WO | WO 2007/133637 | 11/2007 |
| WO | WO 2007/136465 | 11/2007 |
| WO | WO 2007/140222 | 12/2007 |
| WO | WO 2007/147217 | 12/2007 |
| WO | WO 2008/000409 | 1/2008 |
| WO | WO 2008/005956 | 1/2008 |
| WO | WO 2008/007127 | 1/2008 |
| WO | WO 2008/011109 | 1/2008 |
| WO | WO 2008/011174 | 1/2008 |
| WO | WO 2008/021924 | 2/2008 |
| WO | WO 2008/024977 | 2/2008 |
| WO | WO 2008/046919 | 4/2008 |
| WO | WO 2008/060090 | 5/2008 |
| WO | WO 2008/064107 | 5/2008 |
| WO | WO 2008/079965 | 7/2008 |
| WO | WO 2008/084861 | 7/2008 |
| WO | WO 2008/092231 | 8/2008 |
| WO | WO 2008/112217 | 9/2008 |
| WO | WO 2008/113558 | 9/2008 |
| WO | WO 2008/124083 | 10/2008 |
| WO | WO 2008/135524 | 11/2008 |
| WO | WO 2008/151184 | 12/2008 |
| WO | WO 2009/024095 | 2/2009 |
| WO | WO 2009/042970 | 4/2009 |
| WO | WO 2009/114512 | 9/2009 |
| WO | WO 2010/006130 | 1/2010 |
| WO | WO 2010/026771 | 3/2010 |
| WO | WO 2010/039518 | 4/2010 |
| WO | WO 2010/042684 | 4/2010 |
| WO | WO 2010/077947 | 7/2010 |
| WO | WO 2010/078229 | 7/2010 |
| WO | WO 2010/080537 | 7/2010 |
| WO | WO 2010/101949 | 9/2010 |
| WO | WO 2010/106436 | 9/2010 |
| WO | WO 2010/107765 | 9/2010 |
| WO | WO 2010/107768 | 9/2010 |
| WO | WO 2010/123975 | 10/2010 |
| WO | WO 2010/125350 | 11/2010 |
| WO | WO 2010/129816 | 11/2010 |
| WO | WO 2010/141062 | 12/2010 |
| WO | WO 2010/143168 | 12/2010 |
| WO | WO 2010/143169 | 12/2010 |
| WO | WO 2010/143170 | 12/2010 |
| WO | WO 2011/004276 | 1/2011 |

(56) References Cited

FOREIGN PATENT DOCUMENTS

| | | |
|---|---|---|
| WO | WO 2011/022439 | 2/2011 |
| WO | WO 2011/028864 | 3/2011 |
| WO | WO 2011/047432 | 4/2011 |
| WO | WO 2011/050245 | 4/2011 |
| WO | WO 2011/053861 | 5/2011 |
| WO | WO 2011/068899 | 6/2011 |
| WO | WO 2011/072275 | 6/2011 |
| WO | WO 2011/075630 | 6/2011 |
| WO | WO 2011/078143 | 6/2011 |
| WO | WO 2011/078369 | 6/2011 |
| WO | WO 2011/086053 | 7/2011 |
| WO | WO 2011/097717 | 8/2011 |
| WO | WO 2011/103557 | 8/2011 |
| WO | WO 2011/112687 | 9/2011 |
| WO | WO 2011/123693 | 10/2011 |
| WO | WO 2011/137428 | 11/2011 |
| WO | WO 2011/146882 | 11/2011 |
| WO | WO 2012/061696 | 5/2012 |
| WO | WO 2012/066578 | 5/2012 |
| WO | WO 2012/078902 | 6/2012 |
| WO | WO 2012/085176 | 6/2012 |
| WO | WO 2012/089828 | 7/2012 |
| WO | WO 2012/097479 | 7/2012 |
| WO | WO 2012/116237 | 8/2012 |
| WO | WO 2012/127506 | 9/2012 |
| WO | WO 2013/007765 | 1/2013 |
| WO | WO 2013/033093 | 3/2013 |
| WO | WO 2013/033268 | 3/2013 |
| WO | WO 2013/033270 | 3/2013 |
| WO | WO 2013/033981 | 3/2013 |
| WO | WO 2013/049352 | 4/2013 |
| WO | WO 2013/062987 | 5/2013 |
| WO | WO 2013/067036 | 5/2013 |
| WO | WO 2013/086229 | 6/2013 |
| WO | WO 2013/156869 | 10/2013 |
| WO | WO 2013/158928 | 10/2013 |
| WO | WO 2013/167653 | 11/2013 |
| WO | WO 2013/175281 | 11/2013 |
| WO | WO 2013/191112 | 12/2013 |
| WO | WO 2014/018891 | 1/2014 |
| WO | WO 2014/023377 | 2/2014 |
| WO | WO 2014/051653 | 4/2014 |
| WO | WO 2014/074580 | 5/2014 |
| WO | WO 2014/087165 | 6/2014 |
| WO | WO 2014/120764 | 8/2014 |
| WO | WO 2014/203152 | 12/2014 |
| WO | WO 2014/204263 | 12/2014 |
| WO | WO 2015/001518 | 1/2015 |
| WO | WO 2015/009812 | 1/2015 |
| WO | WO 2015/025228 | 2/2015 |
| WO | WO 2015/036560 | 3/2015 |
| WO | WO 2015/049022 | 4/2015 |
| WO | WO 2015/086523 | 6/2015 |
| WO | WO 2015/124063 | 8/2015 |
| WO | WO 2015/144001 | 10/2015 |
| WO | WO 2015/168079 | 11/2015 |
| WO | WO 2016/009076 | 1/2016 |
| WO | WO 2016/116900 | 7/2016 |
| WO | WO 2016/123627 | 8/2016 |
| WO | WO 2016/128465 | 8/2016 |
| WO | WO 2016/160860 | 10/2016 |
| WO | WO 2016/190847 | 12/2016 |
| WO | WO 2016/197027 | 12/2016 |
| WO | WO 2017/003723 | 1/2017 |
| WO | WO 2017/004134 | 1/2017 |
| WO | WO 2017/029601 | 2/2017 |
| WO | WO 2017/059319 | 4/2017 |
| WO | WO 2017/072039 | 5/2017 |
| WO | WO 2017/072283 | 5/2017 |
| WO | WO 2017/075394 | 5/2017 |
| WO | WO 2017/090002 | 6/2017 |
| WO | WO 2017/103931 | 6/2017 |
| WO | WO 2017/205538 | 11/2017 |
| WO | WO 2017/223452 | 12/2017 |
| WO | WO 2018/009622 | 1/2018 |
| WO | WO 2018/046933 | 3/2018 |
| WO | WO 2018/057805 | 3/2018 |
| WO | WO 2018/068017 | 4/2018 |
| WO | WO 2018/083098 | 5/2018 |
| WO | WO 2018/112382 | 6/2018 |
| WO | WO 2018/140512 | 8/2018 |
| WO | WO 2018/140600 | 8/2018 |
| WO | WO 2018/144478 | 8/2018 |
| WO | WO 2018/204176 | 11/2018 |
| WO | WO 2018/204765 | 11/2018 |
| WO | WO 2018/222901 | 12/2018 |
| WO | WO 2018/231745 | 12/2018 |
| WO | WO 2018/237370 | 12/2018 |
| WO | WO 2019/060860 | 3/2019 |
| WO | WO 2019/070492 | 4/2019 |
| WO | WO 2019/129213 | 7/2019 |
| WO | WO 2019/135920 | 7/2019 |
| WO | WO 2019/177975 | 9/2019 |
| WO | WO 2019/201283 | 10/2019 |
| WO | WO 2019/214546 | 11/2019 |
| WO | WO 2021/018012 | 2/2021 |

OTHER PUBLICATIONS

Blom et al., "Optimizing Preparative LC-MS Configurations and Methods for Parallel Synthesis Purification," J Combi Chem., 2003, 5:670.

Blom et al., "Two-Pump at Column Dilution Configuration for Preparative LC-MS," J Combi Chem., 2002, 4:295.

Ceesay et al., "The JAK2 V617F mutation is rare in RARS but common in RARS-T," Leukemia, 2006, 20:2060-2061.

Dommaraju et al., "An efficient catalyst-free chemoselective multicomponent reaction for the synthesis of pyrimidine functionalized pyrrolo-annelated derivatives," RSC Adv., Jan. 1, 2015, 5:24327-24335.

Eisenhauer et al., "New response evaluation criteria in solid tumours: Revised RECIST guideline (version 1.1)," European Journal of Cancer, Jan. 2009, 45(2):228-247.

Harris et al., "World Health Organization classification of neoplastic diseases of the hematopoietic and lymphoid tissues: report of the Clinical Advisory Committee meeting—Airlie House, Virginia, Nov. 1997," J Clin Oncol., 1999, 17:3835-3849.

Hart et al., "Structure-Based Design of Selective Janus Kinase 2 Imidazo[4,5-d]pyrrolo[2,3-b]pyridine Inhibitors," ACS Med Chem Lett., Aug. 13, 2015, 6(8):845-849.

International Search Report and Written Opinion in International Appln. No. PCT/US2021/037870, dated Aug. 13, 2021, 13 pages.

International Search Report and Written Opinion in International Appln. No. PCT/US2021/037877, dated Aug. 13, 2021, 10 pages.

International Search Report and Written Opinion in International Appln. No. PCT/US2021/040182, dated Sep. 22, 2021, 12 pages.

International Search Report and Written Opinion in International Appln. No. PCT/US2021/040185, dated Sep. 22, 2021, 15 pages.

International Search Report and Written Opinion in International Appln. No. PCT/US2021/047687, dated Nov. 19, 2021, 16 pages.

International Search Report and Written Opinion in International Appln. No. PCT/US2021/064295, dated Mar. 17, 2022, 15 pages.

International Search Report and Written Opinion in International Appln. No. PCT/US2022/017654, dated May 30, 2022, 22 pages.

James et al., "A unique clonal JAK2 mutation leading to constitutive signalling causes polycythaemia vera," Nature, 2005, 434:1144-1148.

Jisha et al., "Exploration of 3,6-dihydroimidazo(4,5-d)pyrrolo(2,3-b)pyridin-2(1H)-one derivatives as JAK inhibitors using various in silico techniques," In Silico Pharmacology, 2017, 5(1):1-23.

Kerekes et al., "Aurora kinase inhibitors based on the imidazo[1,2-a]pyrazine core: fluorine and deuterium incorporation improve oral absorption and exposure," J Med Chem., 2011, 54:201-210.

Khalaf et al., "Structure-based design and synthesis of antiparasitic pyrrolopyrimidines targeting pteridine reductase 1," J Med Chem., Jul. 9, 2014, 57(15):6479-6494.

Kralovics et al., "A gain-of-function mutation of JAK2 in myeloproliferative disorders," N Engl J Med., 2005, 352:1779-1790.

(56) References Cited

OTHER PUBLICATIONS

Kulagawski et al., "Identification of imidazo-pyrrolopyridines as novel and potent JAK1 inhibitors," J Med Chem., 2012, 55(12):5901-5921.
Labadie et al., "Design and evaluation of novel 8-oxo-pyridopyrimidine Jak1/2 inhibitors," Bioorg Med Chem Lett., Nov. 2013, 23(21):5923-5930.
Leroy et al., "Differential effect of inhibitory strategies of the V617 mutant of JAK2 on cytokine receptor signaling," Journal of Allergy and Clinical Immunology, Jul. 2019, 144(1):224-235.
Levine et al., "Activating mutation in the tyrosine kinase JAK2 in polycythemia vera, essential thrombocythemia, and myeloid metaplasia with myelofibrosis," Cancer Cell., 2005, 7:387-397.
Ma et al., "Mutation Profile of JAK2 Transcripts in Patients with Chronic Myeloproliferative Neoplasias," J. Mol. Diagn., Jan. 2009, 11(1):49-53.
Remington's Pharmaceutical Sciences, 17th ed., Mack Publishing Company, Easton, Pa., 1985, p. 1418.
STN Search Report, Conducted Dec. 10, 2019, 379 pages.
STN Search Report, Conducted Dec. 2019, 1 page.
STN Search Report, Conducted Dec. 2020, 11 pages.
STN Search Report, Conducted Jun. 19, 2021, 236 pages.
STN Search Report, Conducted Jun. 2019, 316 pages.
STN Search Report, Conducted Jun. 2019, 292 pages.
STN Search Report, Conducted Jun. 2019, 13 pages.
STN Search Report, Conducted Jun. 2019, 39 pages.
STN Search Report, Conducted Oct. 2019, 14 pages.
STN Search Report, Conducted Sep. 2019, 236 pages.
STN Search Report, Conducted Sep. 2019, 5 pages.
Vainchecker et al., "JAK inhibitors for the treatment of myeloproliferative neoplasms and other disorders," F1000Research., 2018, 7:82.
Vardiman et al., "The 2008 revision of the World Health Organization (WHO) classification of myeloid neoplasms and acute leukemia: rationale and important changes," Blood 2009, 114:937-951.
Vardiman et al., "The World Health Organization (WHO) classification of the myeloid neoplasms," Blood 2002, 100:2292-2302.
Wilmes et al., "Mechanism of homodimeric cytokine receptor activation and dysregulation by oncogenic mutations," Science, 2020, 367:643-652.
Woods et al., "Activation of JAK/STAT Signaling in Megakaryocytes Sustains Myeloproliferation In Vivo," Clin Cancer Res., 2019, 25(19):5901-5912.
Xu et al., "Design, synthesis and biological evaluation of deuterated nintedanib for improving pharmacokinetic properties," J Label Compd Radiopharm., 2015, 58:308-312.
Yamagishi et al., "Discovery of 3,6-dihydroimidazo[4,5-d]pyrrolo[2,3-b]pyridin-2(1H)-one derivatives as novel JAK inhibitors," Biorg & Med Chem., 2015, 23(15):4846-4859.
Yamagishi et al., "Discovery of tricyclic dipyrrolopyridine derivatives as novel JAK inhibitors," Biorg & Med Chem, 2017, 25(20):5311-5326.
Yang et al., "Three-component reaction for synthesis of 2-amino-6-aryl-5-(phenylamino)-3,7-dihydro-4H-pyrrolo[2,3-d]pyrimidin-4-one derivatives in water," J Hetero Chem., 2020, 57(9):3271-3278.
Zak et al., "Discovery and optimization of C-2 methyl imidazopyrrolopyridines as potent and orally bioavailable JAK1 inhibitors with selectivity over JAK2," J Med Chem., 2012, 55(13):6176-6193.
Brunning et al., "Myelodysplastic syndromes/neoplasms," in Chapter 5, Swerdlow, et al., eds. WHO Classification of Tumours of Haematopoietic and Lymphoid Tissues., 4th edition, 2008, 21 pages.
Dommaraju et al., "An efficient catalyst-free chemoselective multicomponent reaction for the synthesis of pyrimidine functionalized pyrrolo-annelated derivatives," Electronic Supplementary Information for RSC Adv., Jan. 1, 2015, 64 pages.
Quiroga et al., "Generation of pyrrolo[2,3-d] pyrimidines. Unexpected products in the multicomponent reaction of 6-aminopyrimidines, dimedone, and arylglyoxal," Tetrahedron Letters, Oct. 2010, 51(41):5443-5447.

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: Biotin-labeled peptide, custom synthesis

<400> SEQUENCE: 1

Glu Gln Glu Asp Glu Pro Glu Gly Asp Tyr Phe Glu Trp Leu Glu
1               5                   10                  15

TRICYCLIC UREA COMPOUNDS AS JAK2 V617F INHIBITORS

TECHNICAL FIELD

The present invention provides tricyclic urea compounds that modulate the activity of the V617F variant of JAK2 and are useful in the treatment of diseases related to the V617F variant of JAK2, including cancer.

BACKGROUND

Janus kinase (JAK) 2 plays pivotal roles in signaling by several cytokine receptors. The mutant JAK2 V617F is the most common molecular event associated with myeloproliferative neoplasms. Selective targeting of the JAK2 V617F mutant may be useful for treating various pathologies, while sparing essential JAK2 functions. This application is directed to this need and others.

SUMMARY

The present invention relates to, inter alia, compounds of Formula I:

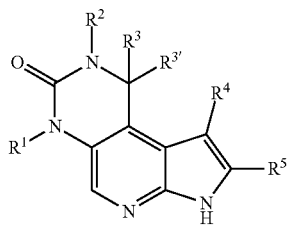

I or pharmaceutically acceptable salts thereof, wherein constituent members are defined herein.

The present invention further provides pharmaceutical compositions comprising a compound of Formula I, or a pharmaceutically acceptable salt thereof, and a pharmaceutically acceptable carrier.

The present invention further provides methods of inhibiting an activity of the V617F variant of JAK2 kinase comprising contacting the kinase with a compound of Formula I, or a pharmaceutically acceptable salt thereof.

The present invention further provides methods of treating a disease or a disorder associated with expression or activity of the V617F variant of JAK2 kinase in a patient by administering to a patient a therapeutically effective amount of a compound of Formula I, or a pharmaceutically acceptable salt thereof.

The present invention further provides a compound of Formula I, or a pharmaceutically acceptable salt thereof, for use in any of the methods described herein.

The present invention further provides use of a compound of Formula I, or a pharmaceutically acceptable salt thereof, for the preparation of a medicament for use in any of the methods described herein.

DETAILED DESCRIPTION

The present application provides compounds of Formula I;

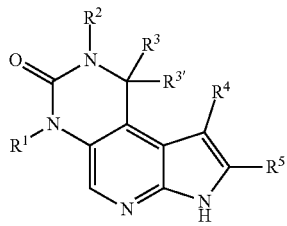

I or a pharmaceutically acceptable salt thereof, wherein:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

$R^2$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{2A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;

each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $NHOR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}$, $NR^{c23}C(O)NR^{c23}R^{d23}$, $C(=NR^{e23})R^{b23}$, $C(=NR^{e23})NR^{c23}R^{d23}$, $NR^{c23}C(=NR^{e23})NR^{c23}R^{d23}$, $NR^{c23}C(=NR^{e23})R^{b23}$, $NR^{c23}S(O)R^{b23}$, $NR^{c23}S(O)NR^{c23}R^{d23}$, $NR^{c23}S(O)_2R^{b23}$, $NR^{c23}S(O)(=NR^{e23})R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, and $OS(O)_2R^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{2C}$ are each optionally substituted with 1, 2, 3, or 4 independently selected $R^{M}$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^{M}$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ and $R^{3'}$ are each independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

or, $R^3$ and $R^{3'}$ attached to the same C atom, together with the C atom to which they are attached, form a 3-10 membered cycloalkyl or a 4-10 membered heterocycloalkyl group, wherein the 3-10 membered cycloalkyl or 4-10 membered heterocycloalkyl group is optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O) NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, 4, 5, 6, 7, or 8 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, C(O)NR$^{c42}$(OR$^{a42}$), C(O)OR$^{a42}$, OC(O)R$^{b42}$, OC(O)NR$^{c42}$R$^{d42}$, NR$^{c42}$R$^{d42}$, NR$^{c42}$NR$^{c42}$R$^{d42}$ NR$^{c42}$C(O)R$^{b42}$, NR$^{c42}$C(O)OR$^{a42}$, NR$^{c42}$C(O)NR$^{c42}$R$^{d42}$, C(=NR$^{e42}$)R$^{b42}$, C(=NR$^{e42}$)NR$^{c42}$R$^{d42}$, NR$^{c42}$C(=NR$^{e42}$)NR$^{c42}$R$^{d42}$, NR$^{c42}$C(=NR$^{e42}$)R$^{b42}$, NR$^{c42}$S(O)R$^{b42}$, NR$^{c42}$S(O) NR$^{c42}$R$^{d42}$, NR$^{c42}$S(O)$_2$R$^{b42}$, NR$^{c42}$S(O)(=NR$^{e42}$)R$^{b42}$, NR$^{c42}$S(O)$_2$NR$^{c42}$R$^{d42}$, S(O)R$^{b42}$, S(O)NR$^{c42}$R$^{d42}$, S(O)$_2$ R$^{b42}$, S(O)$_2$NR$^{c42}$R$^{d42}$, OS(O)(=NR$^{e42}$)R$^{b42}$, and OS(O)$_2$ R$^{b42}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{4B}$ are each optionally substituted with 1, 2, 3, 4, 5, 6, 7, or 8 independently selected R$^{4C}$ substituents;

each R$^{a42}$, R$^{c42}$, and R$^{d42}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a42}$, R$^{c42}$ and R$^{d42}$ are each optionally substituted with 1, 2, 3, 4, 5, 6, 7, or 8 independently selected R$^{4C}$ substituents;

or, any R$^{c42}$ and R$^{d42}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{4C}$ substituents;

each R$^{b42}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b42}$ are each optionally substituted with 1, 2, 3, 4, 5, 6, 7, or 8 independently selected R$^{4C}$ substituents;

each R$^{e42}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{4C}$ is independently selected from D, halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a43}$, SR$^{a43}$, NHOR$^{a43}$, C(O)R$^{b43}$, C(O)NR$^{c43}$R$^{d43}$, C(O)NR$^{c43}$(OR$^{a43}$), C(O)OR$^{a43}$, OC(O)R$^{b43}$, OC(O)NR$^{c43}$R$^{d43}$, NR$^{c43}$R$^{d43}$, NR$^{c43}$NR$^{c43}$R$^{d43}$, NR$^{c43}$C(O)R$^{b43}$, NR$^{c43}$C(O) OR$^{a43}$, NR$^{c43}$C(O)NR$^{c43}$R$^{d43}$, C(=NR$^{e43}$)R$^{b43}$, C(=NR$^{e43}$)NR$^{c43}$R$^{d43}$, NR$^{c43}$C(=NR$^{e43}$)NR$^{c43}$R$^{d43}$, NR$^{c43}$C(=NR$^{e43}$)R$^{b43}$, NR$^{c43}$S(O)R$^{b43}$, NR$^{c43}$S(O) NR$^{c43}$R$^{d43}$, NR$^{c43}$S(O)$_2$R$^{b43}$, NR$^{c43}$S(O)(=NR$^{e43}$)R$^{b43}$, NR$^{c43}$S(O)$_2$NR$^{c43}$R$^{d43}$, S(O)R$^{b43}$, S(O)NR$^{c43}$R$^{d43}$, S(O)$_2$ R$^{b43}$, S(O)$_2$NR$^{c43}$R$^{d43}$, OS(O)(=NR$^{e43}$)R$^{b43}$, and OS(O)$_2$ R$^{b43}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl- of R$^{4C}$ are each optionally substituted with 1, 2, 3, or 4 independently selected R$^M$ substituents;

each R$^{a43}$, R$^{c43}$, and R$^{d43}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a43}$, R$^{c43}$ and R$^{d43}$ are each optionally substituted with 1, 2, 3, or 4 independently selected R$^M$ substituents;

or, any R$^{c43}$ and R$^{d43}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b43}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b43}$ are each optionally substituted with 1, 2, 3, or 4 independently selected R$^M$ substituents;

each R$^{e43}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

R$^5$ is selected from H, D, halo, C$_{2-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a5}$, SR$^{a5}$, NHOR$^{a5}$, C(O)R$^{b5}$, C(O)NR$^{c5}$R$^{d5}$, C(O)NR$^{c5}$(OR$^{a5}$), C(O)OR$^{a5}$, OC(O)R$^{b5}$, OC(O)NR$^{c5}$R$^{d5}$, NR$^{c5}$R$^{d5}$, NR$^{c5}$NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$) NR$^{c5}$R$^{d5}$, NR$^{c5}$C(=NR$^{e5}$)R$^{b5}$, NR$^{c5}$S(O)R$^{b5}$, NR$^{c5}$S(O) NR$^{c5}$R$^{d5}$, NR$^{c5}$S(O)$_2$R$^{b5}$, NR$^{c5}$S(O)(=NR$^{e5}$)R$^{b5}$, NR$^{c5}$S (O)$_2$NR$^{c5}$R$^{d5}$, S(O)R$^{b5}$, S(O)NR$^{c5}$R$^{d5}$, S(O)$_2$R$^{b5}$, S(O)$_2$ NR$^{c5}$R$^{d5}$, OS(O)(=NR$^{e5}$)R$^{b5}$, and OS(O)$_2$R$^{b5}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^5$ are each o ptionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)R^{b51}$, $NR^{c51}S(O)NR^{c51}R^{d51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)R^{b52}$, $NR^{c52}S(O)NR^{c52}R^{d52}$, $NR^{c52}S(O)_2R^{b52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, 4, 5, 6, 7, or 8 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, 4, 5, 6, 7, or 8 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, 4, 5, 6, 7, or 8 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}NR^{c53}R^{d53}$, $NR^{c53}C(O)R^{b53}$, $NR^{c53}C(O)OR^{a53}$, $NR^{c53}C(O)NR^{c53}R^{d53}$, $C(=NR^{e53})R^{b53}$, $C(=NR^{e53})NR^{c53}R^{d53}$, $NR^{c53}C(=NR^{e53})NR^{c53}R^{d53}$, $NR^{c53}C(=NR^{e53})R^{b53}$, $NR^{c53}S(O)R^{b53}$, $NR^{c53}S(O)NR^{c53}R^{d53}$, $NR^{c53}S(O)_2R^{b53}$, $NR^{c53}S(O)(=NR^{e53})R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, $OS(O)(=NR^{e53})R^{b53}$, and $OS(O)_2R^{b53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents;

each $R^{e53}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^M$ is independently selected from H, D, OH, halo, oxo, CN, C(O)OH, $NH_2$, $NO_2$, $SF_5$, $C_{1-6}$ alkyl, $C_{1-6}$alkoxy, $C_{1-6}$haloalkoxy, $C_{1-6}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;

$R^2$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;

each $R^{2A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)$ OR$^{a21}$, NR$^{c21}$C(O)NR$^{c21}$R$^{d21}$, C(=NR$^{e21}$)R$^{b21}$, C(=NR$^{e21}$)NR$^{c21}$R$^{d21}$, NR$^{c21}$C(=NR$^{e21}$)NR$^{c21}$R$^{d21}$, NR$^{c21}$C(=NR$^{e21}$)R$^{b21}$, NR$^{c21}$S(O)R$^{b21}$, NR$^{c21}$S(O) NR$^{c21}$R$^{d21}$, NR$^{c21}$S(O)$_2$R$^{b21}$, NR$^{c21}$S(O)(=NR$^{e21}$)R$^{b21}$, NR$^{c21}$S(O)$_2$NR$^{c21}$R$^{d21}$, S(O)R$^{b21}$, S(O)NR$^{c21}$R$^{d21}$, S(O)$_2$ R$^{b21}$, S(O)$_2$NR$^{c21}$R$^{d21}$, OS(O)(=NR$^{e21}$)R$^{b21}$, and OS(O)$_2$ R$^{b21}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{2A}$ are each optionally substituted with 1, 2, 3, 4, 5, 6, 7, or 8 independently selected R$^{2B}$ substituents;

each R$^{a21}$, R$^{c21}$, and R$^{d21}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a21}$, R$^{c21}$ and R$^{d21}$ are each optionally substituted with 1, 2, 3, 4, 5, 6, 7, or 8 independently selected R$^{2B}$ substituents;

or, any R$^{c21}$ and R$^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{2B}$ substituents;

each R$^{b21}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b21}$ are each optionally substituted with 1, 2, 3, 4, 5, 6, 7, or 8 independently selected R$^{2B}$ substituents;

each R$^{e21}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{2B}$ is independently selected from halo, oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a22}$, SR$^{a22}$, NHOR$^{a22}$, C(O)R$^{b22}$, C(O)NR$^{c22}$R$^{d22}$, C(O) NR$^{c22}$(OR$^{a22}$), C(O)OR$^{a22}$, OC(O)R$^{b22}$, OC(O)NR$^{c22}$R$^{d22}$, NR$^{c22}$R$^{d22}$, NR$^{c22}$NR$^{c22}$R$^{d22}$, NR$^{c22}$C(O)R$^{b22}$, NR$^{c22}$C(O) OR$^{a22}$, NR$^{c22}$C(O)NR$^{c22}$R$^{d22}$, C(=NR$^{e22}$)R$^{b22}$, C(=NR$^{e22}$)NR$^{c22}$R$^{d22}$, NR$^{c22}$C(=NR$^{e22}$)NR$^{c22}$R$^{d22}$, NR$^{c22}$C(=NR$^{e22}$)R$^{b22}$, NR$^{c22}$S(O)R$^{b22}$, NR$^{c22}$S(O) NR$^{c22}$R$^{d22}$, NR$^{c22}$S(O)$_2$R$^{b22}$, NR$^{c22}$S(O)(=NR$^{e22}$)R$^{b22}$, NR$^{c22}$S(O)$_2$NR$^{c22}$R$^{d22}$, S(O)R$^{b22}$, S(O)NR$^{c22}$R$^{d22}$, S(O)$_2$ R$^{b22}$, S(O)$_2$NR$^{c22}$R$^{d22}$, OS(O)(=NR$^{e22}$)R$^{b22}$, and OS(O)$_2$ R$^{b22}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{2B}$ are each optionally substituted with 1, 2, 3, 4, 5, 6, 7, or 8 independently selected R$^{2C}$ substituents;

each R$^{a22}$, R$^{c22}$, and R$^{d22}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a22}$, R$^{c22}$ and R$^{d22}$ are each optionally substituted with 1, 2, 3, 4, 5, 6, 7, or 8 independently selected R$^{2C}$ substituents;

or, any R$^{c22}$ and R$^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{2C}$ substituents;

each R$^{b22}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b22}$ are each optionally substituted with 1, 2, 3, 4, 5, 6, 7, or 8 independently selected R$^{2C}$ substituents;

each R$^{e22}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{2C}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a23}$, SR$^{a23}$, NHOR$^{a23}$, C(O)R$^{b23}$, C(O)NR$^{c23}$R$^{d23}$, C(O)NR$^{c23}$ (OR$^{a23}$), C(O)OR$^{a23}$, OC(O)R$^{b23}$, OC(O)NR$^{c23}$R$^{d23}$, NR$^{c23}$R$^{d23}$, NR$^{c23}$NR$^{c23}$R$^{d23}$, NR$^{c23}$C(O)R$^{b23}$, NR$^{c23}$C(O) OR$^{a23}$, NR$^{c23}$C(O)NR$^{c23}$R$^{d23}$, C(=NR$^{e23}$)R$^{b23}$, C(=NR$^{e23}$)NR$^{c23}$R$^{d23}$, NR$^{c23}$C(=NR$^{e23}$)NR$^{c23}$R$^{d23}$, NR$^{c23}$C(=NR$^{e23}$)R$^{b23}$, NR$^{c23}$S(O)R$^{b23}$, NR$^{c23}$S(O) NR$^{c23}$R$^{d23}$, NR$^{c23}$S(O)$_2$R$^{b23}$, NR$^{c23}$S(O)(=NR$^{e23}$)R$^{b23}$, NR$^{c23}$S(O)$_2$NR$^{c23}$R$^{d23}$, S(O)R$^{b23}$, S(O)NR$^{c23}$R$^{d23}$, S(O)$_2$ R$^{b23}$, S(O)$_2$NR$^{c23}$R$^{d23}$, OS(O)(=NR$^{e23}$)R$^{b23}$, and OS(O)$_2$ R$^{b23}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ and $R^{3'}$ are each independently selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

or, $R^3$ and $R^{3'}$ attached to the same C atom, together with the C atom to which they are attached, form a 3-10 membered cycloalkyl or a 4-10 membered heterocycloalkyl group, wherein the 3-10 membered cycloalkyl or 4-10 membered heterocycloalkyl group is optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^{M}$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^{M}$ substituents;

or, any R$^{c33}$ and R$^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b33}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b33}$ are each optionally substituted with 1, 2, 3, or 4 independently selected R$^M$ substituents;

each R$^{e33}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-;

R$^4$ is selected from H, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a4}$, SR$^{a4}$, NHOR$^{a4}$, C(O)R$^{b4}$, C(O)NR$^{c4}$R$^{d4}$, C(O)NR$^{c4}$(OR$^{a4}$), C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$) NR$^{c4}$R$^{d4}$, NR$^{c4}$C(=NR$^{e4}$)R$^{b4}$, NR$^{c4}$S(O)R$^{b4}$, NR$^{c4}$S(O) NR$^{c4}$R$^{d4}$, NR$^{c4}$S(O)$_2$R$^{b4}$, NR$^{c4}$S(O)(=NR$^{e4}$)R$^{b4}$, NR$^{c4}$S (O)$_2$NR$^{c4}$R$^{d4}$, S(O)R$^{b4}$, S(O)NR$^{c4}$R$^{d4}$, S(O)$_2$R$^{b4}$, S(O)$_2$ NR$^{c4}$R$^{d4}$, OS(O)(=NR$^{e4}$)R$^{b4}$, and OS(O)$_2$R$^{b4}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^4$ are each optionally substituted with 1, 2, 3, 4, 5, 6, 7, or 8 independently selected R$^{4A}$ substituents;

each R$^{a4}$, R$^{c4}$, and R$^{d4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a4}$, R$^{c4}$ and R$^{d4}$ are each optionally substituted with 1, 2, 3, 4, 5, 6, 7, or 8 independently selected R$^{4A}$ substituents;

or, any R$^{c4}$ and R$^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{4A}$ substituents;

each R$^{b4}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b4}$ are each optionally substituted with 1, 2, 3, 4, 5, 6, 7, or 8 independently selected R$^{4A}$ substituents;

each R$^{e4}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{4A}$ is independently selected from halo, oxo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, (4-10 membered heterocycloalkyl)-C$_{1-6}$ alkyl-, CN, NO$_2$, OR$^{a41}$, SR$^{a41}$, NHOR$^{a41}$, C(O)R$^{b41}$, C(O)NR$^{c41}$R$^{d41}$, C(O) NR$^{c41}$(OR$^{a41}$), C(O)OR$^{a41}$, OC(O)R$^{b41}$, OC(O)NR$^{c41}$R$^{d41}$, NR$^{c41}$R$^{d41}$, NR$^{c41}$NR$^{c41}$R$^{d41}$, NR$^{c41}$C(O)R$^{b41}$, NR$^{c41}$C(O) OR$^{a41}$, NR$^{c41}$C(O)NR$^{c41}$R$^{d41}$, C(=NR$^{e41}$)R$^{b41}$, C(=NR$^{e41}$)NR$^{c41}$R$^{d41}$, NR$^{c41}$C(=NR$^{e41}$)NR$^{c41}$R$^{d41}$, NR$^{c41}$C(=NR$^{e41}$)R$^{b41}$, NR$^{c41}$S(O)R$^{b41}$, NR$^{c41}$S(O) NR$^{c41}$R$^{d41}$, NR$^{c41}$S(O)$_2$R$^{b41}$, NR$^{c41}$S(O)(=NR$^{e41}$)R$^{b41}$, NR$^{c41}$S(O)$_2$NR$^{c41}$R$^{d41}$, S(O)R$^{b41}$, S(O)NR$^{c41}$R$^{d41}$, S(O)$_2$ R$^{b41}$, S(O)$_2$NR$^{c41}$R$^{d41}$, OS(O)(=NR$^{e41}$)R$^{b41}$, and OS(O)$_2$ R$^{b41}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{4A}$ are each optionally substituted with 1, 2, 3, 4, 5, 6, 7, or 8 independently selected R$^{4B}$ substituents;

each R$^{a41}$, R$^{c41}$, and R$^{d41}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a41}$, R$^{c41}$ and R$^{d41}$ are each optionally substituted with 1, 2, 3, 4, 5, 6, 7, or 8 independently selected R$^{4B}$ substituents;

or, any R$^{c41}$ and R$^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{4B}$ substituents;

each R$^{b41}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$, $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{b42}$, $NR^{c42}S(O)R^{b42}$, $NR^{c42}S(O)NR^{c42}R^{d42}$, $NR^{c42}S(O)_2R^{b42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, 4, 5, 6, 7, or 8 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, 4, 5, 6, 7, or 8 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, 4, 5, 6, 7, or 8 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NR^{e43})NR^{c43}R^{d43}$, $NR^{c43}C(=NR^{e43})NR^{c43}R^{d43}$, $NR^{c43}C(=NR^{e43})R^{b43}$, $NR^{c43}S(O)R^{b43}$, $NR^{c43}S(O)NR^{c43}R^{d43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, and $OS(O)_2R^{b43}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{4C}$ are each optionally substituted with 1, 2, 3, or 4 independently selected $R^M$ substituents;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a43}$, $R^{c43}$ and $R^{d43}$ are each optionally substituted with 1, 2, 3, or 4 independently selected $R^M$ substituents;

or, any $R^{c43}$ and $R^{d43}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b43}$ are each optionally substituted with 1, 2, 3, or 4 independently selected $R^M$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl- $C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)R^{b51}$, $NR^{c51}S(O)NR^{c51}R^{d51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)$ OR$^{a52}$, NR$^{c52}$C(O)NR$^{c52}$R$^{d52}$, C(=NR$^{e52}$)R$^{b52}$, C(=NR$^{e52}$)NR$^{c52}$R$^{d52}$, NR$^{c52}$C(=NR$^{e52}$)NR$^{c52}$R$^{d52}$, NR$^{c52}$C(=NR$^{e52}$)R$^{b52}$, NR$^{c52}$S(O)R$^{b52}$, NR$^{c52}$S(O) NR$^{c52}$R$^{d52}$, NR$^{c52}$S(O)$_2$R$^{b52}$, NR$^{c52}$S(O)(=NR$^{e52}$)R$^{b52}$, NR$^{c52}$S(O)$_2$NR$^{c52}$R$^{d52}$, S(O)R$^{b52}$, S(O)NR$^{c52}$R$^{d52}$, S(O)$_2$ R$^{b52}$, S(O)$_2$NR$^{c52}$R$^{d52}$, OS(O)(=NR$^{e52}$)R$^{b52}$, and OS(O)$_2$ R$^{b52}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{5B}$ are each optionally substituted with 1, 2, 3, 4, 5, 6, 7, or 8 independently selected R$^{5C}$ substituents;

each R$^{a52}$, R$^{c52}$, and R$^{d52}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a52}$, R$^{c52}$ and R$^{d52}$ are each optionally substituted with 1, 2, 3, 4, 5, 6, 7, or 8 independently selected R$^{5C}$ substituents;

or, any R$^{c52}$ and R$^{d52}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{5C}$ substituents;

each R$^{b52}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{b52}$ are each optionally substituted with 1, 2, 3, 4, 5, 6, 7, or 8 independently selected R$^{5C}$ substituents;

each R$^{e52}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

each R$^{5C}$ is independently selected from halo, oxo, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl-, CN, NO$_2$, OR$^{a53}$, SR$^{a53}$, NHOR$^{a53}$, C(O)R$^{b53}$, C(O)NR$^{c53}$R$^{d53}$, C(O)NR$^{c53}$(OR$^{a53}$), C(O)OR$^{a53}$, OC(O)R$^{b53}$, OC(O)NR$^{c53}$R$^{d53}$, NR$^{c53}$R$^{d53}$, NR$^{c53}$NR$^{c53}$R$^{d53}$, NR$^{c53}$C(O)R$^{b53}$, NR$^{c53}$C(O) OR$^{a53}$, NR$^{c53}$C(O)NR$^{c53}$R$^{d53}$, C(=NR$^{e53}$)R$^{b53}$, C(=NR$^{e53}$)NR$^{c53}$R$^{d53}$, NR$^{c53}$C(=NR$^{e53}$)NR$^{c53}$R$^{d53}$, NR$^{c53}$C(=NR$^{e53}$)R$^{b53}$, NR$^{c53}$S(O)R$^{b53}$, NR$^{c53}$S(O) NR$^{c53}$R$^{d53}$, NR$^{c53}$S(O)$_2$R$^{b53}$, NR$^{c53}$S(O)(=NR$^{e53}$)R$^{b53}$, NR$^{c53}$S(O)$_2$NR$^{c53}$R$^{d53}$, S(O)R$^{b53}$, S(O)NR$^{c53}$R$^{d53}$, S(O)$_2$ R$^{b53}$, S(O)$_2$NR$^{c53}$R$^{d53}$, OS(O)(=NR$^{e53}$)R$^{b53}$, and OS(O)$_2$ R$^{b53}$, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, (4-7 membered heterocycloalkyl)-C$_{1-6}$ alkyl- of R$^{5C}$ are each optionally substituted with 1, 2, 3, or 4 independently selected R$^M$ substituents;

each R$^{a53}$, R$^{c53}$, and R$^{d53}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{a53}$, R$^{c53}$ and R$^{d53}$ are each optionally substituted with 1, 2, 3, or 4 independently selected R$^M$ substituents;

or, any R$^{c53}$ and R$^{d53}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected R$^M$ substituents;

each R$^{b53}$ is independently selected from H, C$_{1-6}$ alkyl, C$_{1-6}$ haloalkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-, wherein the C$_{1-6}$ alkyl, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl- of R$^{b53}$ are each optionally substituted with 1, 2, 3, or 4 independently selected R$^M$ substituents;

each R$^{e53}$ is independently selected from H, OH, CN, C$_{1-6}$ alkyl, C$_{1-6}$ alkoxy, C$_{1-6}$ haloalkyl, C$_{1-6}$ haloalkoxy, C$_{2-6}$ alkenyl, C$_{2-6}$ alkynyl, phenyl, C$_{3-7}$ cycloalkyl, 5-6 membered heteroaryl, 4-7 membered heterocycloalkyl, phenyl-C$_{1-6}$ alkyl-, C$_{3-7}$ cycloalkyl-C$_{1-6}$ alkyl-, (5-6 membered heteroaryl)-C$_{1-6}$ alkyl-, and (4-7 membered heterocycloalkyl)-C$_{1-6}$ alkyl-; and each R$^M$ is independently selected from H, OH, halo, oxo, CN, C(O)OH, NH$_2$, NO$_2$, SF$_5$, C$_{1-6}$ alkyl, C$_{1-6}$ alkoxy, C$_{1-6}$ haloalkoxy, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-.

In some embodiments:

R$^1$ is selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-;

R$^2$ is selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)NR^{c21}R^{d21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, or 4 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, or 4 independently selected $R^{2B}$ substituents;

each $R^{2B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)NR^{c22}R^{d22}$, $NR^{c22}S(O)_2R^{b22}$, $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, or 4 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, or 4, independently selected $R^{2C}$ substituents;

each $R^{2C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}C(O)R^{b23}$, $NR^{c23}C(O)OR^{a23}$, $NR^{c23}C(O)NR^{c23}R^{d23}$, $NR^{c23}S(O)R^{b23}$, $NR^{c23}S(O)NR^{c23}R^{d23}$, $NR^{c23}S(O)_2R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, and $OS(O)_2R^{b23}$;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c23}$ and $R^{d23}$ attached to the same N atom, together with the N atom to which they are attached, form a 5-6 membered heteroaryl or a 4-7 membered heterocycloalkyl group;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ and $R^{3'}$ are each independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)NR^{c3}R^{d3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;

or, $R^3$ and $R^{3'}$ attached to the same C atom, together with the C atom to which they are attached, form a 3-10 membered cycloalkyl or a 4-10 membered heterocycloalkyl group, wherein the 3-10 membered cycloalkyl or 4-10 membered heterocycloalkyl group is optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, or 4 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, or 4 independently selected $R^{3A}$ substituents;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)NR^{c31}R^{d31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, or 4 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, or 4 independently selected $R^{3B}$ substituents;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)NR^{c32}R^{d32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, or 4 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, or 4 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, or 4 independently selected $R^{3C}$ substituents;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, NO$_2$, OR$^{a33}$, SR$^{a33}$, C(O)R$^{b33}$, C(O)NR$^{c33}$R$^{d33}$, C(O)NR$^{c33}$(OR$^{a33}$), C(O)OR$^{a33}$, OC(O)R$^{b33}$, OC(O)NR$^{c33}$R$^{d33}$, NR$^{c33}$R$^{d33}$, NR$^{c33}$C(O)R$^{b33}$, NR$^{c33}$C(O)OR$^{a33}$, NR$^{c33}$C(O)NR$^{c33}$R$^{d33}$, NR$^{c33}$S(O)R$^{b33}$, NR$^{c33}$S(O)NR$^{c33}$R$^{d33}$, NR$^{c33}$S(O)$_2$R$^{b33}$, NR$^{c33}$S(O)$_2$NR$^{c33}$R$^{d33}$, S(O)R$^{b33}$, S(O)NR$^{c33}$R$^{d33}$, S(O)$_2$R$^{b33}$, S(O)$_2$NR$^{c33}$R$^{d33}$, and OS(O)$_2$R$^{b33}$;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c33}$ and $R^{d33}$ attached to the same N atom, together with the N atom to which they are attached, form a 5-6 membered heteroaryl or a 4-7 membered heterocycloalkyl group;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a4}$, SR$^{a4}$, C(O)R$^{b4}$, C(O)NR$^{c4}$R$^{d4}$, C(O)NR$^{c4}$(OR$^{a4}$), C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)NR$^{c4}$R$^{d4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, and OS(O)$_2$R$^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, or 4 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, or 4 independently selected $R^{4A}$ substituents;

each $R^{4A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, OR$^{a41}$, SR$^{a41}$, C(O)R$^{b41}$, C(O)NR$^{c41}$R$^{d41}$, C(O)NR$^{c41}$(OR$^{a41}$), C(O)OR$^{a41}$, OC(O)R$^{b41}$, OC(O)NR$^{c41}$R$^{d41}$, NR$^{c41}$R$^{d41}$, NR$^{c41}$C(O)R$^{b41}$, NR$^{c41}$C(O)OR$^{a41}$, NR$^{c41}$C(O)NR$^{c41}$R$^{d41}$, NR$^{c41}$S(O)R$^{b41}$, NR$^{c41}$S(O)NR$^{c41}$R$^{d41}$, NR$^{c41}$S(O)$_2$R$^{b41}$, NR$^{c41}$S(O)$_2$NR$^{c41}$R$^{d41}$, S(O)R$^{b41}$, S(O)NR$^{c41}$R$^{d41}$, S(O)$_2$R$^{b41}$, S(O)$_2$NR$^{c41}$R$^{d41}$, and OS(O)$_2$R$^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, or 4 independently selected $R^{4B}$ substituents;

each $R^{4B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)NR^{c42}R^{d42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, or 4 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, or 4 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, or 4 independently selected $R^{4C}$ substituents;

each $R^{4C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}C(O)R^{b43}$, $NR^{c43}C(O)OR^{a43}$, $NR^{c43}C(O)NR^{c43}R^{d43}$, $NR^{c43}S(O)R^{b43}$, $NR^{c43}S(O)NR^{c43}R^{d43}$, $NR^{c43}S(O)_2R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, and $OS(O)_2R^{b43}$;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c43}$ and $R^{d43}$ attached to the same N atom, together with the N atom to which they are attached, form a 5-6 membered heteroaryl or a 4-7 membered heterocycloalkyl group;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, D, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, or 4 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, or 4 independently selected $R^{5A}$ substituents;

each $R^{5A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)NR^{c51}R^{d51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, or 4 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, or 4 independently selected $R^{5B}$ substituents;

each $R^{5B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)NR^{c52}R^{d52}$, $NR^{c52}S(O)R^{b52}$, $NR^{c52}S(O)NR^{c52}R^{d52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, or 4 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, or 4 independently selected $R^{5C}$ substituents;

each $R^{5C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $SR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)R^{b53}$, $NR^{c53}S(O)NR^{c53}R^{d53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, and $OS(O)_2R^{b53}$;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c53}$ and $R^{d53}$ attached to the same N atom, together with the N atom to which they are attached, form a 5-6 membered heteroaryl or a 4-7 membered heterocycloalkyl group; and each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments:

$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

$R^2$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents;

each $R^{2A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a21}$, $SR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}C(O)R^{b21}$, $NR^{c21}C(O)OR^{a21}$, $NR^{c21}C(O)NR^{c21}R^{d21}$, $NR^{c21}S(O)R^{b21}$, $NR^{c21}S(O)NR^{c21}R^{d21}$, $NR^{c21}S(O)_2R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, or 4 independently selected $R^{2B}$ substituents;

or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;

each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, or 4 independently selected $R^{2B}$ substituents;

each $R^{2B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO$_2$, $OR^{a22}$, $SR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}C(O)R^{b22}$, $NR^{c22}C(O)OR^{a22}$, $NR^{c22}C(O)NR^{c22}R^{d22}$, $NR^{c22}S(O)R^{b22}$, $NR^{c22}S(O)NR^{c22}R^{d22}$, $NR^{c22}S(O)_2R^{b22}$ $NR^{c22}S(O)_2NR^{c22}R^{d22}$, $S(O)R^{b22}$, $S(O)NR^{c22}R^{d22}$, $S(O)_2R^{b22}$, $S(O)_2NR^{c22}R^{d22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, or 4 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, or 4 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, or 4, independently selected $R^{2C}$ substituents;

each $R^{2C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}C(O)R^{b23}$, $NR^{c23}C(O)OR^{a23}$, $NR^{c23}C(O)NR^{c23}R^{d23}$, $NR^{c23}S(O)R^{b23}$, $NR^{c23}S(O)NR^{c23}R^{d23}$, $NR^{c23}S(O)_2R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, and $OS(O)_2R^{b23}$;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c23}$ and $R^{d23}$ attached to the same N atom, together with the N atom to which they are attached, form a 5-6 membered heteroaryl or a 4-7 membered heterocycloalkyl group;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ and $R^{3'}$ are each independently selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)NR^{c3}R^{d3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, or 4 independently selected $R^{3A}$ substituents;

or, $R^3$ and $R^{3'}$ attached to the same C atom, together with the C atom to which they are attached, form a 3-10 membered cycloalkyl or a 4-10 membered heterocycloalkyl group, wherein the 3-10 membered cycloalkyl or 4-10 membered heterocycloalkyl group is optionally substituted with 1, 2, 3, or 4 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, or 4 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, or 4 independently selected $R^{3A}$ substituents;

each $R^{3A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}C(O)R^{b31}$, $NR^{c31}C(O)OR^{a31}$, $NR^{c31}C(O)NR^{c31}R^{d31}$, $NR^{c31}S(O)R^{b31}$, $NR^{c31}S(O)NR^{c31}R^{d31}$, $NR^{c31}S(O)_2R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, or 4 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, or 4 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, or 4 independently selected $R^{3B}$ substituents;

each $R^{3B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}C(O)R^{b32}$, $NR^{c32}C(O)OR^{a32}$, $NR^{c32}C(O)NR^{c32}R^{d32}$, $NR^{c32}S(O)R^{b32}$, $NR^{c32}S(O)NR^{c32}R^{d32}$, $NR^{c32}S(O)_2R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, or 4 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, or 4 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, or 4 independently selected $R^{3C}$ substituents;

each $R^{3C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}C(O)R^{b33}$, $NR^{c33}C(O)OR^{a33}$, $NR^{c33}C(O)NR^{c33}R^{d33}$, $NR^{c33}S(O)R^{b33}$, $NR^{c33}S(O)NR^{c33}R^{d33}$, $NR^{c33}S(O)_2R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, and $OS(O)_2R^{b33}$;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c33}$ and $R^{d33}$ attached to the same N atom, together with the N atom to which they are attached, form a 5-6 membered heteroaryl or a 4-7 membered heterocycloalkyl group;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)NR^{c4}R^{d4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, or 4 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^M$ are each optionally substituted with 1, 2, 3, or 4 independently selected $R^{4A}$ substituents;

each $R^{4A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}C(O)R^{b41}$, $NR^{c41}C(O)OR^{a41}$, $NR^{c41}C(O)NR^{c41}R^{d41}$, $NR^{c41}S(O)R^{b41}$, $NR^{c41}S(O)NR^{c41}R^{d41}$, $NR^{c41}S(O)_2R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, or 4 independently selected $R^{4B}$ substituents;

each $R^{4B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}C(O)R^{b42}$, $NR^{c42}C(O)OR^{a42}$, $NR^{c42}C(O)NR^{c42}R^{d42}$, $NR^{c42}S(O)R^{b42}$, $NR^{c42}S(O)NR^{c42}R^{d42}$, $NR^{c42}S(O)_2R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, or 4 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, or 4 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, or 4 independently selected $R^{4C}$ substituents;

each $R^{4C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}C(O)R^{b43}$, $NR^{c43}C(O)OR^{a43}$, $NR^{c43}C(O)NR^{c43}R^{d43}$, $NR^{c43}S(O)R^{b43}$, $NR^{c43}S(O)NR^{c43}R^{d43}$, $NR^{c43}S(O)_2R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, and $OS(O)_2R^{b43}$;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c43}$ and $R^{d43}$ attached to the same N atom, together with the N atom to which they are attached, form a 5-6 membered heteroaryl or a 4-7 membered heterocycloalkyl group;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)NR^{c5}R^{d5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, or 4 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, or 4 independently selected $R^{5A}$ substituents;

each $R^{5A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $C(O)R^{b51}$, $C(O)NR^{c51}R^{d51}$, $C(O)NR^{c51}$ $(OR^{a51})$, $C(O)OR^{a51}$, $OC(O)R^{b51}$, $OC(O)NR^{c51}R^{d51}$, $NR^{c51}R^{d51}$, $NR^{c51}C(O)R^{b51}$, $NR^{c51}C(O)OR^{a51}$, $NR^{c51}C(O)NR^{c51}R^{d51}$, $NR^{c51}S(O)R^{b51}$, $NR^{c51}S(O)NR^{c51}R^{d51}$, $NR^{c51}S(O)_2R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, or 4 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, or 4 independently selected $R^{5B}$ substituents;

each $R^{5B}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $C(O)R^{b52}$, $C(O)NR^{c52}R^{d52}$, $C(O)NR^{c52}$ $(OR^{a52})$, $C(O)OR^{a52}$, $OC(O)R^{b52}$, $OC(O)NR^{c52}R^{d52}$, $NR^{c52}R^{d52}$, $NR^{c52}C(O)R^{b52}$, $NR^{c52}C(O)OR^{a52}$, $NR^{c52}C(O)$ $NR^{c52}R^{d52}$, $NR^{c52}S(O)R^{b52}$, $NR^{c52}S(O)NR^{c52}R^{d52}$, $NR^{c52}S(O)_2R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, or 4 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, or 4 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, or 4 independently selected $R^{5C}$ substituents;

each $R^{5C}$ is independently selected from halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $SR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $NR^{c53}S(O)R^{b53}$, $NR^{c53}S(O)NR^{c53}R^{d53}$, $NR^{c53}S(O)_2R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, and $OS(O)_2R^{b53}$;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

or, any $R^{c53}$ and $R^{d53}$ attached to the same N atom, together with the N atom to which they are attached, form a 5-6 membered heteroaryl or a 4-7 membered heterocycloalkyl group; and each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-.

In some embodiments, $R^1$ is selected from H, $C_{1-6}$ alkyl, $C_{1-6}$ haloalkyl, $C_{2-6}$ alkenyl, and $C_{2-6}$ alkynyl.

In some embodiments, $R^1$ is selected from H and $C_{1-6}$ alkyl.

In some embodiments, $R^1$ is selected from H and methyl.

In some embodiments, $R^1$ is H.

In some embodiments, $R^1$ is methyl.

In some embodiments, $R^2$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, or 4 independently selected $R^{2A}$ substituents.

In some embodiment, $R^2$ is selected from H, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-10}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl-, wherein the $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl- of $R^2$ are each optionally substituted with 1, 2, 3, or 4 independently selected $R^{2A}$ substituents.

In some embodiments, $R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl- of $R^2$ are each optionally substituted with 1, 2, 3, or 4 independently selected $R^{2A}$ substituents.

In some embodiments, $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1, 2, 3, or 4 independently selected $R^{2A}$ substituents.

In some embodiments, $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1 or 2 independently selected $R^{2A}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b21}$, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, C(O)$R^{b21}$, C(O)$NR^{c21}R^{d21}$, C(O)$NR^{c21}(OR^{a21})$, C(O)$OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{2A}$ are each optionally substituted with 1, 2, 3, or 4 independently selected $R^{2B}$ substituents.

In some embodiments, each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, C(O)$NR^{c21}R^{d21}$, C(O)$NR^{c21}(OR^{a21})$, C(O)$OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents.

In some embodiments, $R^{a21}$, $R^{b21}$, $R^{c21}$, and $R^{d21}$ are each independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents.

In some embodiments, $R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents.

In some embodiments, $R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1 or 2 independently selected $R^{2B}$ substituents.

In some embodiments, $R^{a21}$, $R^{b21}$, $R^{c21}$, and $R^{d21}$ are each independently selected from H, methyl, ethyl, phenyl, pyridinyl, cyclopropyl, cyclohexyl, dihydroisobenzofuranyl, tetrahydrofuranyl, tetrahydropyranyl, phenylmethyl, cyclohexylmethyl, tetrahydropyranylmethyl, cyclopropylmethyl, and pyridinylmethyl of $R^{a21}$, $R^{b21}$, $R^{c21}$, and $R^{d21}$ are each optionally substituted with 1, 2, 3, or 4 independently selected $R^{2B}$ substituents.

In some embodiments, $R^{a21}$, $R^{b21}$, $R^{c21}$, and $R^{d21}$ are each independently selected from H, methyl, ethyl, phenyl, pyridinyl, cyclopropyl, cyclohexyl, dihydroisobenzofuranyl, tetrahydrofuranyl, tetrahydropyranyl, phenylmethyl, cyclohexylmethyl, tetrahydropyranylmethyl, cyclopropylmethyl, and pyridinylmethyl of $R^{a21}$, $R^{b21}$, $R^{c21}$, and $R^{d21}$ are each optionally substituted with 1 or 2 independently selected $R^{2B}$ substituents.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1, 2, 3, or 4 independently selected $R^{2C}$ substituents.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 independently selected $R^{2C}$ substituents.

In some embodiments, each $R^{2C}$ is independently selected from D, halo, $C_{1-6}$ alkyl, $C_{1-6}$ haloalkyl, $C_{2-6}$ alkenyl, $C_{2-6}$ alkynyl, CN, $NO_2$, and $OR^{a23}$.

In some embodiments, each $R^{2C}$ is independently selected from halo, $C_{1-6}$ alkyl, $C_{1-6}$ haloalkyl, $C_{2-6}$ alkenyl, $C_{2-6}$ alkynyl, CN, $NO_2$, and $OR^{a23}$.

In some embodiments, each $R^{2C}$ is independently selected from CN and $OR^{a23}$.

In some embodiments, each $R^{a23}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a23}$ is H or $C_{1-6}$ alkyl.

In some embodiments, each $R^{a23}$ is H.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from $OR^{a23}$ and CN.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from $OR^{a23}$ and CN;
wherein each $R^{a23}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from $OR^{a23}$ and CN;
wherein each $R^{a23}$ is independently selected from H and $C_{1-6}$ alkyl.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN; and
each $R^{a22}$, $R^{c22}$, and $R^{d22}$ is independently selected from H, $C_{1-6}$ alkyl, $C_{1-6}$ haloalkyl, $C_{2-6}$ alkenyl, and $C_{2-6}$ alkynyl.

In some embodiments, each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN; and each $R^{a22}$, $R^{c22}$, and $R^{d22}$ is independently selected from H and $C_{1-6}$ alkyl.

In some embodiments, each $R^{2B}$ is independently selected from methyl, hydroxy, methoxy, dimethylamino, CN, and C(O)OH.

In some embodiments, $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1, 2, 3, or 4 independently selected $R^{2A}$ substituents; and each $R^{2A}$ is independently selected from fluoro, chloro, bromo, methyl, ethyl, piperazinyl, morpholinyl, piperidinyl, morpholinylmethyl, dimethylamino, C(O)OH, C(O)NHCH₃, C(O)NHOCH₃, C(O)NHCH₂CH₂OH, C(O)NHCH₂CH₂OCH₃, C(O)N(CH₃)CH₂CH₂OH, C(O)N(CH₃)CH₂CH₂OCH₃, C(O)NHCH₂C(O)NHNHCH₂-phenyl, C(O)NH-cyclopropyl, C(O)NH-cyclohexyl, C(O)NH-phenyl, C(O)NH-pyridinyl, C(O)N(CH₃)-pyridinyl, C(O)NH-dihydroisobenzofuranyl, C(O)NH-tetrahydrofuranyl, C(O)NH-tetrahydropyranyl, C(O)N(CH₃)-tetrahydropyranyl, C(O)NH-(cyclopropylmethyl), C(O)NH-(cyclohexylmethyl), C(O)NH-(phenylmethyl), C(O)NH-(tetrahydropyranylmethyl), C(O)NH-(pyridinylmethyl), NHC(O)-tetrahydropyranyl, NHC(O)CH₂CN, NHC(O)CH₂CH₃, NHCH₂C(O)OH, NHCH₂CH₂OCH₃, and S(O)₂NH₂, wherein the methyl, ethyl, piperazinyl, morpholinyl, piperidinyl, morpholinylmethyl, C(O)NH-cyclopropyl, C(O)NH-cyclohexyl, C(O)NH-phenyl, C(O)NH-pyridinyl, C(O)N(CH₃)-pyridinyl, C(O)NH-dihydroisobenzofuranyl, C(O)NH-tetrahydrofuranyl, C(O)NH-tetrahydropyranyl, C(O)N(CH₃)-tetrahydropyranyl, C(O)NH-(cyclopropylmethyl), C(O)NH-(cyclohexylmethyl), C(O)NH-(phenylmethyl), C(O)NH-(tetrahydropyranylmethyl), C(O)NH-(pyridinylmethyl), and NHC(O)-tetrahydropyranyl, are each optionally substituted with 1, 2, or 3 substituents independently selected from fluoro, methyl, hydroxy, hydroxymethyl, cyano, cyanomethyl, methoxy, and C(O)OH.

In some embodiments, $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1 or 2 independently selected $R^{2A}$ substituents; and each $R^{2A}$ is independently selected from fluoro, chloro, bromo, methyl, ethyl, piperazinyl, morpholinyl, piperidinyl, morpholinylmethyl, dimethylamino, C(O)OH, C(O)NHCH₃, C(O)NHOCH₃, C(O)NHCH₂CH₂OH, C(O)NHCH₂CH₂OCH₃, C(O)N(CH₃)CH₂CH₂OH, C(O)N(CH₃)CH₂CH₂OCH₃, C(O)NH-cyclopropyl, C(O)NH-cyclohexyl, C(O)NH-phenyl, C(O)NH-pyridinyl, C(O)N(CH₃)-pyridinyl, C(O)NH-dihydroisobenzofuranyl, C(O)NH-tetrahydrofuranyl, C(O)NH-tetrahydropyranyl, C(O)N(CH₃)-tetrahydropyranyl, C(O)NH-(cyclopropylmethyl), C(O)NH-(cyclohexylmethyl), C(O)NH-(phenylmethyl), C(O)NH-(tetrahydropyranylmethyl), C(O)NH-(pyridinylmethyl), and NHC(O)-tetrahydropyranyl, are each optionally substituted with 1, 2, or 3 substituents independently selected from fluoro, methyl, hydroxy, hydroxymethyl, cyano, cyanomethyl, methoxy, and C(O)OH.

In some embodiments, $R^3$ is selected from H, D, $C_{1-6}$ alkyl, $C_{1-6}$ haloalkyl, $C_{2-6}$ alkenyl, and $C_{2-6}$ alkynyl.

In some embodiments, $R^3$ is selected from H, $C_{1-6}$ alkyl, $C_{1-6}$ haloalkyl, $C_{2-6}$ alkenyl, and $C_{2-6}$ alkynyl.

In some embodiments, $R^3$ is selected from H and $C_{1-6}$ alkyl.

In some embodiments, $R^3$ is selected from H and methyl.

In some embodiments, $R^3$ is H.

In some embodiments, $R^3$ is $C_{1-6}$ alkyl.

In some embodiments, $R^3$ is methyl.

In some embodiments, $R^{3'}$ is selected from H, D, $C_{1-6}$ alkyl, $C_{1-6}$ haloalkyl, $C_{2-6}$ alkenyl, and $C_{2-6}$ alkynyl.

In some embodiments, $R^{3'}$ is selected from H, $C_{1-6}$ alkyl, $C_{1-6}$ haloalkyl, $C_{2-6}$ alkenyl, and $C_{2-6}$ alkynyl.

In some embodiments, $R^{3'}$ is selected from H and $C_{1-6}$ alkyl.

In some embodiments, $R^{3'}$ is H.

In some embodiments, $R^{3'}$ is $C_{1-6}$ alkyl.

In some embodiments, $R^3$ and $R^{3'}$ are each H.

In some embodiments, $R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO₂, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{44}$ substituents.

In some embodiments, $R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, NO₂, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{44}$ substituents.

In some embodiments, $R^4$ is selected from H, D, halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, CN, NO₂, $OR^{a4}$, and $C(O)OR^{a4}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^4$ are each optionally substituted with 1, 2, 3, or 4 independently selected $R^{4A}$ substituents.

In some embodiments, $R^4$ is selected from H, halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, (4-6 membered heterocycloalkyl)-$C_{1-6}$ alkyl-, CN, $NO_2$, $OR^{a4}$, and $C(O)OR^{a4}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^4$ are each optionally substituted with 1, 2, 3, or 4 independently selected $R^{4A}$ substituents.

In some embodiments, $R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents.

In some embodiments, $R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1 or 2 independently selected $R^{4A}$ substituents.

In some embodiments, each $R^{a4}$, $R^{b4}$, $R^{c4}$, and $R^{d4}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a4}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a4}$, $R^{b4}$, $R^{c4}$, and $R^{d4}$ is independently selected from H and $C_{1-6}$ alkyl.

In some embodiments, each $R^{a4}$ is independently selected from H and $C_{1-6}$ alkyl.

In some embodiments, each $R^{a4}$, $R^{b4}$, $R^{c4}$, and $R^{d4}$ is an independently selected $C_{1-6}$ alkyl.

In some embodiments, each $R^{a4}$ is an independently selected $C_{1-6}$ alkyl.

In some embodiments, each $R^{a4}$, $R^{b4}$, $R^{c4}$, and $R^{d4}$ is independently selected from H and methyl.

In some embodiments, each $R^{a4}$ is independently selected from H and methyl.

In some embodiments, each $R^{a4}$, $R^{b4}$, $R^{c4}$, and $R^{d4}$ is methyl.

In some embodiments, each $R^{a4}$ is methyl.

In some embodiments, $R^4$ is selected from H, methyl, ethenyl, isopropenyl, cyano, iodo, cyclopropyl, cyclohexenyl, phenyl, dihydropyridinyl, pyrazolyl, pyrrolyl, and methoxycarbonyl, wherein the methyl, ethenyl, isopropenyl, cyclopropyl, cyclohexenyl, phenyl, dihydropyridinyl, pyrazolyl, and pyrrolyl of $R^4$ are each optionally substituted with 1, 2, 3, or 4 independently selected $R^{4A}$ substituents.

In some embodiments, $R^4$ is selected from H, methyl, ethenyl, isopropenyl, cyano, iodo, cyclopropyl, cyclohexenyl, phenyl, dihydropyridinyl, pyrazolyl, pyrrolyl, and methoxycarbonyl, wherein the methyl, ethenyl, isopropenyl, cyclopropyl, cyclohexenyl, phenyl, dihydropyridinyl, pyrazolyl, and pyrrolyl of $R^4$ are each optionally substituted with 1 or 2 independently selected $R^{4A}$ substituents.

In some embodiments, each $R^{4A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2R^{b41}$, and $S(O)_2NR^{c41}R^{d41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, of $R^{4A}$ are each optionally substituted with 1, 2, 3, or 4 independently selected $R^{4B}$ substituents.

In some embodiments, each $R^{4A}$ is independently selected from halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2 R^{b41}$, and $S(O)_2NR^{c41}R^{d41}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, of $R^{4A}$ are each optionally substituted with 1, 2, 3, or 4 independently selected $R^{4B}$ substituents.

In some embodiments, each $R^{4A}$ is independently selected from halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2 R^{b41}$, and $S(O)_2NR^{c41}R^{d41}$, wherein the $C_{1-6}$ alkyl, $C_{2-6}$ alkenyl, $C_{2-6}$ alkynyl, phenyl, $C_{3-6}$ cycloalkyl, 5-6 membered heteroaryl, and 4-6 membered heterocycloalkyl, of $R^{4A}$ are each optionally substituted with 1 or 2 independently selected $R^{4B}$ substituents.

In some embodiments, each $R^{4A}$ is independently selected from halo, $C_{1-6}$ alkyl, phenyl, $C_{3-6}$ cycloalkyl, 5-6 membered heteroaryl, 4-6 membered heterocycloalkyl, CN, $OR^{a41}$, $C(O)R^{b41}$, $C(O)NR^{c41}R^{d41}$, $NR^{c41}C(O)R^{b41}$, $S(O)_2 R^{b41}$, and $S(O)_2NR^{c41}R^{d41}$, wherein the $C_{1-6}$ alkyl, phenyl, $C_{3-6}$ cycloalkyl, 5-6 membered heteroaryl, and 4-6 membered heterocycloalkyl, of $R^{4A}$ are each optionally substituted with 1, 2, 3, or 4 independently selected $R^{4B}$ substituents.

In some embodiments, each $R^{4A}$ is independently selected from halo, $C_{1-6}$ alkyl, phenyl, $C_{3-6}$ cycloalkyl, 5-6 membered heteroaryl, 4-6 membered heterocycloalkyl, CN, $OR^{a41}$, $C(O)R^{b41}$, $C(O)NR^{c41}R^{d41}$, $NR^{c41}C(O)R^{b41}$, $S(O)_2 R^{b41}$, and $S(O)_2NR^{c41}R^{d41}$, wherein the $C_{1-6}$ alkyl, phenyl, $C_{3-6}$ cycloalkyl, 5-6 membered heteroaryl, and 4-6 membered heterocycloalkyl, of $R^{4A}$ are each optionally substituted with 1 or 2 independently selected $R^{4B}$ substituents.

In some embodiments:
each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents; and each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{b41}$ are each optionally substituted with 1, 2, 3, or 4 independently selected $R^{4B}$ substituents.

In some embodiments:

each $R^{a41}$, $R^{c41}$, and $R^{d41}$ is independently selected from H, $C_{1-6}$ alkyl, and $C_{3-10}$ cycloalkyl-$C_{1-6}$ alkyl-;

or, any $R^{c41}$ and $R^{d41}$ attached to the same N atom, together with the N atom to which they are attached, 4-10 membered heterocycloalkyl group, wherein the 4-10 membered heterocycloalkyl group is optionally substituted with 1 or 2 independently selected $R^{4B}$ substituents; and each $R^{b41}$ is independently selected from H, $C_{1-6}$ alkyl, and $C_{3-10}$ cycloalkyl.

In some embodiments:

each $R^{a41}$, $R^{c41}$, and $R^{d41}$ is independently selected from H, $C_{1-6}$ alkyl, and $C_{3-6}$ cycloalkyl-$C_{1-6}$ alkyl-;

or, any $R^{c41}$ and $R^{d41}$ attached to the same N atom, together with the N atom to which they are attached, 4-10 membered heterocycloalkyl group, wherein the 4-10 membered heterocycloalkyl group is optionally substituted with 1 or 2 independently selected $R^{4B}$ substituents; and each $R^{b41}$ is independently selected from $C_{1-6}$ alkyl and $C_{3-6}$ cycloalkyl.

In some embodiments, each $R^{4B}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, and $NR^{c42}C(O)OR^{a42}$, wherein the $C_{1-6}$ alkyl, $C_{2-6}$ alkenyl, and $C_{2-6}$ alkynyl of $R^{4B}$ are each optionally substituted with 1, 2, 3, or 4 independently selected $R^{4C}$ substituents.

In some embodiments, each $R^{4B}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, and $NR^{c42}C(O)OR^{a42}$, wherein the $C_{1-6}$ alkyl, $C_{2-6}$ alkenyl, and $C_{2-6}$ alkynyl of $R^{4B}$ are each optionally substituted with 1, 2, 3, or 4 independently selected $R^{4C}$ substituents.

In some embodiments, each $R^{4B}$ is independently selected from $C_{1-6}$ alkyl, CN, $OR^{a42}$, $C(O)R^{b42}$, $C(O)NR^{c42}R^{d42}$, $NR^{c42}R^{d42}$, and $NR^{c42}C(O)R^{b42}$, wherein the $C_{1-6}$ alkyl of $R^{4B}$ is optionally substituted with 1, 2, 3, or 4 independently selected $R^{4C}$ substituents.

In some embodiments, each $R^{4B}$ is independently selected from $C_{1-6}$ alkyl, CN, $OR^{a42}$, $C(O)R^{b42}$, $C(O)NR^{c42}R^{d42}$, $NR^{c42}R^{d42}$, and $NR^{c42}C(O)R^{b42}$, wherein the $C_{1-6}$ alkyl of $R^{4B}$ is optionally substituted with 1 or 2 independently selected $R^{4C}$ substituents.

In some embodiments:

each $R^{a42}$, $R^{c42}$, and $R^{d42}$ is independently selected from H, $C_{1-6}$ alkyl, $C_{1-6}$ haloalkyl, $C_{2-6}$ alkenyl, and $C_{2-6}$ alkynyl; and each $R^{b42}$ is independently selected from H, $C_{1-6}$ alkyl, $C_{1-6}$ haloalkyl, $C_{2-6}$ alkenyl, and $C_{2-6}$ alkynyl.

In some embodiments:

each $R^{a42}$, $R^{c42}$, and $R^{d42}$ is independently selected from H and $C_{1-6}$ alkyl; and each $R^{b42}$ is an independently selected $C_{1-6}$ alkyl.

In some embodiments, each $R^{4C}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$.

In some embodiments, each $R^{4C}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$.

In some embodiments, each $R^{4C}$ is independently selected from $C(O)R^{b43}$, $C(O)NR^{c43}R^{d43}$, and $C(O)OR^{a43}$.

In some embodiments, each $R^{4C}$ is $C(O)NR^{c43}R^{d43}$.

In some embodiments, each $R^{a43}$, $R^{b43}$, $R^{c43}$, and $R^{d43}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a43}$, $R^{b43}$, $R^{c43}$, and $R^{d43}$ is independently selected from H and $C_{1-6}$ alkyl.

In some embodiments, each $R^{a43}$, $R^{b43}$, $R^{c43}$, and $R^{d43}$ is H.

In some embodiments, each $R^{4C}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$; and each $R^{a43}$, $R^{b43}$, $R^{c43}$, and $R^{d43}$ is independently selected from H and $C_{1-6}$ alkyl.

In some embodiments, each $R^{4C}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$; and each $R^{a43}$, $R^{b43}$, $R^{c43}$, and $R^{d43}$ is independently selected from H and $C_{1-6}$ alkyl.

In some embodiments, each $R^{4A}$ is independently selected from chloro, fluoro, methyl, hydroxy, methoxy, cyano, C(O)OH, morpholinyl, piperazinyl, cyclopropyl, phenyl, pyrazolyl, $C(O)NH_2$, $C(O)N(CH_3)_2$, $C(O)NH_2$-(cyclopropylmethyl), $C(O)NHCH_2CH_3$, $C(O)NHCH_2CH_2OH$, $NHC(O)CH_3$, $SO_2CH_3$, $SO_2CH_2CH_3$, $SO_2NHCH_3$, $SO_2N(CH_3)_2$, $SO_2$-isopropyl, $SO_2$-cyclopropyl, and $SO_2$-morpholinyl, wherein the methyl, morpholinyl, piperazinyl, cyclopropyl, phenyl, pyrazolyl, $C(O)NH_2$-(cyclopropylmethyl), $SO_2$-isopropyl, $SO_2$-cyclopropyl, and $SO_2$-morpholinyl of $R^{4A}$ are each optionally substituted with 1 or 2 substituents independently selected from methyl, hydroxy, cyano, dimethylamino, $C(O)CH_3$, $NHC(O)CH_3$, $C(O)NHCH_3$, and $CH(CH_3)C(O)NH_2$.

In some embodiments, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

In some embodiments, $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1 or 2 independently selected $R^{5A}$ substituents.

In some embodiments, $R^5$ is selected from H, halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^5$ are each optionally substituted with 1, 2, 3, or 4 independently selected $R^{5A}$ substituents.

In some embodiments, $R^5$ is selected from H, halo, $C_{1-6}$ alkyl, $C_{1-6}$ haloalkyl, $C_{2-6}$ alkenyl, $C_{2-6}$ alkynyl, phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl, $C_{3-6}$ cycloalkyl, 5-6 membered heteroaryl, 4-6 membered heterocycloalkyl, phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^5$ are each optionally substituted with 1 or 2 independently selected $R^{5A}$ substituents.

In some embodiments, $R^5$ is selected from H, halo, phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents.

In some embodiments, $R^5$ is selected from H, halo, phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1 or 2 independently selected $R^{5A}$ substituents.

In some embodiments, $R^5$ is selected from H, halo, $C_{3-6}$ cycloalkyl, and $C_{6-10}$ aryl, wherein the $C_{3-6}$ cycloalkyl and $C_{6-10}$ aryl are each optionally substituted by 1 or 2 independently selected $R^{5A}$ substituents.

In some embodiments, $R^5$ is selected from H, halo, $C_{3-6}$ cycloalkyl, and $C_{6-10}$ aryl, wherein the $C_{6-10}$ aryl is optionally substituted by 1 or 2 independently selected $R^{5A}$ substituents.

In some embodiments, $R^5$ is selected from H, halo, and $C_{6-10}$ aryl which is optionally substituted by 1 or 2 independently selected $R^{5A}$ substituents.

In some embodiments, $R^5$ is selected from H, halo, $C_{3-6}$ cycloalkyl, and phenyl wherein the $C_{3-6}$ cycloalkyl and $C_{6-10}$ aryl are each optionally substituted by 1 or 2 independently selected $R^{5A}$ substituents.

In some embodiments, $R^5$ is selected from H, halo, $C_{3-6}$ cycloalkyl, and phenyl wherein the phenyl is optionally substituted by 1 or 2 independently selected $R^{5A}$ substituents.

In some embodiments, $R^5$ is selected from H, halo, and phenyl which is optionally substituted by 1 or 2 independently selected $R^{5A}$ substituents.

In some embodiments, each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1 or 2 independently selected $R^{5B}$ substituents.

In some embodiments, each $R^{5A}$ is independently selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1 or 2 independently selected $R^{5B}$ substituents.

In some embodiments, each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1, 2, 3, or 4 independently selected $R^{5B}$ substituents.

In some embodiments, each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1 or 2 independently selected $R^{5B}$ substituents.

In some embodiments, each $R^{5A}$ is piperidinylmethyl, which is optionally substituted by 1 or 2 independently selected $R^{5B}$ groups.

In some embodiments, each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$.

In some embodiments, each $R^{5B}$ is independently selected from $S(O)R^{b52}$, $S(O)NR^{c52}R^{d52}$, $S(O)_2R^{b52}$, and $S(O)_2NR^{c52}R^{d52}$.

In some embodiments, each $R^{5B}$ is independently selected from $S(O)R^{b52}$ and $S(O)_2R^{b52}$.

In some embodiments, each $R^{5B}$ is $S(O)_2R^{b52}$.

In some embodiments, each $R^{a52}$, $R^{b52}$, $R^{c52}$, and $R^{d52}$ is independently selected from H, $C_{1-6}$ alkyl, $C_{1-6}$ haloalkyl, $C_{2-6}$ alkenyl, and $C_{2-6}$ alkynyl.

In some embodiments, each $R^{a52}$, $R^{b52}$, $R^{c52}$, and $R^{d52}$ is independently selected from H and $C_{1-6}$ alkyl.

In some embodiments, each $R^{a52}$, $R^{b52}$, $R^{c52}$, and $R^{d52}$ is H.

In some embodiments, each $R^{a52}$, $R^{b52}$, $R^{c52}$, and $R^{d52}$ is an independently selected $C_{1-6}$ alkyl.

In some embodiments, each $R^{a52}$, $R^{b52}$, $R^{c52}$, and $R^{d52}$ is methyl.

In some embodiments, each $R^{5B}$ is $S(O)_2R^{b52}$, wherein each $R^{b52}$ is independently selected from H and $C_{1-6}$ alkyl.

In some embodiments, each $R^{5B}$ is methylsulfonyl.

In some embodiments, $R^5$ is selected from H, bromo, cyclopropyl, and phenyl, wherein the phenyl of $R^5$ is optionally substituted by piperidinylmethyl, and wherein the piperidinylmethyl is optionally substituted by methyl sulfonyl.

In some embodiments, $R^5$ is selected from H, bromo, and phenyl which is optionally substituted by piperidinylmethyl, wherein the piperidinylmethyl is optionally substituted by methyl sulfonyl.

In some embodiments:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl-, wherein the $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b21}$, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H, D, $C_{1-6}$ alkyl, $C_{1-6}$ haloalkyl, $C_{2-6}$ alkenyl, and $C_{2-6}$ alkynyl;

$R^{3'}$ is selected from H, D, $C_{1-6}$ alkyl, $C_{1-6}$ haloalkyl, $C_{2-6}$ alkenyl, and $C_{2-6}$ alkynyl;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2R^{b41}$, and $S(O)_2NR^{c41}R^{d41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, of $R^{4A}$ are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{b41}$ are each optionally substituted with 1, 2, 3, or 4 independently selected $R^{4B}$ substituents;

each $R^{4B}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, and $NR^{c42}C(O)OR^{a42}$, wherein the $C_{1-6}$ alkyl, $C_{2-6}$ alkenyl, and $C_{2-6}$ alkynyl of $R^{4B}$ are each optionally substituted with 1, 2, 3, or 4 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, and $C_{2-6}$ alkynyl;

each $R^{b42}$ is independently selected from H, $C_{1-6}$ alkyl, $C_{1-6}$ haloalkyl, $C_{2-6}$ alkenyl, and $C_{2-6}$ alkynyl;

each $R^{4C}$ is independently selected from D, halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$;

each $R^{a43}$, $R^{b43}$, $R^{c43}$, and $R^{d43}$ is independently selected from H and $C_{1-6}$ alkyl;

$R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl-, wherein the $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b21}$, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H, $C_{1-6}$ alkyl, $C_{1-6}$ haloalkyl, $C_{2-6}$ alkenyl, and $C_{2-6}$ alkynyl;

$R^{3'}$ is selected from H, $C_{1-6}$ alkyl, $C_{1-6}$ haloalkyl, $C_{2-6}$ alkenyl, and $C_{2-6}$ alkynyl;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2R^{b41}$, and $S(O)_2NR^{c41}R^{d41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, of $R^{4A}$ are each optionally substituted with 1, 2, 3, or 4 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{b41}$ are each optionally substituted with 1, 2, 3, or 4 independently selected $R^{4B}$ substituents;

each $R^{4B}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$, $NR^{c42}C(O)R^{b42}$, and $NR^{c42}C(O)OR^{a42}$, wherein the $C_{1-6}$ alkyl, $C_{2-6}$ alkenyl, and $C_{2-6}$ alkynyl of $R^{4B}$ are each optionally substituted with 1, 2, 3, or 4 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, and $C_{2-6}$ alkynyl;

each $R^{b42}$ is independently selected from H, $C_{1-6}$ alkyl, $C_{1-6}$ haloalkyl, $C_{2-6}$ alkenyl, and $C_{2-6}$ alkynyl;

each $R^{4C}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$;

each $R^{a43}$, $R^{b43}$, $R^{c43}$, and $R^{d43}$ is independently selected from H and $C_{1-6}$ alkyl;

$R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents;

each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents;

each $R^{5B}$ is independently selected from $C(O)R^{b52}$, $C(O)NR^{c52}R^{d52}$, $C(O)OR^{a52}$, $NR^{c52}S(O)R^{b52}$, $NR^{c52}S(O)_2R^{b52}$, $S(O)R^{b52}$, $S(O)NR^{c52}R^{d52}$, $S(O)_2R^{b52}$, and $S(O)_2NR^{c52}R^{d52}$; and each $R^{a52}$, $R^{b52}$, $R^{c52}$, and $R^{d52}$ is independently selected from H and $C_{1-6}$ alkyl.

In some embodiments:

$R^1$ is selected from H and $C_{1-6}$ alkyl;

$R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H and $C_{1-6}$ alkyl;

$R^{3'}$ is selected from H and $C_{1-6}$ alkyl;

$R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from halo, $C_{1-6}$ alkyl, phenyl, $C_{3-6}$ cycloalkyl, 5-6 membered heteroaryl, 4-6 membered heterocycloalkyl, CN, $OR^{a41}$, $C(O)R^{b41}$, $C(O)NR^{c41}R^{d41}$, $NR^{c41}C(O)R^{b41}$, $S(O)_2R^{b41}$, and $S(O)_2NR^{c41}R^{d41}$, wherein the $C_{1-6}$ alkyl, phenyl, $C_{3-6}$ cycloalkyl, 5-6 membered heteroaryl, and 4-6 membered heterocycloalkyl, of $R^{4A}$ are each optionally substituted with 1, 2, 3, or 4 independently selected $R^{4B}$ substituents;

each $R^{4B}$ is independently selected from $C_{1-6}$ alkyl, CN, $OR^{a42}$, $C(O)R^{b42}$, $C(O)NR^{c42}R^{d42}$, $NR^{c42}R^{d42}$, and $NR^{c42}C(O)R^{b42}$, wherein the $C_{1-6}$ alkyl of $R^{4B}$ is optionally substituted with 1 or 2 independently selected $R^{4C}$ substituents;

each $R^{a42}$, $R^{b42}$, $R^{c42}$, and $R^{d42}$ is independently selected from H and $C_{1-6}$ alkyl;

each $R^{4C}$ is an independently selected $C(O)NR^{c43}R^{d43}$ substituent;

each $R^{c43}$ and $R^{d43}$ is independently selected from H and $C_{1-6}$ alkyl;

$R^5$ is selected from H, halo, phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents;

each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1 or 2 independently selected $R^{5B}$ substituents;

each $R^{5B}$ is $S(O)_2R^{b52}$; and each $R^{b52}$ is independently selected from H and $C_{1-6}$ alkyl.

In some embodiments:

$R^1$ is selected from H and $C_{1-6}$ alkyl;

$R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-

$C_{1-6}$ alkyl-, wherein the $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H and $C_{1-6}$ alkyl;

$R^{3'}$ is H;

$R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from chloro, fluoro, methyl, hydroxy, methoxy, cyano, C(O)OH, morpholinyl, piperazinyl, cyclopropyl, phenyl, pyrazolyl, $C(O)NH_2$, $C(O)N(CH_3)_2$, $C(O)NH_2$-(cyclopropylmethyl), $C(O)NHCH_2CH_3$, $C(O)NHCH_2CH_2OH$, $NHC(O)CH_3$, $SO_2CH_3$, $SO_2CH_2CH_3$, $SO_2NHCH_3$, $SO_2N(CH_3)_2$, $SO_2$-isopropyl, $SO_2$-cyclopropyl, and $SO_2$-morpholinyl, wherein the methyl, morpholinyl, piperazinyl, cyclopropyl, phenyl, pyrazolyl, $C(O)NH_2$-(cyclopropylmethyl), $SO_2$-isopropyl, $SO_2$-cyclopropyl, and $SO_2$-morpholinyl of $R^{4A}$ are each optionally substituted with 1 or 2 substituents independently selected from methyl, hydroxy, cyano, dimethylamino, $C(O)CH_3$, $NHC(O)CH_3$, $C(O)NHCH_3$, and $CH(CH_3)C(O)NH_2$;

$R^5$ is selected from H, halo, $C_{3-6}$ cycloalkyl, and phenyl, wherein the phenyl is optionally substituted by 1 or 2 independently selected $R^{5A}$ substituents;

each $R^{5A}$ is piperidinylmethyl, which is optionally substituted by 1 or 2 independently selected $R^{5B}$ groups;

each $R^{5B}$ is $S(O)_2R^{b52}$; and each $R^{b52}$ is independently selected from H and $C_{1-6}$ alkyl.

In some embodiments:

$R^1$ is selected from H and $C_{1-6}$ alkyl;

$R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H and $C_{1-6}$ alkyl;

$R^{3'}$ is H;

$R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from chloro, fluoro, methyl, hydroxy, methoxy, cyano, C(O)OH, morpholinyl, piperazinyl, cyclopropyl, phenyl, pyrazolyl, $C(O)NH_2$, $C(O)N(CH_3)_2$, $C(O)NH_2$-(cyclopropylmethyl), $C(O)NHCH_2CH_3$, $C(O)NHCH_2CH_2OH$, $NHC(O)CH_3$, $SO_2CH_3$, $SO_2CH_2CH_3$, $SO_2NHCH_3$, $SO_2N(CH_3)_2$, $SO_2$-isopropyl, $SO_2$-cyclopropyl, and $SO_2$-morpholinyl, wherein the methyl, morpholinyl, piperazinyl, cyclopropyl, phenyl, pyrazolyl, $C(O)NH_2$-(cyclopropylmethyl), $SO_2$-isopropyl, $SO_2$-cyclopropyl, and $SO_2$-morpholinyl of $R^{4A}$ are each optionally substituted with 1 or 2 substituents independently selected from methyl, hydroxy, cyano, dimethylamino, $C(O)CH_3$, $NHC(O)CH_3$, $C(O)NHCH_3$, and $CH(CH_3)C(O)NH_2$;

$R^5$ is selected from H, halo, and phenyl which is optionally substituted by 1 or 2 independently selected $R^{5A}$ substituents;

each $R^{5A}$ is piperidinylmethyl, which is optionally substituted by 1 or 2 independently selected $R^{5B}$ groups;

each $R^{5B}$ is $S(O)_2R^{b52}$; and each $R^{b52}$ is independently selected from H and $C_{1-6}$ alkyl.

In some embodiments, the compound of Formula I is a compound of Formula II:

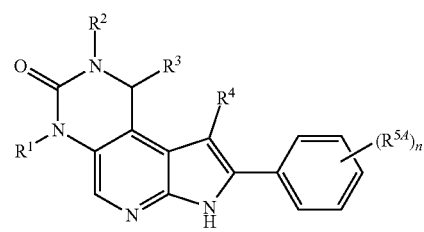

or a pharmaceutically acceptable salt thereof, wherein n is 0, 1, 2, 3, or 4; and variables $R^1$, $R^2$, $R^3$, $R^4$, and $R^{5A}$ are defined according to the definitions provided herein.

In some embodiments, the compound of Formula I is a compound of Formula III:

III

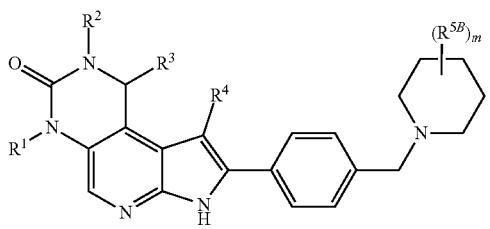

or a pharmaceutically acceptable salt thereof, wherein m is 0, 1, 2, 3, or 4; and variables $R^1$, $R^2$, $R^3$, $R^4$, and $R^{5B}$ are defined according to the definitions provided herein.

In some embodiments, the compound of Formula I is a compound of Formula IV:

IV

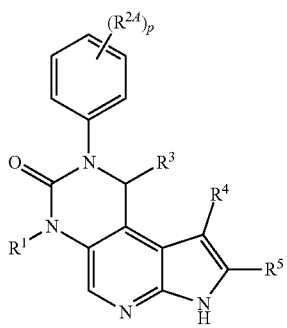

or a pharmaceutically acceptable salt thereof, wherein p is 0, 1, 2, 3, or 4; and variables $R^1$, $R^{2A}$, $R^3$, $R^4$, and $R^5$ are defined according to the definitions provided herein.

In some embodiments, the compound of Formula I is a compound of Formula V:

V

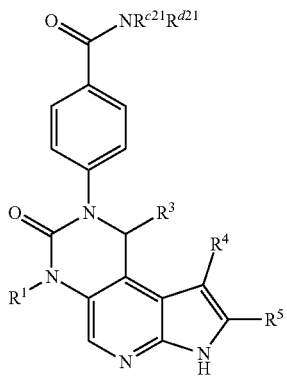

or a pharmaceutically acceptable salt thereof, wherein variables $R^1$, $R^{c21}$, $R^{d21}$, $R^3$, $R^4$, and $R^5$ are defined according to the definitions provided herein.

In some embodiments, the compound of Formula I is a compound of Formula VI:

VI

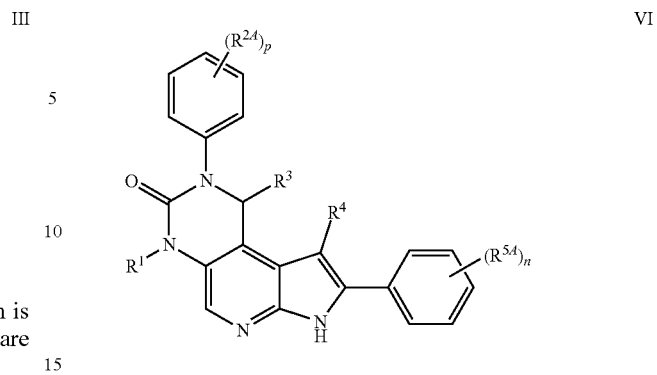

or a pharmaceutically acceptable salt thereof, wherein:
n is 0, 1, 2, 3, or 4;
p is 0, 1, 2, 3, or 4; and
variables $R^1$, $R^{2A}$, $R^3$, $R^4$, and $R^{5A}$ are defined according to the definitions provided herein.

In some embodiments, the compound of Formula I is a compound of Formula VII:

VII

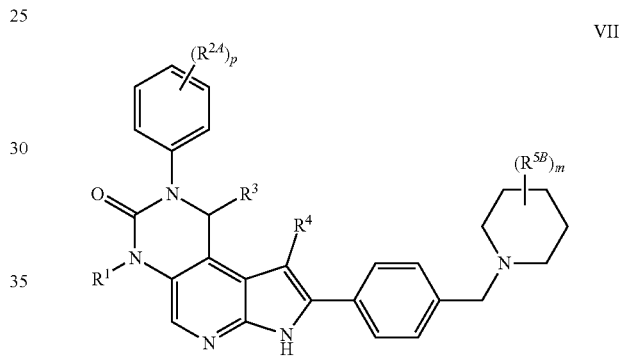

or a pharmaceutically acceptable salt thereof, wherein:
m is 0, 1, 2, 3, or 4;
p is 0, 1, 2, 3, or 4; and
variables $R^1$, $R^{2A}$, $R^3$, $R^4$, and $R^{5B}$ are defined according to the definitions provided herein.

In some embodiments, the compound provided herein is selected from:
4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;
4-methyl-8-(4-((4-(methylsulfonyl)piperidin-1-yl)methyl)phenyl)-2-phenyl-1,2,4,7-tetrahydro-3H-pyrrolo[3',2':5,6]pyrido[3,4-d]pyrimidin-3-one;
4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;
8-(4-((4-(methylsulfonyl)piperidin-1-yl)methyl)phenyl)-2-(pyridin-3-ylmethyl)-1,2,4,7-tetrahydro-3H-pyrrolo[3',2':5,6]pyrido[3,4-d]pyrimidin-3-one;
2-cyclohexyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;
4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)cyclohexane-1-carboxylic acid;
4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)piperidine-1-sulfonamide;

2-(4-((2-methoxyethyl)amino)phenyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;

2-cyano-N-(4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)phenyl)acetamide;

4-(1,4-dimethyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-(pyridin-3-yl)benzamide;

4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-methylbenzamide;

N-(2-(2-benzylhydrazineyl)-2-oxoethyl)-4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzamide;

4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-((1-cyanocyclopropyl)methyl)benzamide;

4-(9-(methoxycarbonyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

N-(4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzyl)acetamide;

4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-methylbenzenesulfonamide;

9-(4-(4-acetylpiperazin-1-yl)phenyl)-2-(tert-butyl)-4-methyl-8-(4-((4-(methylsulfonyl)piperidin-1-yl)methyl)phenyl)-1,2,4,7-tetrahydro-3H-pyrrolo[3',2': 5,6]pyrido[3,4-d]pyrimidin-3-one;

2-(4-(4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)phenyl)-1H-pyrazol-1-yl)propanamide;

4-(9-(1-acetyl-1,2,3,6-tetrahydropyridin-4-yl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-(4-(1-aminocyclopropyl)phenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(4-methyl-9-(1-methyl-1H-pyrrol-3-yl)-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-cyclopropyl-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-cyano-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid; and 4-(8-cyclopropyl-9-(4-methoxyphenyl)-4-methyl-3-oxo-1,3,4,7-tetrahydro-2H-pyrrolo[3',2':5,6]pyrido[3,4-d]pyrimidin-2-yl)benzoic acid;

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the terms "$C_{n-m}$" and "$C_{m-n}$" indicates a range which includes the endpoints, wherein n and m are integers and indicate the number of carbons. Examples include $C_{1-3}$, $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 5 to 10 carbon atoms. In some embodiments, the aryl group is phenyl or naphthyl.

In some embodiments, the aryl is phenyl.

As used herein, "halo" refers to F, Cl, Br, or I. In some embodiments, a halo is F, Cl, or Br. In some embodiments, a halo is F or Cl. In some embodiments, a halo is F. In some embodiments, a halo is Cl.

As used herein, "$C_{n-m}$ haloalkoxy" refers to a group of formula —O-haloalkyl having n to m carbon atoms. Example haloalkoxy groups include OCF$_3$ and OCHF$_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include CF$_3$, C$_2$F$_5$, CHF$_2$, CH$_2$F, CCl$_3$, CHCl$_2$, C$_2$Cl$_5$ and the like.

As used herein, the term "thio" refers to a group of formula —SH.

As used herein, the term "carbonyl", employed alone or in combination with other terms, refers to a —C(O)— group.

As used herein, the term "cyano-C$_{1-n}$ alkyl" refers to a group of formula —(C$_{1-n}$ alkylene)-CN, wherein the alkyl group has 1 to n carbon atoms. In some embodiments, the alkyl group has 1 to 6, 1 to 4, or 1 to 3 carbon atoms, e.g., —(C$_{1-3}$ alkylene)-CN.

As used herein, the term "HO—C$_{1-n}$ alkyl" refers to a group of formula —(C$_{1-n}$ alkylene)-OH, wherein the alkyl group has 1 to n carbon atoms. In some embodiments, the alkyl group has 1 to 6, 1 to 4, or 1 to 3 carbon atoms, e.g., —(C$_{1-3}$ alkylene)-OH.

As used herein, the term "C$_{1-n}$ alkoxy-C$_{1-n}$ alkyl" refers to a group of formula —(C$_{1-n}$ alkylene)-O(C$_{1-n}$ alkyl), wherein the alkyl group has 1 to n carbon atoms. In some embodiments, the alkyl group has 1 to 6, 1 to 4, or 1 to 3 carbon atoms, e.g., —(C$_{1-6}$ alkylene)-O(C$_{1-6}$ alkyl).

As used herein, the term "carboxy" refers to a group of formula —C(O)OH.

As used herein, "cycloalkyl" refers to non-aromatic cyclic hydrocarbons including cyclized alkyl and alkenyl groups. Cycloalkyl groups can include mono- or polycyclic (e.g., having 2 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons (i.e., C$_{3-10}$). In some embodiments, the cycloalkyl is a C$_{3-10}$ monocyclic or bicyclic cycloalkyl. In some embodiments, the cycloalkyl is a C$_{3-7}$ monocyclic cycloalkyl.

In some embodiments, the cycloalkyl is a C$_{4-7}$ monocyclic cycloalkyl. In some embodiments, the cycloalkyl is a C$_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo[2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S, and B. In some embodiments, the heteroaryl is a 5-6 monocyclic heteroaryl having 1 or 2 heteroatom ring members independently selected from N, O, and S. In some embodiments, the heteroaryl group contains 3 to 10, 4 to 10, 5 to 10, 5 to 7, 3 to 7, or 5 to 6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom.

When the heteroaryl group contains more than one heteroatom ring member, the heteroatoms may be the same or different. Example heteroaryl groups include, but are not limited to, thienyl (or thiophenyl), furyl (or furanyl), pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine, pyridinyl, pyrimidinyl, pyrazinyl, pyridazinyl, azolyl, triazolyl, thiadiazolyl, quinolinyl, isoquinolinyl, indolyl, benzothiophenyl, benzofuranyl, benzisoxazolyl, imidazo[1,2-b]thiazolyl, purinyl, triazinyl, thieno[3,2-b]pyridinyl, imidazo[1,2-a]pyridinyl, 1,5-naphthyridinyl, 1H-pyrazolo[4,3-b]pyridinyl, triazolo[4,3-a]pyridinyl, 1H-pyrrolo[3,2-b]pyridinyl, 1H-pyrrolo[2,3-b]pyridinyl, pyrazolo[1,5-a]pyridinyl, indazolyl, and the like.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S, and B, and wherein the ring-forming carbon atoms and heteroatoms of a heterocycloalkyl group can be optionally substituted by one or more oxo or sulfido (e.g., C(O), S(O), C(S), or S(O)$_2$, etc.). When a ring-forming carbon atom or heteroatom of a heterocycloalkyl group is optionally substituted by one or more oxo or sulfide, the O or S of said group is in addition to the number of ring-forming atoms specified herein (e.g., a 1-methyl-6-oxo-1,6-dihydropyridazin-3-yl is a 6-membered heterocycloalkyl group, wherein a ring-forming carbon atom is substituted with an oxo group, and wherein the 6-membered heterocycloalkyl group is further substituted with a methyl group). Heterocycloalkyl groups include monocyclic and polycyclic (e.g., having 2 fused rings) systems. Included in heterocycloalkyl are monocyclic and polycyclic 3 to 10, 4 to 10, 5 to 10, 4 to 7, 5 to 7, or 5 to 6 membered heterocycloalkyl groups. Heterocycloalkyl groups can also include spirocycles and bridged rings (e.g., a 5 to 10 membered bridged biheterocycloalkyl ring having one or more of the ring-forming carbon atoms replaced by a heteroatom independently selected from N, O, S, and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds.

Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring.

In some embodiments, the heterocycloalkyl group contains 3 to 10 ring-forming atoms, 4 to 10 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, S, and B and having one or more oxidized ring members. In some embodiments, the heterocycloalkyl is a monocyclic or bicyclic 5 to 10 membered heterocycloalkyl having 1, 2, 3, or 4 heteroatoms independently selected from N, O, and S and having one or more oxidized ring members. In some embodiments, the heterocycloalkyl is a monocyclic 5 to 6 membered heterocycloalkyl having 1, 2, 3, or 4 heteroatoms independently selected from N, O, and S and having one or more oxidized ring members.

Example heterocycloalkyl groups include pyrrolidin-2-one (or 2-oxopyrrolidinyl), 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, 1,2,3,4-tetrahydroisoquinoline, benzazapene, azabicyclo[3.1.0]hexanyl, diazabicyclo[3.1.0]hexanyl, oxobicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxobicyclo[2.2.2]octanyl, azabicyclo[2.2.2]octanyl, azaadamantanyl, diazaadamantanyl, oxoadamantanyl, azaspiro[3.3]heptanyl, diazaspiro[3.3]heptanyl, oxo-azaspiro[3.3]heptanyl, azaspiro[3.4]octanyl, diazaspiro[3.4]octanyl, oxo-azaspiro[3.4]octanyl, azaspiro[2.5]octanyl, diazaspiro[2.5]octanyl, azaspiro[4.4]nonanyl, diazaspiro[4.4]nonanyl, oxo-azaspiro[4.4]nonanyl, azaspiro[4.5]decanyl, diazaspiro[4.5]decanyl, diazaspiro[4.4]nonanyl, oxo-diazaspiro[4.4]nonanyl, oxo-dihydropyridazinyl, oxo-2,6-diazaspiro[3.4]octanyl, oxohexahydropyrrolo[1,2-a]pyrazinyl, 3-oxopiperazinyl, oxo-pyrrolidinyl, oxo-pyridinyl and the like.

As used herein, "C$_{o-p}$ cycloalkyl-C$_{n-m}$ alkyl-" refers to a group of formula cycloalkyl-alkylene-, wherein the cycloalkyl has o to p carbon atoms and the alkylene linking group has n to m carbon atoms.

As used herein "C$_{o-p}$ aryl-C$_{n-m}$ alkyl-" refers to a group of formula aryl-alkylene-, wherein the aryl has o to p carbon atoms and the alkylene linking group has n to m carbon atoms.

As used herein, "heteroaryl-C$_{n-m}$ alkyl-" refers to a group of formula heteroaryl-alkylene-, wherein alkylene linking group has n to m carbon atoms.

As used herein "heterocycloalkyl-C$_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "C$_{o-p}$ cycloalkyl-C$_{n-m}$ alkyl-", "C$_{o-p}$ aryl-C$_{n-m}$ alkyl-", "phenyl-C$_{n-m}$ alkyl-", "heteroaryl-C$_{n-m}$ alkyl-", and "heterocycloalkyl-C$_{n-m}$ alkyl-" contain alkyl linking groups. Examples of "alkyl linking groups" or "alkylene groups" include methylene, ethan-1,1-diyl, ethan-1,2-diyl, propan-1,3-dilyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl, or sulfonyl group.

As used herein, the term "independently selected from" means that each occurrence of a variable or substituent (e.g., each $R^M$), are independently selected at each occurrence from the applicable list.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration. The Formulas (e.g., Formula I, Formula Ia, etc.) provided herein include stereoisomers of the compounds.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H- 1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated by those skilled in the art, the compounds provided herein, including salts and stereoisomers thereof, can be prepared using known organic synthesis techniques and can be synthesized according to any of numerous possible synthetic routes.

Compounds of Formula I can be prepared, for example, according to the procedures described in in Scheme 1. For example, 4-chloro-5-nitro-1H-pyrrolo[2,3-b]pyridine with a suitable protecting group (e.g., benzenesulfonyl group) (compound 1-1) can be treated with lithium diisopropyl amide solution and suitable bromination reagent (e.g. dibromotetrachloroethane) to generate compound 1-2. Compound 1-3 can be prepared by metal-catalyzed cross coupling reactions (e.g., Suzuki coupling) of compound 1-2 in the presence of a palladium catalyst (e.g. [1,1'-bis(diphenylphosphino)ferrocene]dichloropalladium(II)) and a base (e.g. cesium carbonate or potassium phosphate, tribasic). Compound 1-4 can be prepared by metal-catalyzed cross coupling reactions (e.g., Suzuki coupling) of compound 1-3 with vinylboronic acid in the presence of a palladium catalyst (e.g. [1,1'-bis(diphenylphosphino)ferrocene]dichloropalladium(II)) and a base (e.g. cesium carbonate or potassium phosphate, tribasic). Compound 1-5 can be prepared by oxidative cleavage conditions (e.g., potassium osmate dihydrate in the presence of sodium periodate). Compound 1-6 can be prepared by reductive amination of compound 1-5 with 4-methoxybenzylamine in the presence of acid (e.g., acetic acid) and reducing agent (e.g., sodium cyanoborohydride). Compound 1-6 can be converted to compound 1-7 using reduction conditions (e.g., iron in combination with ammonium chloride). Compound 1-8 can be prepared by reacting compound 1-7 with coupling reagents (e.g., CDI or triphosgene). Compound 1-9 can be prepared by treating compound 1-8 with suitable base (e.g. sodium hydride) and methylation reagent (e.g., iodomethane). Treating compound 1-9 with strong acid (e.g., TFA) affords compound 1-10. Compound 1-11 can be prepared by metal-catalyzed cross coupling reactions (e.g., Buchwald coupling) of compound 1-10 with aryl bromide in the presence of a palladium catalyst (e.g. chloro(2-dicyclohexylphosphino-2',4',6'-triisopropyl-1,1'-biphenyl)[2-(2'-amino-1,1'-biphenyl)]palladium (II)) and suitable base (e.g. cesium carbonate). Compounds of Formula I (e.g., compound 1-A of Scheme 1) can be prepared by treating compound 1-11 in suitable deprotection conditions (e.g. when benzene sulfonyl was used as protecting group, sodium hydroxide was used with water and methanol as co-solvent).

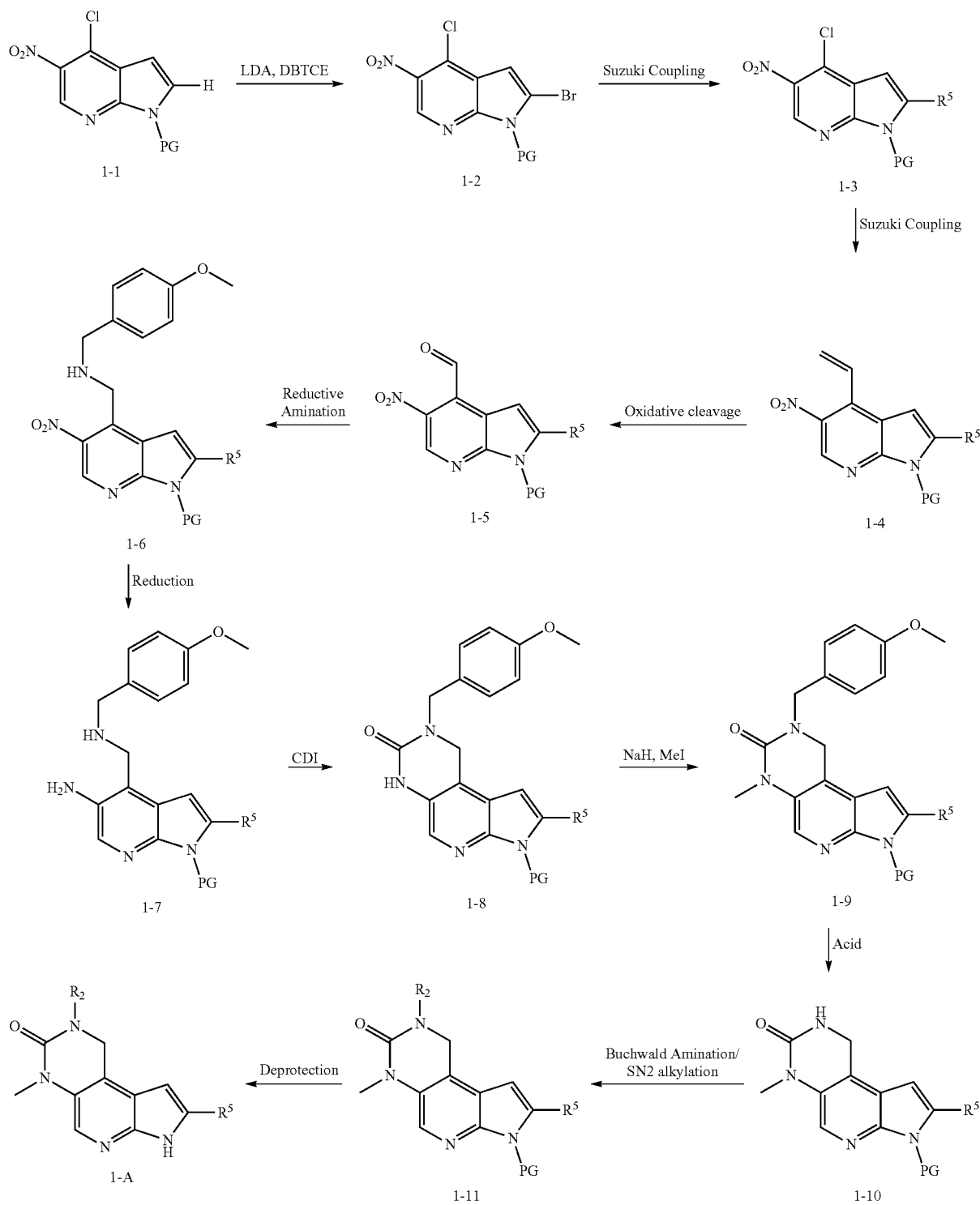

Scheme 1

Compounds of Formula I can also be prepared, for example, according to the procedures described in Scheme 2. Compound 2-1 can be prepared by reductive amination of compound 1-5 (see Scheme 1) with suitable amines in the presence of acid (e.g., acetic acid) and reducing agent (e.g. sodium cyanoborohydride). Compound 2-1 can be converted to compound 2-2 using reduction conditions (e.g., iron in combination with ammonium chloride). Compound 2-3 can be prepared by reacting compound 2-2 with coupling reagents (e.g., CDI or triphosgene). Compound 2-4 can be prepared by treating compound 2-3 with suitable base (e.g. sodium hydride) and methylation reagent (e.g., iodomethane). The compound of Formula I (e.g., compound 2-A of Scheme 2) can be prepared by treating compound 2-4 in suitable deprotection conditions (e.g. when benzene sulfonyl was used as protecting group, sodium hydroxide was used with water and methanol as co-solvent).

with tributyl(1-ethoxyvinyl)tin in the presence of a palladium catalyst (e.g., bis(triphenylphosphine)palladium(II) dichloride). The resulting intermediate can be converted to compound 3-1 by treating with acid (e.g., in one pot). Compound 3-2 can be prepared by reductive amination of compound 3-1 with suitable amines using acids (e.g. titanium(IV) chloride) and reducing agent (e.g. sodium cyanoborohydride). Compound 3-2 can be converted to compound 3-3 using reduction conditions (e.g., iron in combination with ammonium chloride). Compound 3-4 can be prepared by reacting compound 3-3 with coupling reagents (e.g., CDI or triphosgene). Compound 3-5 can be prepared by treating compound 3-4 with suitable base (e.g. sodium hydride) and methylation reagent (e.g., iodomethane). The compound of Formula I (e.g., compound 3-A of Scheme 3) can be

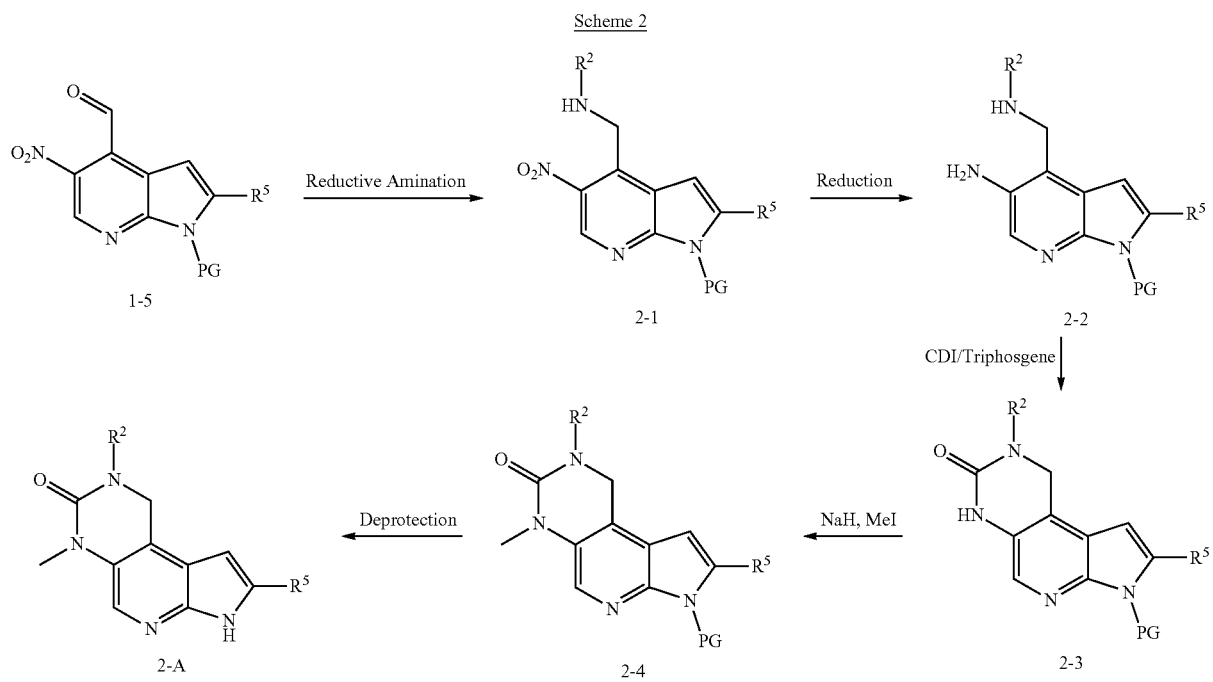

Compounds of Formula I can also be prepared, for example, according to the procedures described in Scheme 3. Compound 3-1 can be prepared by metal-catalyzed cross coupling reactions (e.g., Stille coupling) of compound 1-3 prepared by treating compound 3-5 in suitable deprotection conditions (e.g. when benzene sulfonyl was used as protecting group, sodium hydroxide was used with water and methanol as co-solvent).

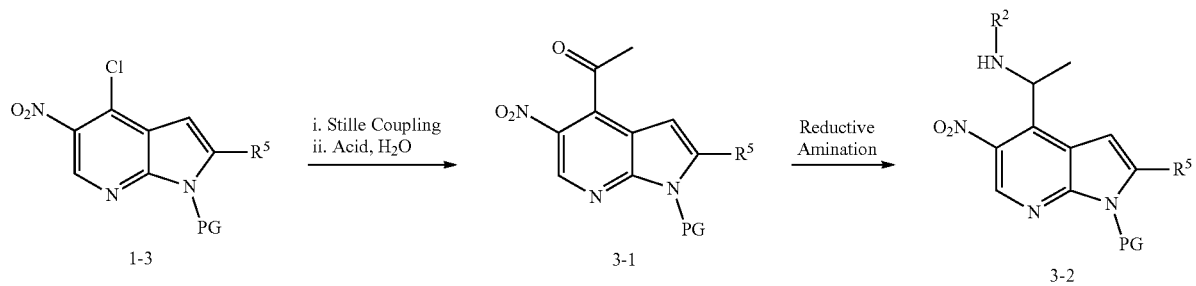

-continued

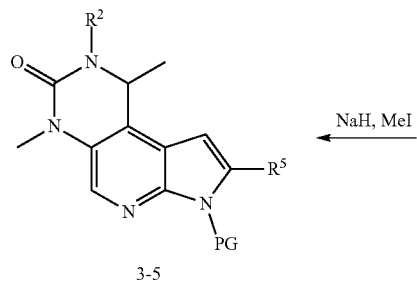 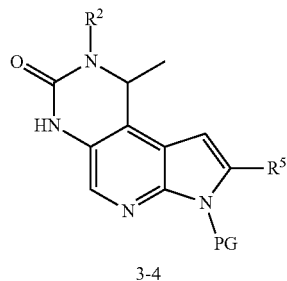 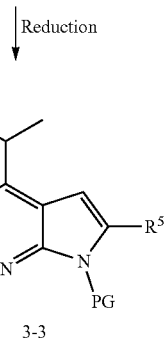

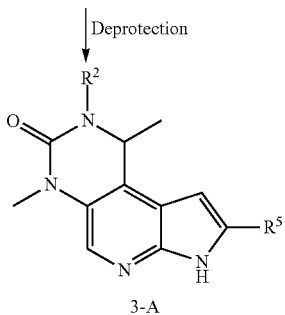

Compounds of Formula I can also be prepared, for example, according to the procedures described in Scheme 4. Compound 4-1 can be prepared by reductive amination of compound 1-5 (see Scheme 1) with t-butylamine in the presence of acid (e.g., acetic acid) and reducing agent (e.g. sodium cyanoborohydride). Compound 4-1 can be converted to compound 4-2 using reduction conditions (e.g., iron in combination with ammonium chloride). Compound 4-3 can be prepared by reacting compound 4-2 with coupling reagents (e.g., CDI or triphosgene). Compound 4-4 can be prepared by treating compound 4-3 with suitable base (e.g. sodium hydride) and methylation reagent (e.g., iodomethane). Treating compound 4-4 with strong acid (e.g., TFA) would afford desired compound 4-5. Compound 4-6 can be prepared by metal-catalyzed cross coupling reactions (e.g., Buchwald coupling) of compound 4-5 with aryl bromide in the presence of a palladium catalyst (e.g. chloro(2-dicyclohexylphosphino-2',4',6'-triisopropyl-1,1'-biphenyl)[2-(2'-amino-1,1'-biphenyl)]palladium(II)) and suitable base (e.g. cesium carbonate). The compound of Formula I (e.g., compound 4-A of Scheme 4) can be prepared by treating compound 4-6 in suitable deprotection conditions (e.g. when benzene sulfonyl was used as protecting group, sodium hydroxide was used with water and methanol as co-solvent).

Scheme 4

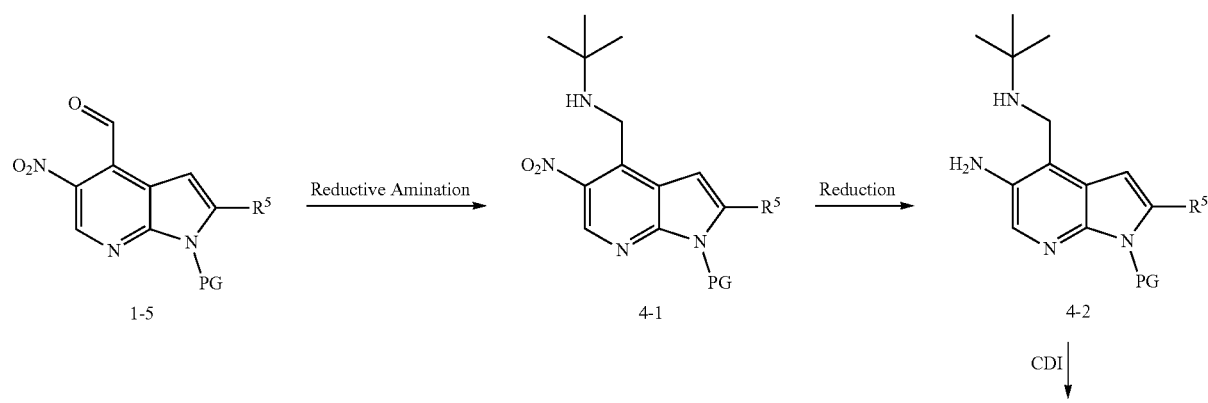

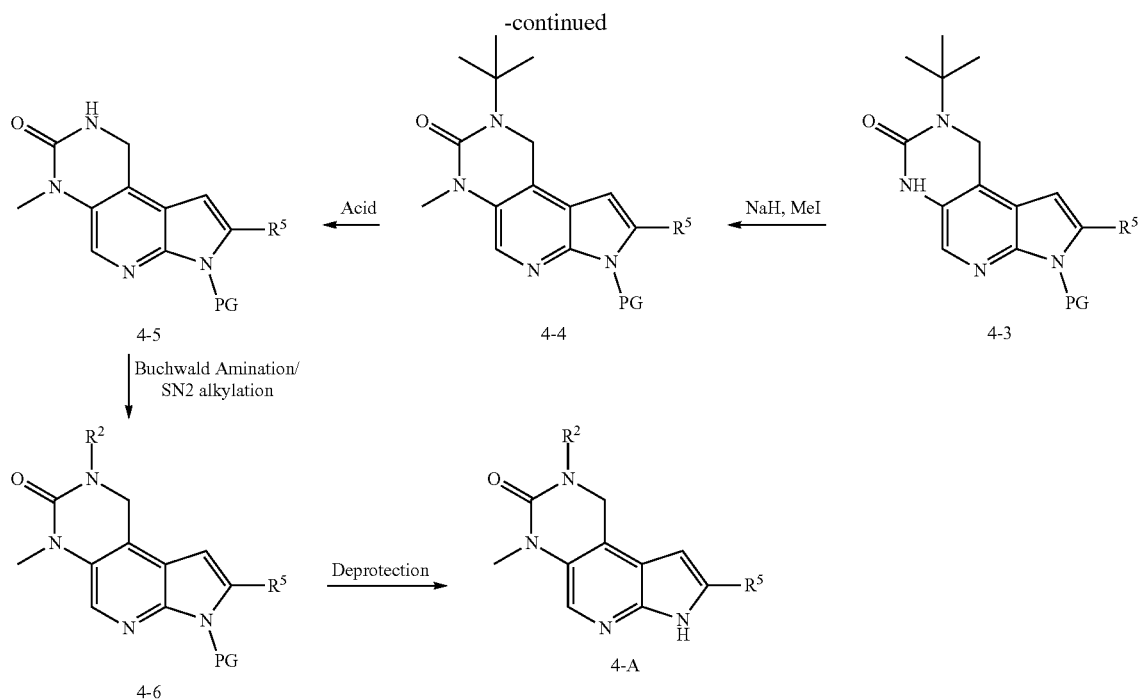

Compounds of Formula I can also be prepared, for example, according to the procedures described in Scheme 5. For example, 4-chloro-5-nitro-1H-pyrrolo[2,3-b]pyridine with a suitable protecting group (e.g., benzenesulfonyl group) (see compound 1-1, Scheme 1) can be used as starting material. Compound 5-1 can be prepared by metal-catalyzed cross coupling reactions (e.g., Suzuki coupling) of compound 1-1 with vinylboronic acid in the presence of a palladium catalyst (e.g. [1,1'-bis(diphenylphosphino)ferrocene]dichloropalladium(II)) and a base (e.g. cesium carbonate or potassium phosphate, tribasic). Compound 5-2 can be prepared by oxidative cleavage conditions (e.g., potassium osmate dihydrate in the presence of sodium periodate). Compound 5-3 can be prepared by reductive amination of compound 5-2 with suitable amines in the presence of acid (e.g., acetic acid) and reducing agent (e.g. sodium cyanoborohydride). Compound 5-3 can be converted to compound 5-4 using reduction conditions (e.g., iron in combination with ammonium chloride). Compound 5-5 can be prepared by reacting compound 5-4 with coupling reagents (e.g., CDI or triphosgene).

Compound 5-6 can be prepared by treating compound 5-5 with suitable base (e.g. sodium hydride) and methylation reagent (e.g., iodomethane). Compound 5-6 can be treated with lithium diisopropyl amide solution and suitable bromination reagent (e.g. dibromotetrachloroethane) to generate desired compound 5-7. Compound 5-8 can be prepared by metal-catalyzed cross coupling reactions (e.g., Suzuki coupling) of compound 5-7 in the presence of a palladium catalyst (e.g. [1,1'-bis(diphenylphosphino)ferrocene]dichloropalladium(II)) and a base (e.g. cesium carbonate or potassium phosphate, tribasic). Treating compound 5-8 with strong acid (e.g., TFA) would afford the desired compound 5-9. Compound 5-10 can be prepared by metal-catalyzed cross coupling reactions (e.g., Buchwald coupling) of compound 5-9 with aryl bromide in the presence of a palladium catalyst (e.g., chloro(2-dicyclohexylphosphino-2',4',6'-triisopropyl-1,1'-biphenyl)[2-(2'-amino-1,1'-biphenyl)]palladium(II)) and suitable base (e.g. cesium carbonate). The compound of Formula I (e.g., compound 5-A of Scheme 5) can be prepared by treating compound 5-10 in suitable deprotection conditions (e.g. when benzene sulfonyl was used as protecting group, sodium hydroxide was used with water and methanol as co-solvent).

Scheme 5

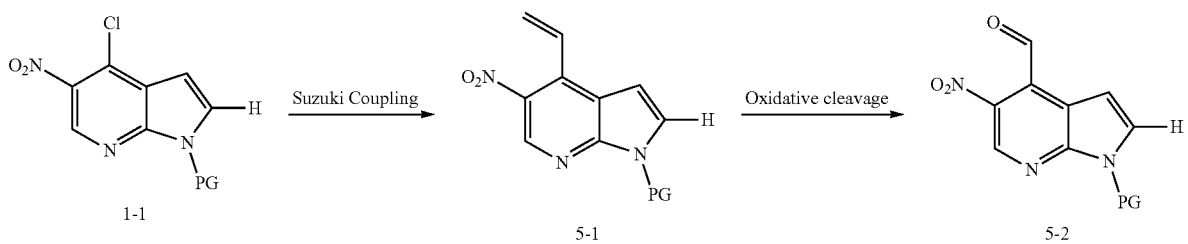

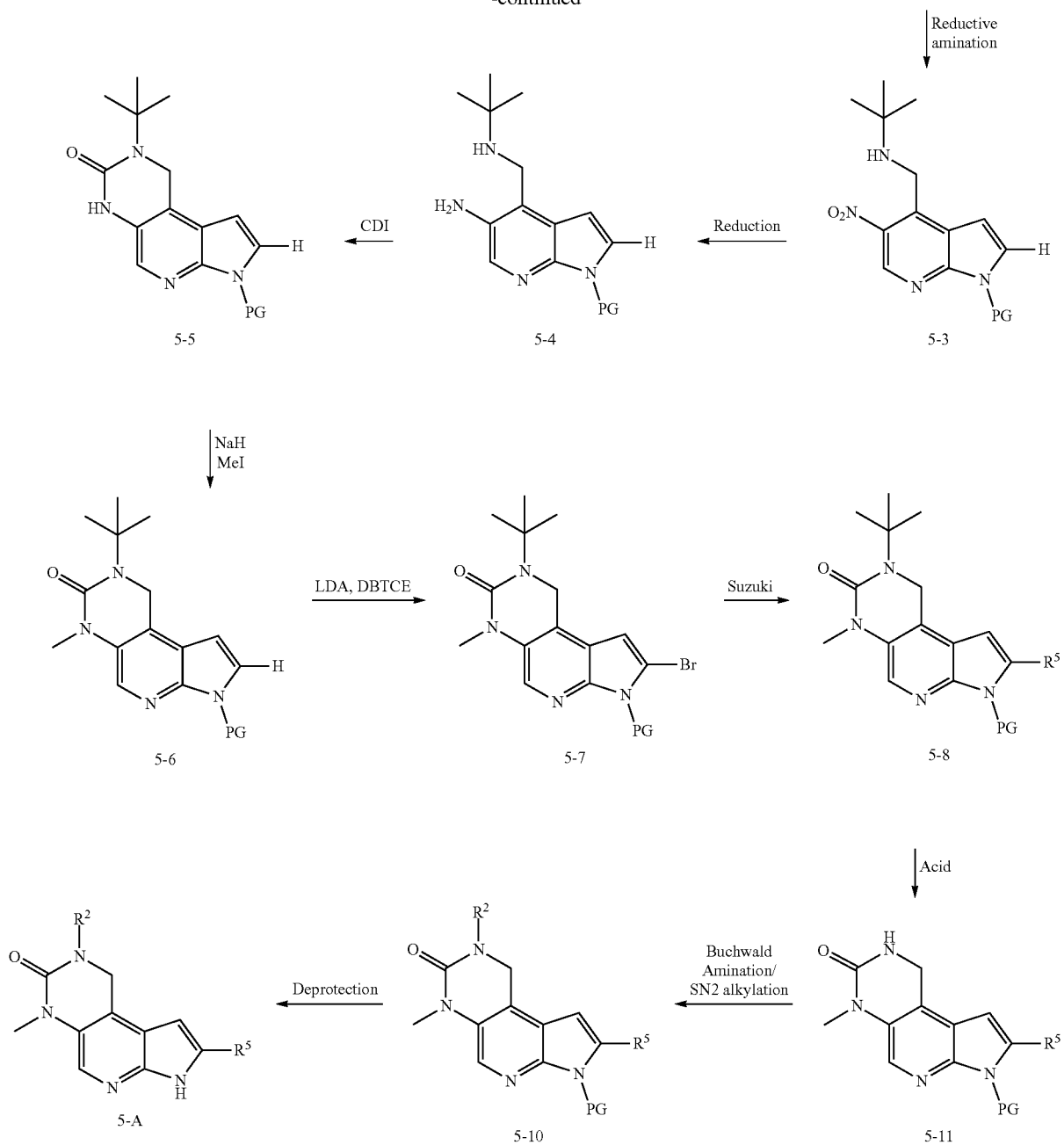

Compounds of Formula I can also be prepared, for example, according to the procedures described in Scheme 6. Compounds 1-9 (see Scheme 1) or 5-8 (see Scheme 5) can be deprotected under suitable conditions (e.g. when benzene sulfonyl was used as protecting group, sodium hydroxide was used with water and methanol as co-solvent) to afford compound 6-1. Compound 6-1 can be halogenated with a halogenating reagent (e.g., NBS or NIS), to afford compound 6-2. Compound 6-2 can be protected (e.g., with (Boc)$_2$O), to afford compound 6-3. Compound 6-4 can be prepared by metal-catalyzed cross coupling reactions (e.g., Suzuki coupling) of compound 6-3 in the presence of a palladium catalyst (e.g., [1,1'-bis(diphenylphosphino)ferrocene]dichloropalladium(II)) and a base (e.g., cesium carbonate or potassium phosphate, tribasic). Alternatively, compound 6-4 can be prepared by other metal-catalyzed cross coupling reactions (e.g., Negishi coupling) of compound 6-3 in the presence of a palladium catalyst (e.g. tetrakis(triphenylphospine)palladium(0)). Compound 6-4 can also be prepared through a sulfonylation of compound 6-3 with a sodium alkylsulfinate in the presence of Cu(I) (e.g. copper(I) iodide) or a carbonylation of compound 6-3 with carbon monoxide in the presence of a palladium catalyst (e.g. [1,1'-bis(diphenylphosphino)ferrocene]dichloropalladium (II)) and a tertiary amine base. The compound of Formula I (e.g., compound 6-A of Scheme 6) can be prepared by treating compound 6-4 with suitable deprotection conditions such as TFA in dichloromethane.

Scheme 6

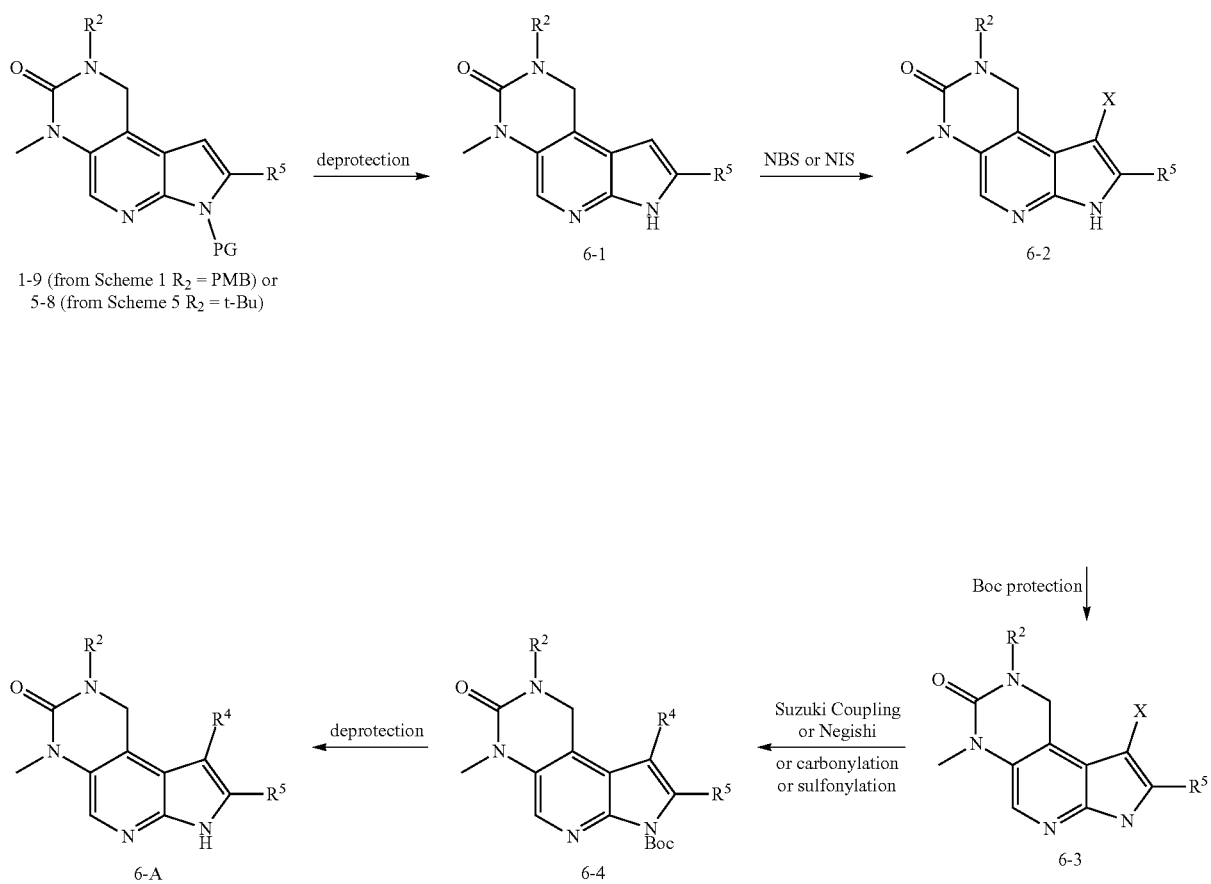

1-9 (from Scheme 1 R₂ = PMB) or
5-8 (from Scheme 5 R₂ = t-Bu)

Compounds of Formula I can also be prepared, for example, according to the procedures described in Scheme 7. Compound 5-2 (see Scheme 5) can be converted to compound 7-1 by reductive amination of compound 5-2 with tert-butyl 4-aminobenzoate in the presence of acid (e.g. acetic acid) and a reducing agent (e.g. sodium cyanoborohydride). Compound 7-1 can be converted to compound 7-2 using reduction conditions (e.g., iron in combination with ammonium chloride). Compound 7-3 can be prepared by reacting compound 7-2 with coupling reagents (e.g., CDI or triphosgene).

Compound 7-4 can be prepared by treating compound 7-3 with suitable base (e.g. cesium carbonate) and methylation reagent (e.g., iodomethane). Compound 7-4 can be treated with lithium diisopropyl amide solution and suitable bromination reagent (e.g. dibromotetrachloroethane) to generate desired compound 7-5. Compound 7-6 can be prepared by metal-catalyzed cross coupling reactions (e.g., Suzuki coupling) of compound 7-5 in the presence of a palladium catalyst (e.g. [1,1'-bis(diphenylphosphino)ferrocene]dichloropalladium(II)) and a base (e.g. cesium carbonate or potassium phosphate, tribasic). Compound 7-7 can be prepared by treating compound 7-6 in suitable deprotection conditions (e.g. when benzene sulfonyl was used as protecting group, sodium hydroxide was used with water and methanol as co-solvent).

Compound 7-7 can be halogenated with a halogenating reagent (e.g., NBS or NIS), to afford compound 7-8. Compound 7-8 can be protected (e.g., with (Boc)₂O), to give compound 7-9. Compound 7-10 can be prepared by metal-catalyzed cross coupling reactions (such as Suzuki coupling) of compound 7-9 in the presence of a palladium catalyst (e.g. [1,1'-bis(diphenylphosphino)ferrocene]dichloropalladium (II)) and a base (e.g. cesium carbonate or potassium phosphate, tribasic). Alternatively, compound 7-10 can be prepared by other metal-catalyzed cross coupling reactions (e.g., Negishi coupling) of compound 7-9 in the presence of a palladium catalyst (e.g. tetrakis(triphenylphospine)palladium(0)). Compound 7-10 can also be prepared through a sulfonylation of compound 7-9 with a sodium alkylsulfinate in the presence of Cu(I) (e.g. copper(I) iodide) or a carbonylation of compound 7-9 with carbon monoxide in the presence of a palladium catalyst (e.g. [1,1'-bis(diphenylphosphino)ferrocene]dichloropalladium(II)) and a tertiary amine base.

Compound 7-11 can be prepared by treating compound 7-10 with suitable deprotection conditions (e.g., TFA in dichloromethane). Carboxylic acid 7-11 can be coupled with an appropriately substituted amine under standard amide formation conditions (e.g., in the presence of a coupling reagent, such as HATU, and amine, such as diisopropylethylamine) or by conversion of acid 7-11 to the acid chloride (e.g., with oxalyl chloride) and condensing with an appropriately substituted amine) to afford the compound of Formula I (e.g., compound 7-A of Scheme 7).

Scheme 7
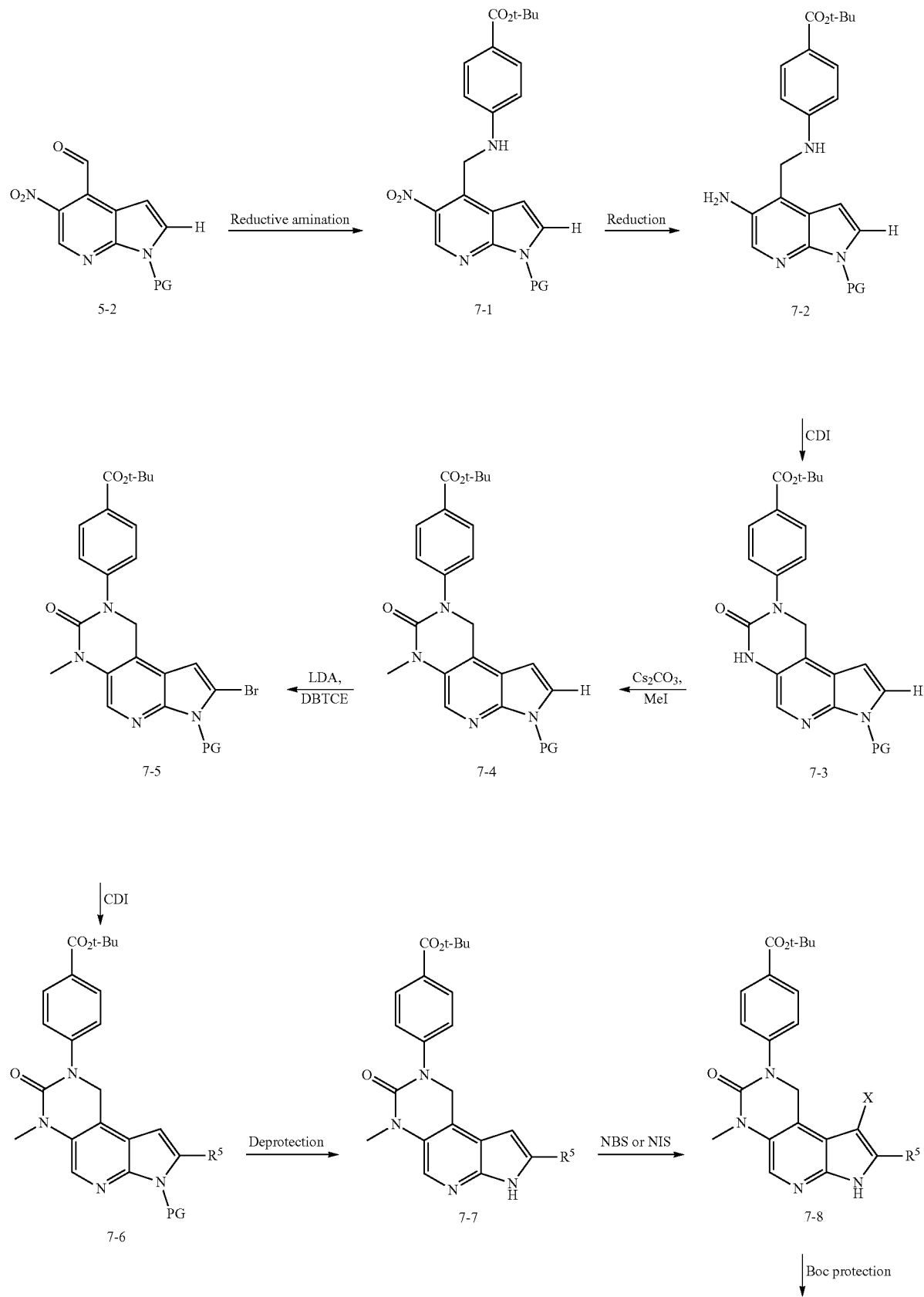

-continued

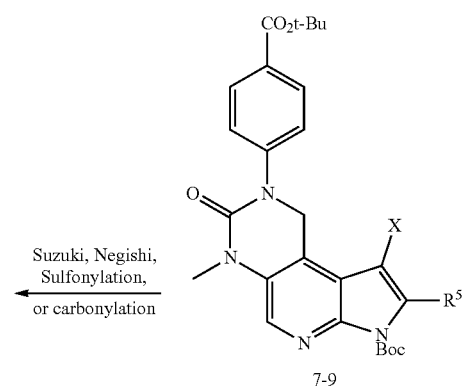

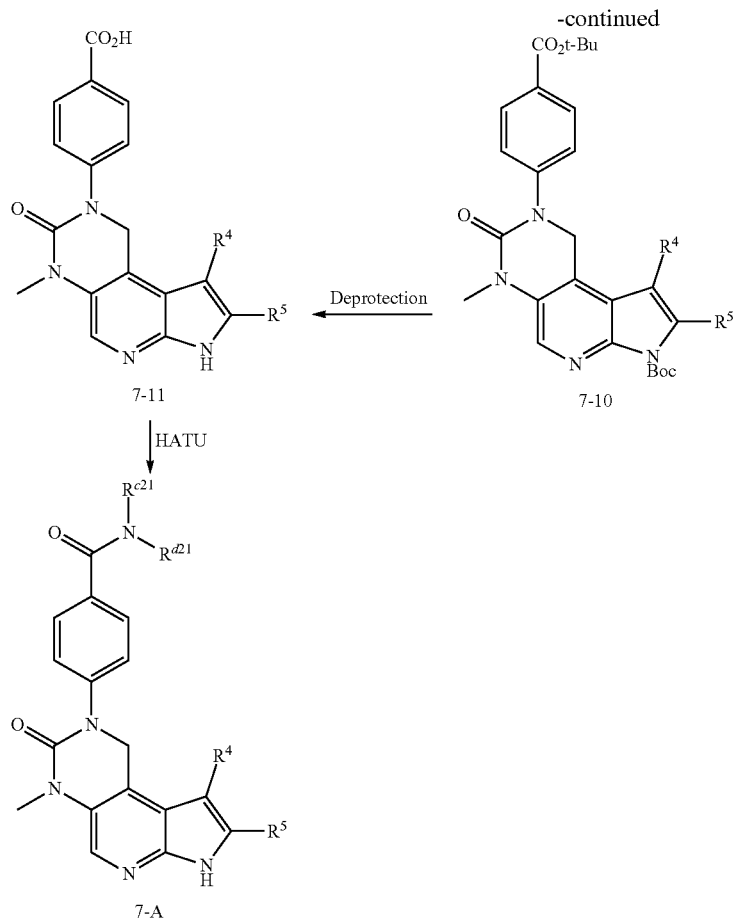

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

The expressions, "ambient temperature" or "room temperature", or "rt" as used herein, are understood in the art, and refer generally to a temperature, e.g., a reaction temperature, that is about the temperature of the room in which the reaction is carried out, for example, a temperature from about 20° C. to about 30° C.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Methods of Use

The compounds described herein can inhibit the activity of the V617F variant of the protein-tyrosine kinase JAK2 (i.e., "V617F" or "JAK2V617F"). Compounds which inhibit V617F are useful in providing a means of preventing the growth or inducing apoptosis in tumors, particularly by inhibiting angiogenesis. It is therefore anticipated that the compounds of the disclosure are useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a V617F-related disorder in a patient in need thereof, comprising the step of administering to said patient a compound of the disclosure, or a pharmaceutically acceptable composition thereof.

Myeloproliferative diseases (MPD) are multipotent hematopoietic stem cell disorders characterized by excess production of various blood cells. MPNs include polycythemia vera (PV), essential thrombocythemia (ET), and idiopathic myelofibrosis (IMF). JAK2 V617F mutation is reported in about 95% of patients with PV, in 35% to 70% of patients with ET, and 50% of patients with IMF. Also, JAK2 exon 12 mutations are detected in some of the V617F-negative PV patients (Ma et al., J. Mol. Diagn., 11: 49-53, 2009). In some embodiments, the compounds of the disclosure can be useful in the treatment of myeloproliferative disorders (e.g., myeloproliferative neoplasms) in a patient in need thereof, such as polycythemia vera, essential thrombocythemia, myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like.

In some embodiments, the myeloproliferative disorder is a myeloproliferative neoplasm.

In some embodiments, the myeloproliferative disorder is myelofibrosis (e.g., primary myelofibrosis (PMF) or post polycythemia vera/essential thrombocythemia myelofibrosis (Post-PV/ET MF)).

In some embodiments, the myeloproliferative disorder is primary myelofibrosis (PMF).

In some embodiments, the myeloproliferative disorder is post- essential thrombocythemia myelofibrosis (Post-ET MF).

In some embodiments, the myeloproliferative disorder is post polycythemia vera myelofibrosis (Post-PV MF).

In some embodiments, the myeloproliferative disorder is selected from primary myelofibrosis (PMF), polycythemia vera (PV), and essential thrombocythemia (ET).

In some embodiments, the myeloproliferative neoplasm is primary myelofibrosis (PMF).

In some embodiments, the myeloproliferative neoplasm is polycythemia vera (PV).

In some embodiments, the myeloproliferative neoplasm is essential thrombocythemia (ET).

Myeloproliferative diseases include disorders of a bone marrow or lymph node-derived cell type, such as a white blood cell. A myeloproliferative disease can manifest by abnormal cell division resulting in an abnormal level of a particular hematological cell population. The abnormal cell division underlying a proliferative hematological disorder is typically inherent in the cells and not a normal physiological response to infection or inflammation. Leukemia is a type of myeloproliferative disease. Exemplary myeloproliferative diseases include, but are not limited to, acute myeloid leukemia (AML), acute lymphoblastic leukemia (ALL), chronic lymphocytic leukemia (CLL), myelodysplastic syndrome (MDS), chronic myeloid leukemia (CML), hairy cell leukemia, leukemic manifestations of lymphomas, multiple myeloma, polycythemia vera (PV), essential thrombocythemia (ET), idiopathic myelofibrosis (IMF), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM), and unclassified myeloproliferative diseases (UMPD or MPD-NC). Lymphoma is a type of proliferative disease that mainly involves lymphoid organs, such as lymph nodes, liver, and spleen. Exemplary proliferative lymphoid disorders include lymphocytic lymphoma (also called chronic lymphocytic leukemia), follicular lymphoma, large cell lymphoma, Burkitt's lymphoma, marginal zone lymphoma, lymphoblastic lymphoma (also called acute lymphoblastic lymphoma).

For example, the compounds of the disclosure are useful in the treatment of cancer. Example cancers include bladder cancer (e.g., urothelial carcinoma, squamous cell carcinoma, adenocarcinoma), breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma (e.g., intrahepatic, hilar or perihilar, distal extrahepatic), liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, acute myeloid leukemia (AML), B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera (PV), essential thrombocythemia (ET), and primary myelofibrosis (PMF)), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of a compound of the disclosure. In certain embodiments, the cancer is selected from T lymphoblastic lymphoma, glioblastoma, melanoma, rhabdosarcoma, lymphosarcoma, and osteosarcoma.

Other cancers treatable with the compounds of the disclosure include tumors of the eye, glioblastoma, melanoma, leiomyosarcoma, and urothelial carcinoma (e.g., ureter, urethra, bladder, urachus).

The compounds of the disclosure can also be useful in the inhibition of tumor metastases.

In some embodiments, the compounds of the disclosure as described herein can be used to treat Alzheimer's disease, HIV, or tuberculosis.

In some embodiments, the compounds of the disclosure can be useful in the treatment of myelodysplastic syndrome (MDS) in a patient in need thereof. In some embodiments, said patient having the myelodysplastic syndrome (MDS) is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br. J. Haematol.* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues.* (ed. 4th edition): Lyon, France: IARC Press; 2008: 88-103).

In some embodiments, the compounds of the disclosure can be useful in the treatment of myeloproliferative disorder/myelodysplastic overlap syndrome (MPD/MDS overlap syndrome).

In some embodiments, the compounds of the disclosure can be useful in the treatment of leukemia.

In some embodiments, the compounds of the disclosure can be useful in the treatment of acute myeloid leukemia (AML).

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

TABLE 1

2008 WHO Classification for De Novo Myelodysplastic Syndrome

| Subtype | Blood | Bone Marrow |
| --- | --- | --- |
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory anemia with ring sideroblasts associated with thrombocytosis (RARS-T).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

The present disclosure further provides a compound described herein, or a pharmaceutically acceptable salt thereof, for use in any of the methods described herein.

The present disclosure further provides use of a compound described herein, or a pharmaceutically acceptable salt thereof, for the preparation of a medicament for use in any of the methods described herein.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a V617F variant with a compound described herein includes the administration of a compound described herein to an individual or patient, such as a human, having a V617F variant, as well as, for example, introducing a compound described herein into a sample containing a cellular or purified preparation containing the V617F variant.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment or prevention of V617F-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD19, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (ruxolitinib, additional JAK1/2 and JAK1-selective, baricitinib or itacitinib), Pim kinase inhibitors (e.g., LGH447, INCB053914 and SGI-1776), PI3 kinase inhibitors including PI3K-delta selective and broad spectrum PI3K inhibitors (e.g., INCB50465 and INCB50797), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibiors (e.g., olaparib or rucaparib), and inhibitors of BTK such as ibrutinib.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is retifanimab (also known as MGA012), nivolumab, pembrolizumab (also known as MK-3475), pidilizumab, SHR-1210, PDR001, ipilimumab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is retifanimab (also known as MGA012). In some embodiments, the anti-PD1 antibody is SHR-1210. Other anticancer agent(s) include antibody therapeutics such as 4-1BB (e.g. urelumab, utomilumab).

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and capmatinib (also known as INC-280). Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with inhibitors described herein. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with compounds described herein. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (e.g., vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin (see e.g., U.S. Pat. Nos. 9,233,985, 10,065,974, 10,287,303, 8,524,867, the disclosures of which are incorporated by reference herein in their entireties).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating V617F in tissue samples, including human, and for identifying V617F inhibitors by binding of a labeled compound. Substitution of one or more of the atoms of the compounds of the present disclosure can also be useful in generating differentiated ADME (Adsorption, Distribution, Metabolism and Excretion.) Accordingly, the present disclosure includes V617F assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, >5S, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I can be optionally substituted with deuterium atoms, such as —$CD_3$ being substituted for —$CH_3$). In some embodiments, alkyl groups of the disclosed Formulas (e.g., Formula I) can be perdeuterated.

One or more constituent atoms of the compounds presented herein can be replaced or substituted with isotopes of the atoms in natural or non-natural abundance. In some embodiments, the compound includes at least one deuterium atom. For example, one or more hydrogen atoms in a compound presented herein can be replaced or substituted by deuterium (e.g., one or more hydrogen atoms of a $C_{1-6}$ alkyl group can be replaced by deuterium atoms, such as —$CD_3$ being substituted for —$CH_3$). In some embodiments, the compound includes two or more deuterium atoms. In some embodiments, the compound includes 1-2, 1-3, 1-4, 1-5, 1-6, 1-8, 1-10, 1-12, 1-14, 1-16, 1-18, or 1-20 deuterium atoms. In some embodiments, all of the hydrogen atoms in a compound can be replaced or substituted by deuterium atoms.

In some embodiments, each hydrogen atom of the compounds provided herein, such as hydrogen atoms attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is optionally replaced by deuterium atoms.

In some embodiments, each hydrogen atom of the compounds provided herein, such as hydrogen atoms to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, is replaced by deuterium atoms (i.e., the alkyl, alkenyl, alkynyl, aryl, phenyl, cycloalkyl, heterocycloalkyl, or heteroaryl substituents, or —$C_{1-4}$ alkyl-, alkylene, alkenylene, and alkynylene linking groups are perdeuterated).

In some embodiments, 1, 2, 3, 4, 5, 6, 7, 8, 9, 10, 11, or 12 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene, and alkynylene linking groups, as described herein, are optionally replaced by deuterium atoms.

In some embodiments, 1, 2, 3, 4, 5, 6, 7, or 8 hydrogen atoms, attached to carbon atoms of alkyl, alkenyl, alkynyl, aryl, phenyl, cycloalkyl, heterocycloalkyl, or heteroaryl substituents or —$C_{1-4}$ alkyl-, alkylene, alkenylene and alkynylene linking groups, as described herein, are optionally replaced by deuterium atoms.

In some embodiments, the compound provided herein (e.g., the compound of any of Formulas I-VII), or a pharmaceutically acceptable salt thereof, comprises at least one deuterium atom.

In some embodiments, the compound provided herein (e.g., the compound of any of Formulas I-VII), or a pharmaceutically acceptable salt thereof, comprises two or more deuterium atoms.

In some embodiments, the compound provided herein (e.g., the compound of any of Formulas I-VII), or a pharmaceutically acceptable salt thereof, comprises three or more deuterium atoms.

In some embodiments, for a compound provided herein (e.g., the compound of any of Formulas I-VII), or a pharmaceutically acceptable salt thereof, all of the hydrogen atoms are replaced by deuterium atoms (i.e., the compound is "perdeuterated").

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro V617F labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind V617F by monitoring its concentration variation when contacting with V617F, through tracking of the labeling. For example, a test compound (labeled) can be evaluated for its ability to reduce binding of another compound which is known to bind to V617F (i.e., standard compound). Accordingly, the ability of a test compound to compete with the standard compound for binding to V617F directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of V617F-associated diseases or disorders as described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 μm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

Example 1. 4-Methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

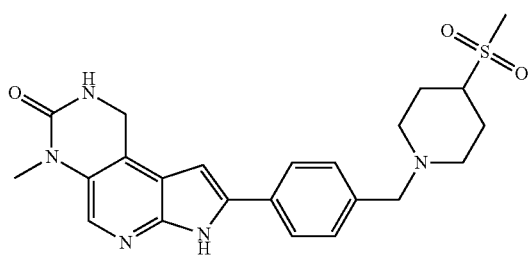 [SMILES: CN1C(=O)NCc2c1cnc1[nH]c(-c3ccc(CN4CCC(S(C)(=O)=O)CC4)cc3)cc21]

Step 1. 4-(Methylsulfonyl)-1-(4-(4,4,5,5-tetramethyl-1,3,2-dioxaborolan-2-yl)benzyl)piperidine

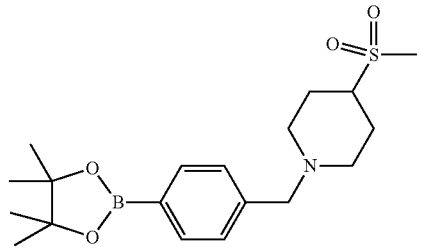

To a solution of 2-(4-(bromomethyl)phenyl)-4,4,5,5-tetramethyl-1,3,2-dioxaborolane (3000 mg, 10.10 mmol) in dimethylformamide (40 ml) was added cesium carbonate (9873 mg, 30.3 mmol) and 4-(methylsulfonyl)piperidine (1814 mg, 11.11 mmol). The resulting solution was stirred at room temperature (r.t.) for 1 hour. After this time, the reaction mixture was diluted with ethyl acetate and then washed with water and brine. The organic layer was dried over $MgSO_4$, filtered, and then concentrated to dryness. The resulting residue was used for next step without purification. LC-MS calculated for $C_{19}H_{31}BNO_4S$ $(M+H)^+$: m/z=380.2; found 380.2.

Step 2. 2-Bromo-4-chloro-5-nitro-1-(phenylsulfonyl)-1H-pyrrolo[2,3-b]pyridine

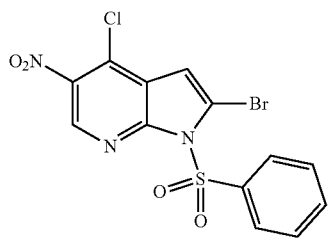

To a solution of 4-chloro-5-nitro-1-(phenylsulfonyl)-1H-pyrrolo[2,3-b]pyridine (Aurum Pharmatech, catalog number Q-3100, 20 g, 59.2 mmol) in tetrahydrofuran (250 ml) was added lithium diisopropylamide solution (2.0M in tetrahydrofuran/heptane/ethylbenzene, 89 mL, 178 mmol) over 10 minutes at −78° C. The resulting solution was stirred at −78° C. for 30 minutes, then 1,2-dibromo-1,1,2,2-tetrachloroethane (38.6 g, 118 mmol) in tetrahydrofuran was added and the resulting solution was then warmed up to r.t. over 30 minutes and stirred at r.t. for 1 hour. After this time, the reaction was quenched by addition of 1N HCl and then extracted by ethyl acetate. The organic layer was then washed with water and brine, dried over $MgSO_4$, filtered, and then concentrated to dryness. The residue was purified by silica gel chromatography using 0-100% ethyl acetate in hexanes to afford the desired product (14.2 g, 34.1 mmol) as a brownish solid. LC-MS calculated for $C_{13}H_8BrClN_3O_4S$ $(M+H)^+$: m/z=415.9; found 415.9.

Step 3. 2-(4-((4-(Methylsulfonyl)piperidin-1-yl)methyl)phenyl)-5-nitro-1-(phenylsulfonyl)-4-vinyl-1H-pyrrolo[2,3-b]pyridine

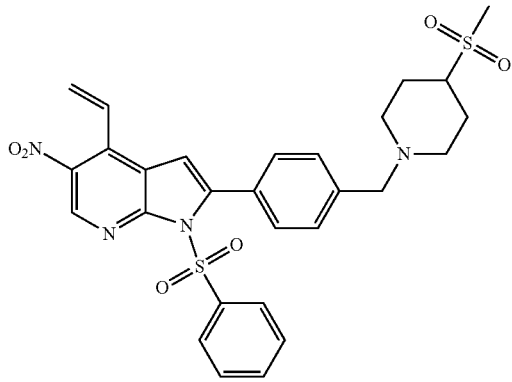 [SMILES: C=Cc1c([N+](=O)[O-])cnc2c1cc(-c1ccc(CN3CCC(S(C)(=O)=O)CC3)cc1)n2S(=O)(=O)c1ccccc1]

To a solution of 2-bromo-4-chloro-5-nitro-1-(phenylsulfonyl)-1H-pyrrolo[2,3-b]pyridine (699 mg, 1.677 mmol) and 4-(methylsulfonyl)-1-(4-(4,4,5,5-tetramethyl-1,3,2-dioxaborolan-2-yl)benzyl)piperidine (530 mg, 1.397 mmol) in dioxane (10 mL) and water (2.5 mL) was added cesium carbonate (1821 mg, 5.59 mmol) and 1,1-bis(diphenylphosphino)ferrocene-palladium(II)dichloride (228 mg, 0.279 mmol).

Nitrogen was bubbled through the solution for 5 minutes then the solution was stirred at 70° C. for 2 hours. After this time, 4,4,5,5-tetramethyl-2-vinyl-1,3,2-dioxaborolane (323 mg, 2.096 mmol) was added and the mixture was stirred for 3 hours at 100° C. The resulting solution was then cooled to r.t., water was removed, the organic layer was concentrated to dryness, and the resulting residue was purified by silica gel chromatography using 0-100% ethyl acetate in hexanes to afford desired product as yellowish oil (640 mg, 79%). LC-MS calculated for $C_{28}H_{29}N_4O_6S_2$ (M+H)$^+$: m/z=581.2; found 581.2.

Step 4. 2-(4-((4-(Methylsulfonyl)piperidin-1-yl)methyl)phenyl)-5-nitro-1-(phenylsulfonyl)-1H-pyrrolo[2,3-b]pyridine-4-carbaldehyde

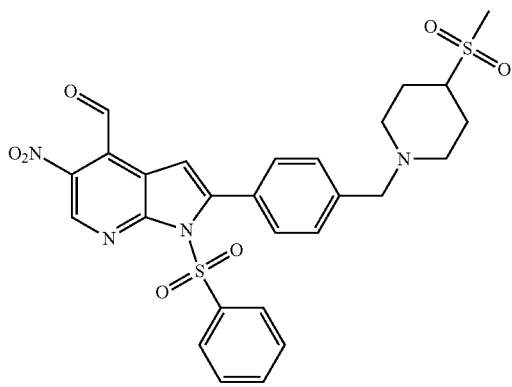 [SMILES: CS(=O)(=O)C1CCN(Cc2ccc(-c3cc4c(C=O)c([N+](=O)[O-])cnc4n3S(=O)(=O)c3ccccc3)cc2)CC1]

To a solution of 2-(4-((4-(methylsulfonyl)piperidin-1-yl)methyl)phenyl)-5-nitro-1-(phenylsulfonyl)-4-vinyl-1H-pyrrolo[2,3-b]pyridine (400 mg, 0.689 mmol) in THF (4 mL) and water (4.00 mL) was added sodium periodate (442 mg, 2.067 mmol) and potassium osmate dihydrate (12.69 mg, 0.034 mmol). The resulting solution was stirred at r.t. for 2 hours then diluted with dichloromethane (DCM) and then washed with water and brine. The organic layer was dried over MgSO$_4$, filtered, and then concentrated to dryness. The resulting residue was purified by silica gel chromatography using 0-20% methanol in DCM to afford desired product as yellowish oil (156 mg, 38.9%). LC-MS calculated for $C_{27}H_{27}N_4O_7S_2$ (M+H)$^+$: m/z=583.1; found 583.1.

Step 5. 4-(((2,4-Dimethoxybenzyl)amino)methyl)-2-(4-((4-(methylsulfonyl)piperidin-1-yl)methyl)phenyl)-1-(phenylsulfonyl)-1H-pyrrolo[2,3-b]pyridin-5-amine

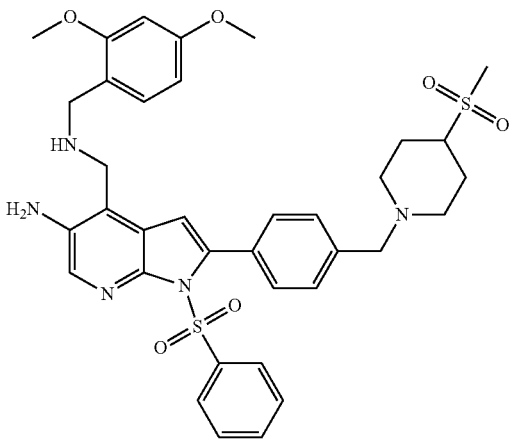 [SMILES: COc1ccc(CNCc2c(N)cnc3c2cc(-c2ccc(CN4CCC(S(C)(=O)=O)CC4)cc2)n3S(=O)(=O)c2ccccc2)c(OC)c1]

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (1700 mg, 2.92 mmol) in dichloromethane (20 mL) was added (2,4-dimethoxyphenyl)methanamine (1464 mg, 8.75 mmol) and acetic acid (835 µL, 14.59 mmol), and the resulting mixture was stirred at r.t. for 1 hour. Next, sodium cyanoborohydride (550 mg, 8.75 mmol) was added in one portion. The solution was then stirred at r.t. for 1 hour, then diluted with dichloromethane and washed with sodium bicarbonate solution and brine. The organic layer was dried over MgSO$_4$, filtered, and then concentrated to dryness. The residue was then dissolved in THF (10.0 mL), MeOH (10.0 mL), and water (10.0 mL). To the resulting suspension was added iron (815 mg, 14.59 mmol) and ammonium chloride (780 mg, 14.59 mmol) and the mixture was stirred at 80° C. for 15 hours. After this time, the mixture was cooled to r.t., diluted with 1:1 methanol and dichloromethane, and then filtered. The filtrate was concentrated to dryness the resulting residue was purified by silica gel chromatography using 0-60% methanol in DCM to afford desired product as brownish oil. LC-MS calculated for $C_{36}H_{42}N_5O_6S_2$(M+H)$^+$: m/z=704.3; found 704.3.

Step 6. 2-(2,4-Dimethoxybenzyl)-4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one

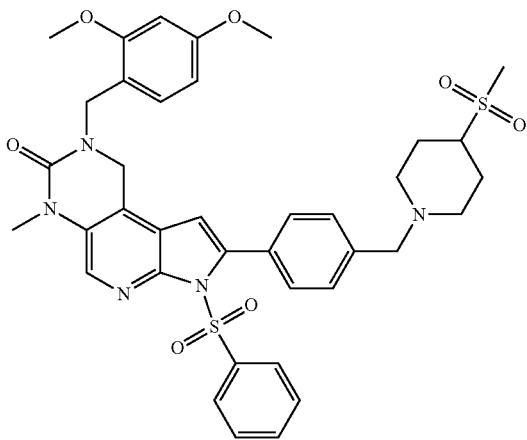 [SMILES: COc1ccc(CN2Cc3c(cnc4c3cc(-c3ccc(CN5CCC(S(C)(=O)=O)CC5)cc3)n4S(=O)(=O)c3ccccc3)N(C)C2=O)c(OC)c1]

To a solution of 4-(((2,4-dimethoxybenzyl)amino)methyl)-2-(4-((4-(methylsulfonyl)piperidin-1-yl)methyl)phenyl)-1-(phenylsulfonyl)-1H-pyrrolo[2,3-b]pyridin-5-amine (1400 mg, 1.989 mmol) in THF (40 mL) and DMF (5.0 mL) at 0° C. was added triethylamine (1386 µL, 9.94 mmol) and triphosgene (472 mg, 1.591 mmol, pre-dissolved in 5 mL THF). The reaction mixture was stirred at 0° C. for 10 minutes then warmed to r.t. After this time, the reaction mixture was quenched by aqueous sodium hydroxide solution then extracted with ethyl acetate. The organic layer was washed with brine then dried over MgSO$_4$, filtered, and then concentrated to dryness. The resulting residue was dissolved in DMF (20.0 mL) then iodomethane (187 µL, 2.98 mmol) and sodium hydride (119 mg, 2.98 mmol) were added. The resulting solution was stirred at r.t. for 30 minutes then quenched with water and extracted with ethyl acetate. The organic layer was washed with brine, dried over MgSO$_4$, filtered, and then concentrated to dryness. The residue was purified by silica gel chromatography using 0-30% methanol in DCM to afford desired product as brownish oil (500 mg, 33.8%). LC-MS calculated for $C_{38}H_{42}N_5O_7S_2$ (M+H)$^+$: m/z=744.2; found 744.4.

Step 7. 4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one

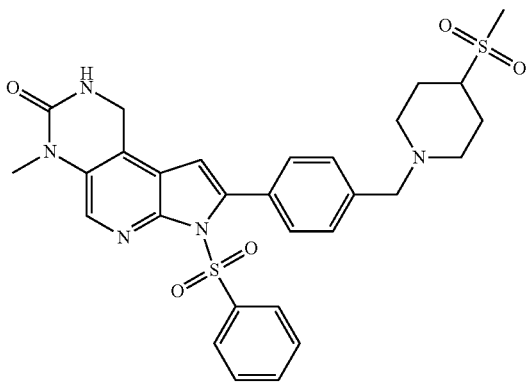 [SMILES: CN1C(=O)NCc2c1cnc1c2cc(-c2ccc(CN3CCC(S(C)(=O)=O)CC3)cc2)n1S(=O)(=O)c1ccccc1]

2-(2,4-dimethoxybenzyl)-4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one (500 mg, 0.672 mmol) was dissolved in trifluoroacetic acid (TFA, 5 mL, 64.9 mmol) and then stirred at r.t. for 1 hour. After this time, the reaction mixture was diluted with DCM and then washed with 1N NaOH solution. The organic layer was dried over MgSO$_4$, filtered, and then concentrated to dryness. The resulting residue was purified by silica gel chromatography using 0-40% methanol in DCM to afford desired product as brownish oil (350 mg, 48.7%). LC-MS calculated for $C_{29}H_{32}N_5O_5S_2$ (M+H)$^+$: m/z=594.2; found 594.1.

Step 8. 4-Methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

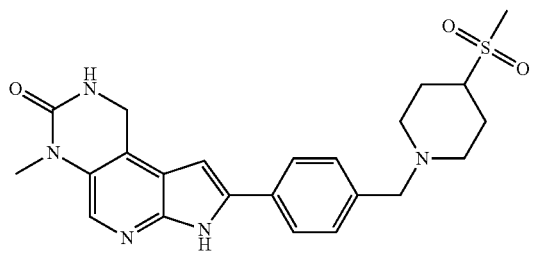 [SMILES: CN1C(=O)NCc2c1cnc1[nH]c(-c3ccc(CN4CCC(S(C)(=O)=O)CC4)cc3)cc21]

To a solution of 4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one (20 mg, 0.034 mmol) in 1 mL methanol was added 1 mL 2.5 M NaOH solution. The resulting solution was stirred at 80° C. for 1 hour and then cooled to r.t. The reaction mixture was then diluted with acetonitrile, filtered, and purified by prep-LCMS (XBridge C18 column, eluting with a gradient of acetonitrile/water containing 0.1% NH$_4$OH, at flow rate of 60 mL/min) to afford the desired compound. LC-MS calculated for $C_{23}H_{28}N_5O_3S$ (M+H)$^+$: m/z=454.2; found 454.4.

Example 2. 4-Methyl-8-(4-((4-(methylsulfonyl)piperidin-1-yl)methyl)phenyl)-2-phenyl-1,2,4,7-tetrahydro-3H-pyrrolo[3',2':5,6]pyrido[3,4-b]pyrimidin-3-one

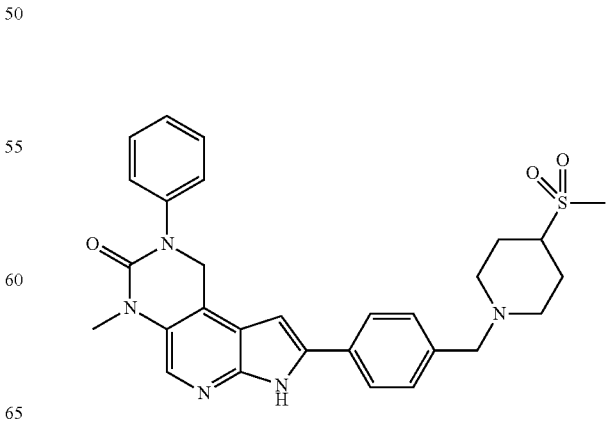

Step 1. 2-(4-((4-(Methylsulfonyl)piperidin-1-yl)methyl) phenyl)-4-((phenylamino)methyl)-1-(phenylsulfonyl)-1H-pyrrolo[2,3-b]pyridin-5-amine

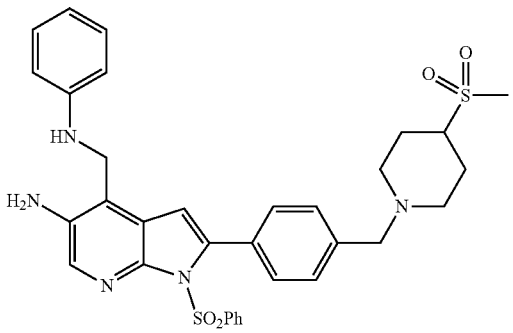

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (Example 1, Step 4, 200 mg, 0.343 mmol) in DCM (4 mL) was added aniline (96 mg, 1.030 mmol) and acetic acid (98 µL, 1.716 mmol). The reaction mixture was then stirred at r.t. for 1 hour before sodium cyanoborohydride (64.7 mg, 1.030 mmol) was added. The solution was then stirred at r.t. for 1 hour, diluted with DCM, and washed with NaHCO₃ solution and brine. The organic layer was dried over MgSO₄, filtered, and then concentrated to dryness. The residue was washed through a short silica gel column using 30% methanol in DCM. The obtained intermediate was dissolved in THF (4.00 mL) and EtOH (4.00 mL) then iron (96 mg, 1.716 mmol) and HCl (515 µL, 0.515 mmol) were added, and the resulting mixture was stirred at 80° C. for 1 hour. After this time, the mixture was cooled to r.t., diluted with 1:1 DCM and MeOH, then stirred for an additional 20 minutes before being filtered. The filtrate was concentrated to dryness then purified by silica gel chromatography using 0-60% methanol in DCM. LC-MS calculated for $C_{33}H_{36}N_5O_4S_2$ (M+H)⁺: m/z=630.2; found 630.2.

Step 2. 8-(4-((4-(Methylsulfonyl)piperidin-1-yl)methyl) phenyl)-2-phenyl-7-(phenylsulfonyl)-1,2,4,7-tetrahydro-3H-pyrrolo[3',2':5,6]pyrido[3,4-d]pyrimidin-3-one

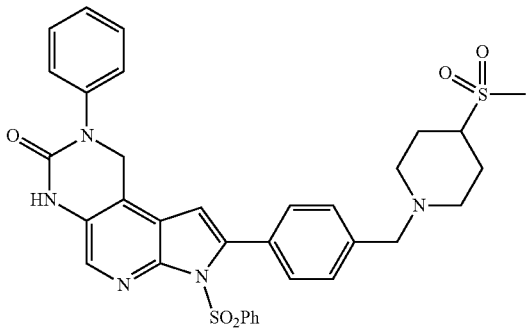

To a solution of 2-(4-((4-(methylsulfonyl)piperidin-1-yl)methyl)phenyl)-4-((phenylamino)methyl)-1-(phenylsulfonyl)-1H-pyrrolo[2,3-b]pyridin-5-amine (104 mg, 0.165 mmol) in THF (3 mL) was added triethylamine (46.0 µL, 0.330 mmol) and triphosgene (24.50 mg, 0.083 mmol) and the resulting mixture stirred at r.t. for 15 minutes. After this time, the mixture was quenched with water and extracted with ethyl acetate. The organic layer was washed with brine, dried over MgSO₄, filtered, and then concentrated to dryness to afford desired product. LC-MS calculated for $C_{34}H_{34}N_5O_5S_2$(M+H)⁺: m/z=656.2; found 656.2.

Step 3. 4-Methyl-8-(4-((4-(methylsulfonyl)piperidin-1-yl)methyl)phenyl)-2-phenyl-1,2,4,7-tetrahydro-3H-pyrrolo[3',2':5,6]pyrido[3,4-d]pyrimidin-3-one

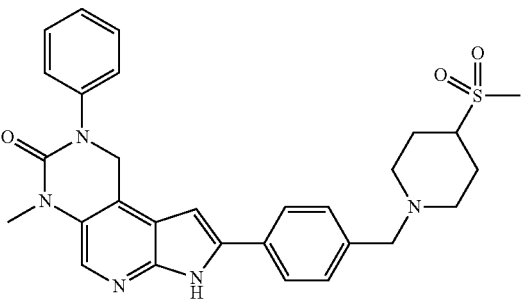

To a solution of 8-(4-((4-(Methylsulfonyl)piperidin-1-yl)methyl)phenyl)-2-phenyl-7-(phenylsulfonyl)-1,2,4,7-tetrahydro-3H-pyrrolo[3',2':5,6]pyrido[3,4-d]pyrimidin-3-one in DMF (2.00 mL) was added iodomethane (10.33 µL, 0.165 mmol). Sodium hydride (7.93 mg, 0.198 mmol) was added and the resulting mixture was stirred at r.t. for 10 minutes. After this time, the reaction was quenched with water and the mixture was extracted with ethyl acetate. The organic layer was washed with brine, dried over MgSO₄, filtered, and then concentrated to dryness. The resulting residue was suspended in 1:1 MeOH and 2.5M NaOH solution then stirred at 80° C. for 1 hour. After this time, the pH was adjusted to 1 then the mixture was diluted with methanol, filtered, and then purified by prep-LCMS (XBridge C18 column, eluting with a gradient of acetonitrile/water containing 0.1% TFA, at flow rate of 60 mL/min) to afford the title compound. LC-MS calculated for $C_{29}H_{32}N_5O_3S$ (M+H)⁺: m/z=530.2; found 530.2.

Example 3. 4-(4-Methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic Acid

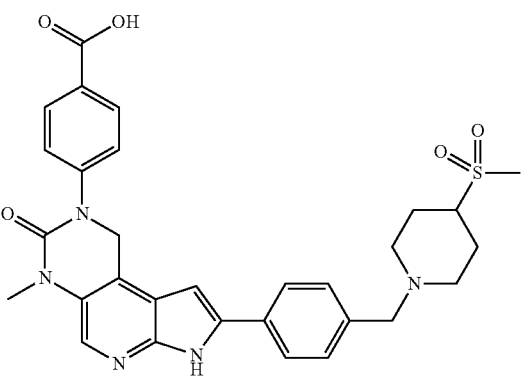 [SMILES: CN1C(=O)N(c2ccc(C(=O)O)cc2)Cc2c1cnc1[nH]c(-c3ccc(CN4CCC(S(C)(=O)=O)CC4)cc3)cc21]

The title compound was prepared according to the procedures described in Example 2, using methyl 4-aminobenzoate instead of aniline as starting material in Step 1. LC-MS calculated for $C_{30}H_{32}N_5O_5S$ (M+H)⁺: m/z=574.2; found 574.2.

Example 4. 8-(4-((4-(Methylsulfonyl)piperidin-1-yl)methyl)phenyl)-2-(pyridin-3-ylmethyl)-1,2,4,7-tetrahydro-3H-pyrrolo[3',2':5,6]pyrido[3,4-d]pyrimidin-3-one

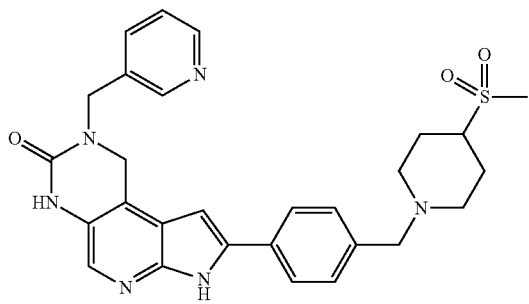 [SMILES: CS(=O)(=O)C1CCN(Cc2ccc(-c3cc4c5c(cnc4[nH]3)NC(=O)N(Cc3cccnc3)C5)cc2)CC1]

Step 1. 5-Amino-2-(4-((4-(methylsulfonyl)piperidin-1-yl)methyl)phenyl)-1-(phenylsulfonyl)-1H-pyrrolo[2,3-b]pyridine-4-carbaldehyde

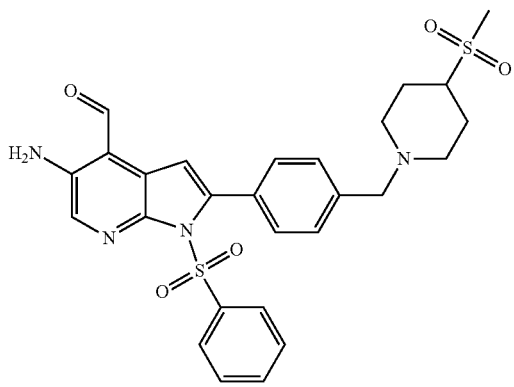

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (Example 1, Step 4, 500 mg, 0.858 mmol) in THF (3 mL), MeOH (3.00 mL) and water, (3.00 mL) was added iron (240 mg, 4.29 mmol) and ammonium chloride (230 mg, 4.29 mmol) and the resulting mixture was stirred at 60° C. for 2 hours. After this time, the mixture was cooled to r.t., filtered, and then concentrated to dryness. The residue was purified by silica gel chromatography using 0-30% methanol in DCM to afford desired product as brownish oil (0.21 g, 44.3%). LC-MS calculated for $C_{27}H_{29}N_4O_5S_2$ (M+H)⁺: m/z=553.2; found 553.1.

Step 2. 8-(4-((4-(methylsulfonyl)piperidin-1-yl)methyl)phenyl)-2-(pyridin-3-ylmethyl)-1,2,4,7-tetrahydro-3H-pyrrolo[3',2':5,6]pyrido[3,4-d]pyrimidin-3-one

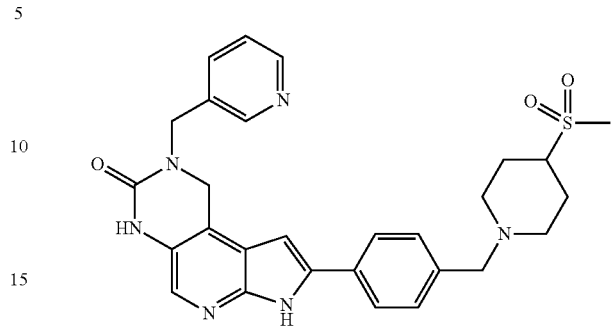

To a solution of 5-amino-2-(4-((4-(methylsulfonyl)piperidin-1-yl)methyl)phenyl)-1-(phenylsulfonyl)-1H-pyrrolo[2,3-b]pyridine-4-carbaldehyde (50 mg, 0.090 mmol) in MeOH (1 mL) and THF (0.5 mL) was added pyridin-3-ylmethanamine (98 mg, 0.91 mmol), and the resulting mixture was stirred at r.t. for 15 hours. After this time, sodium borohydride (17.11 mg, 0.452 mmol) was added. Additional sodium borohydride was then added until all imine was consumed. The resulting mixture was diluted with ethyl acetate and then washed with water and brine. The aqueous layer was extracted with ethyl acetate and then washed with brine. The combined organic layer was dried over MgSO₄, filtered, and then concentrated to dryness. The resulting residue was dissolved in THF (1.0 mL), then CDI (44.0 mg, 0.271 mmol) was added in one portion and the resulting mixture was stirred at r.t. for 30 minutes. After this time, the mixture was diluted with 1 mL MeOH and 1 mL 2.5M NaOH, then stirred at 60° C. for 2 hours. After this time, the mixture was cooled to r.t., the pH was adjusted to 1, and the residue purified by prep-LCMS (XBridge C18 column, eluting with a gradient of acetonitrile/water containing 0.1% TFA, at flow rate of 60 mL/min) to afford the title compound. LC-MS calculated for $C_{28}H_{31}N_6O_3S$ (M+H)⁺: m/z=531.2; found 531.1.

Example 5. 2-Cyclohexyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

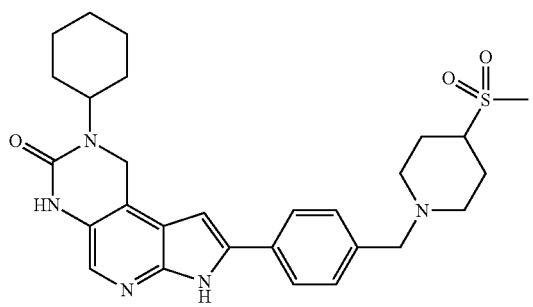 [SMILES: CS(=O)(=O)C1CCN(Cc2ccc(-c3cc4c5c(cnc4[nH]3)NC(=O)N(C3CCCCC3)C5)cc2)CC1]

Step 1. 4-((Cyclohexylamino)methyl)-2-(4-((4-(methylsulfonyl)piperidin-1-yl)methyl)phenyl)-1-(phenylsulfonyl)-1H-pyrrolo[2,3-b]pyridin-5-amine

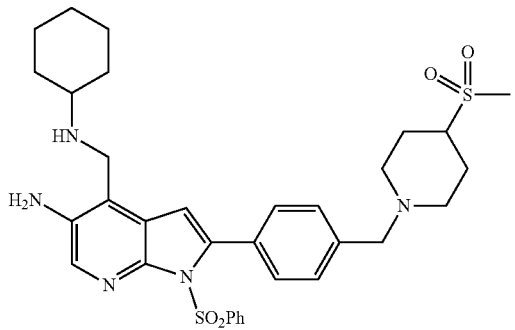

To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (Example 1, Step 4, 50 mg, 0.086 mmol) in DCM (1 mL) was added acetic acid (24.56 μL, 0.429 mmol) and cyclohexanamine (25.5 mg, 0.257 mmol), and the resulting mixture was stirred for 3 hours at r.t. After this time, sodium cyanoborohydride (27.0 mg, 0.429 mmol) was added and the reaction mixture was stirred for an additional 1 hour at r.t. After this time, the reaction mixture was diluted with DCM then washed with water and aqueous NaHCO$_3$ solution. The organic layer was dried over MgSO$_4$, filtered, and then concentrated to dryness. The resulting residue was then dissolved in MeOH (1.0 mL) and THF (1.0 mL), then Pd on carbon (10 mg) was added and the mixture was stirred under H$_2$ atmosphere at 60° C. for 1 hour. After this time, the reaction mixture was filtered, then diluted with methanol, and purified by prep-LCMS (XBridge C18 column, eluting with a gradient of acetonitrile/water containing 0.1% TFA, at flow rate of 60 mL/min) to afford the title compound. LC-MS calculated for $C_{33}H_{42}N_5O_4S_2$(M+H)$^+$: m/z=635.2; found 635.1.

Step 2. 2-Cyclohexyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

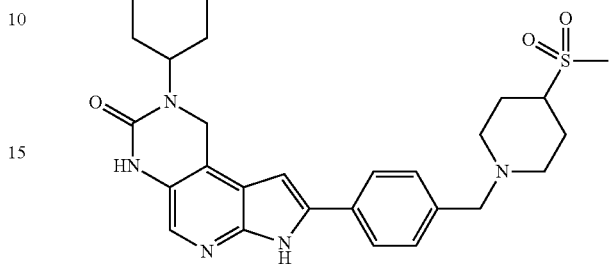

The 4-((cyclohexylamino)methyl)-2-(4-((4-(methylsulfonyl)piperidin-1-yl)methyl)phenyl)-1-(phenylsulfonyl)-1H-pyrrolo[2,3-b]pyridin-5-amine obtained from Step 1 was dissolved in THF, then CDI (44.0 mg, 0.271 mmol) was added and the resulting mixture was stirred at r.t. for 2 hours. After this time, the mixture was diluted with 1 mL 2.5M NaOH solution then stirred at 60° C. for 1 hour. After this time, the mixture was diluted with methanol, filtered, and then purified by prep-LCMS (XBridge C18 column, eluting with a gradient of acetonitrile/water containing 0.1% TFA, at flow rate of 60 mL/min) to afford the title compound. LC-MS calculated for $C_{28}H_{36}N_5O_3S$ (M+H)$^+$: m/z=522.2; found 522.1.

Examples 6-7

Examples 6-7 of Table 2 were prepared according to the procedures described in Example 4.

TABLE 2

| Ex. No. | Name | R | LCMS [M + H]$^+$ |
|---|---|---|---|
| 6 | 4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)cyclohexane-1-carboxylic acid |  | 566.2 |

TABLE 2-continued

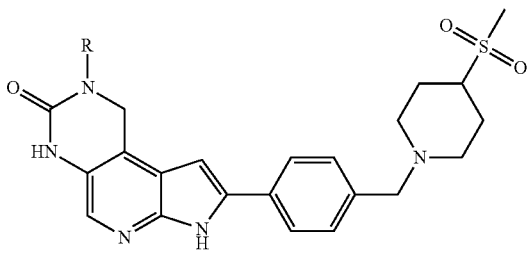

| Ex. No. | Name | R | LCMS [M + H]+ |
|---|---|---|---|
| 7 | 4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)piperidine-1-sulfonamide | ![R group] | 602.2 |

Example 8. 2-(4-((2-Methoxyethyl)amino)phenyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

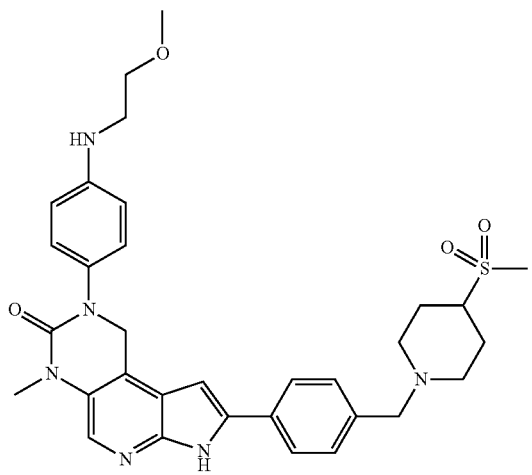

Step 1. 4-(((4-Bromophenyl)amino)methyl)-2-(4-((4-(methylsulfonyl)piperidin-1-yl)methyl)phenyl)-1-(phenylsulfonyl)-1H-pyrrolo[2,3-b]pyridin-5-amine To a solution of 2-(4-((4-(methylsulfonyl)piperidin-1-yl)methyl)phenyl)-5-nitro-1-(phenylsulfonyl)-1H-pyrrolo[2,3-b]pyridine-4-carbaldehyde (Example 1, Step 4, 1800 mg, 3.09 mmol) in DCM (36 mL) was added 4-bromoaniline (1594 mg, 9.27 mmol) and acetic acid (884 µL, 15.45 mmol), and the resulting mixture was stirred at r.t. for 1 hour. Next, sodium cyanoborohydride (582 mg, 9.27 mmol) was added and the mixture was stirred at r.t. for 1 hour. The mixture was then diluted with DCM and washed with NaHCO₃ solution and brine. The organic layer was dried over MgSO₄, filtered, and then concentrated to dryness. The residue was dissolved in THF (10.0 mL), water (10.0 mL), and MeOH (10 mL). To the resulting suspension was added iron (863 mg, 15.45 mmol) and ammonium chloride (826 mg, 15.45 mmol), and the mixture was stirred at 80° C. for 2 hours. After this time, the mixture was cooled to r.t., filtered, and concentrated to dryness. The resulting residue was purified by silica gel chromatography using 0-50% methanol in DCM to afford desired product as brownish oil (1.32 g, 60.3%). LC-MS calculated for $C_{33}H_{35}BrN_5O_4S_2$ (M+H)+: m/z=708.0; found 708.0.

Step 2. 2-(4-Bromophenyl)-4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one

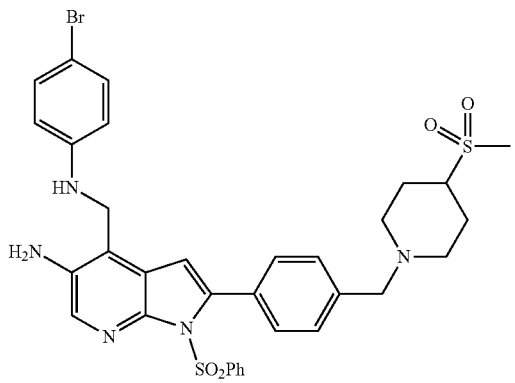

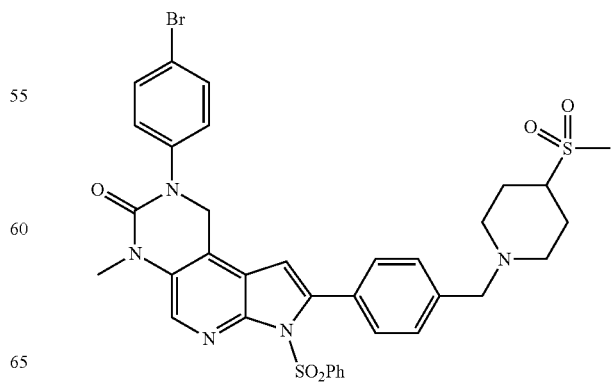

To a solution of 4-(((4-bromophenyl)amino)methyl)-2-(4-((4-(methylsulfonyl)piperidin-1-yl)methyl)phenyl)-1-(phenylsulfonyl)-1H-pyrrolo[2,3-b]pyridin-5-amine (1.2 g, 1.693 mmol) in THF (40 mL) was added triethylamine (0.708 mL, 5.08 mmol) and triphosgene (0.251 g, 0.847 mmol), and the resulting mixture was stirred at r.t. for 30 minutes. After this time, the reaction was quenched with NaOH solution, and the mixture was extracted with ethyl acetate. The organic layer was washed with brine, dried over MgSO$_4$, filtered, and then concentrated to dryness. The resulting residue was then dissolved in DMF (10.0 mL) and iodomethane (0.159 mL, 2.54 mmol). Sodium hydride (0.102 g, 2.54 mmol) was added and the resulting mixture was stirred at r.t. for 30 minutes. After this time, the reaction was quenched with water and the mixture was extracted with ethyl acetate. The organic layer was washed with brine, dried over MgSO$_4$, filtered, and then concentrated to dryness. The residue was purified by silica gel chromatography using 0-10% methanol in DCM to afford desired product as brownish oil (704 mg, 55.5%). LC-MS calculated for $C_{35}H_{34}BrN_5O_5S_2$ (M+H)$^+$: m/z=748.0; found 748.0.

Step 3. 2-(4-((2-Methoxyethyl)amino)phenyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

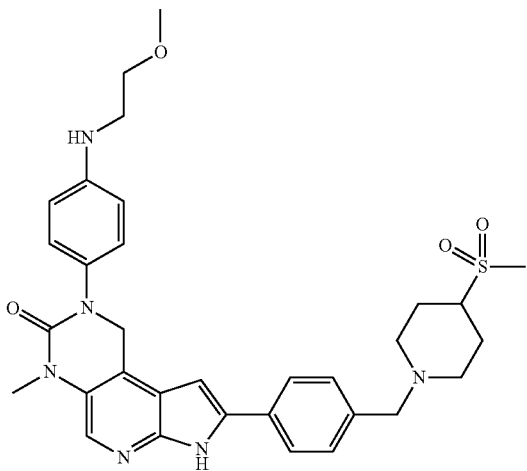 [SMILES: COCCNc1ccc(N2Cc3c(cnc4[nH]c(-c5ccc(CN6CCC(S(C)(=O)=O)CC6)cc5)cc34)N(C)C2=O)cc1]

To a solution of 2-(4-bromophenyl)-4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one (25 mg, 0.033 mmol) in dioxane (1 mL) was added 2-methoxyethan-1-amine (7.52 mg, 0.100 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (tBuBrettPhos Pd G3, 8.56 mg, 10.02 µmol) and cesium carbonate (32.6 mg, 0.100 mmol). N$_2$ was then bubbled through the mixture for 1 minute, then the mixture was heated at 100° C. and stirred for 15 hours at 100° C. After this time, the mixture was cooled to r.t., diluted with methanol and 2.5M NaOH solution, and then stirred at 60° C. for 1 hour. The resulting solution was diluted with methanol and water, filtered, and purified by prep-LCMS (XBridge C18 column, eluting with a gradient of acetonitrile/water containing 0.1% NH$_4$OH, at flow rate of 60 mL/min) to afford the title compound. LC-MS calculated for $C_{32}H_{39}N_6O_4S$ (M+H)$^+$: m/z=603.2; found 603.1.

Example 9. 2-Cyano-N-(4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)phenyl)acetamide

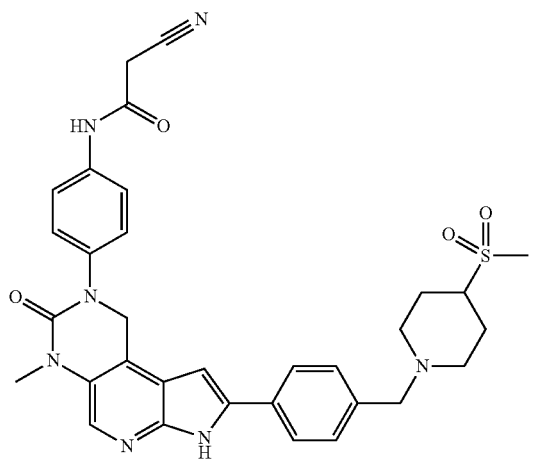 [SMILES: CN1C(=O)N(c2ccc(NC(=O)CC#N)cc2)Cc2c1cnc1[nH]c(-c3ccc(CN4CCC(S(C)(=O)=O)CC4)cc3)cc21]

The title compound was prepared according to the procedures described in Example 8, using 2-methoxyethan-1-amine instead of aniline as starting material in Step 3. LC-MS calculated for $C_{32}H_{34}N_7O_4S$ (M+H)$^+$: m/z=612.2; found 612.2.

Example 10. 4-(1,4-Dimethyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic Acid

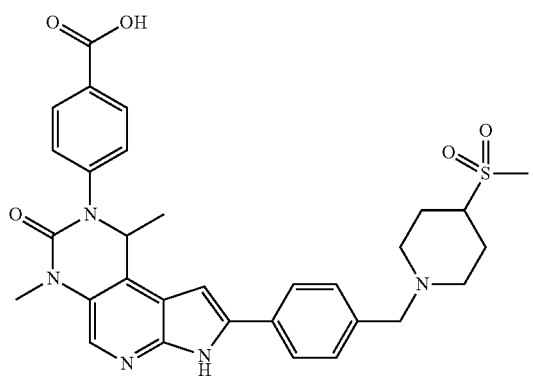 [SMILES: CC1c2c(cnc3[nH]c(-c4ccc(CN5CCC(S(C)(=O)=O)CC5)cc4)cc23)N(C)C(=O)N1c1ccc(C(=O)O)cc1]

Step 1. 4-Chloro-2-(4-((4-(methylsulfonyl)piperidin-1-yl)methyl)phenyl)-5-nitro-1-(phenylsulfonyl)-1H-pyrrolo[2,3-b]pyridine

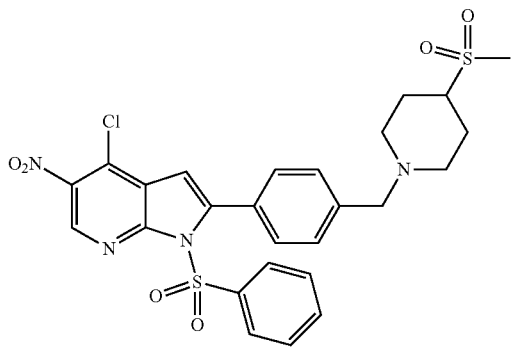 [SMILES: CS(=O)(=O)C1CCN(Cc2ccc(-c3cc4c(Cl)c([N+](=O)[O-])cnc4n3S(=O)(=O)c3ccccc3)cc2)CC1]

To a solution of 2-bromo-4-chloro-5-nitro-1-(phenylsulfonyl)-1H-pyrrolo[2,3-b]pyridine (Example 1, Step 2, 2.5 g, 6.00 mmol) and 4-(methylsulfonyl)-1-(4-(4,4,5,5-tetramethyl-1,3,2-dioxaborolan-2-yl)benzyl)piperidine (Example 1, Step 1, 1.366 g, 3.60 mmol) in dioxane (50 mL) and water (12.50 mL) was added cesium carbonate (7.82 g, 24.00 mmol) and [1,1'-bis(diphenylphosphino)ferrocene]dichloropalladium(II) (0.980 g, 1.20 mmol). $N_2$ was bubbled through the mixture for 5 minutes then the mixture was stirred at 70° C. for 2 hours. The resulting solution was then cooled to r.t. and water was removed. The resulting mixture was concentrated to dryness and then purified by silica gel chromatography using 0-5% methanol in dichloromethane with 1% triethylamine as additive to afford desired product as brownish oil (1.40 g, 2.38 mmol). LC-MS calculated for $C_{28}H_{29}N_4O_6S_2$ $(M+H)^+$: m/z=589.2; found 589.2.

Step 2. 1-(2-(4-((4-(Methylsulfonyl)piperidin-1-yl)methyl)phenyl)-5-nitro-1-(phenylsulfonyl)-1H-pyrrolo[2,3-b]pyridin-4-yl)ethan-1-one

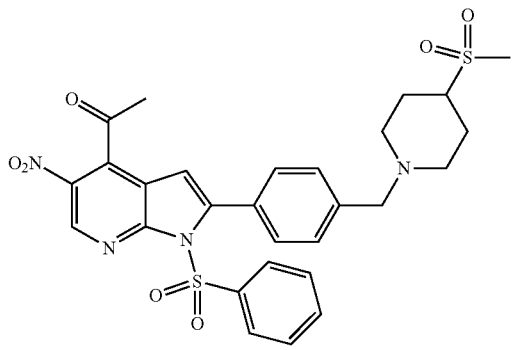 [SMILES: CC(=O)c1c([N+](=O)[O-])cnc2c1cc(-c1ccc(CN3CCC(S(C)(=O)=O)CC3)cc1)n2S(=O)(=O)c1ccccc1]

To a solution of 4-chloro-2-(4-((4-(methylsulfonyl)piperidin-1-yl)methyl)phenyl)-5-nitro-1-(phenylsulfonyl)-1H-pyrrolo[2,3-b]pyridine (1600 mg, 2.72 mmol) in dioxane (20 mL) was added 1-ethoxyvinyltri-n-butyltin (1101 µL, 3.26 mmol) and triphenylphosphine palladium chloride (381 mg, 0.543 mmol), and the resulting mixture was stirred at 100° C. for 2 hours. After this time, the mixture was cooled to r.t. then water (2 mL) and concentrated hydrochloric acid (2 mL) were added and the resulting mixture was stirred for 1 hour at r.t. After this time, the pH was adjusted to 7, the mixture was diluted with water, and extracted with dichloromethane. The organic layer was dried over $MgSO_4$, filtered, and then concentrated to dryness. The residue was purified by silica gel chromatography using 0-10% methanol in DCM with 1% TEA as additive to afford desired product (1.33 g, 2.23 mmol). LC-MS calculated for $C_{28}H_{29}N_4O_7S_2$ $(M+H)^+$: m/z=597.2; found 597.2.

Step 3. Methyl 4-((1-(5-amino-2-(4-((4-(methylsulfonyl)piperidin-1-yl)methyl)phenyl)-1-(phenylsulfonyl)-1H-pyrrolo[2,3-b]pyridin-4-yl)ethyl)amino)benzoate

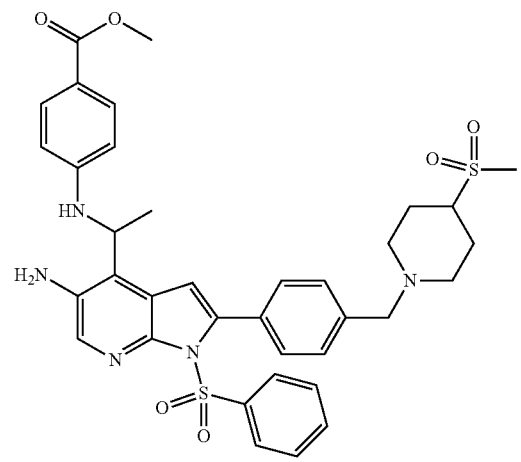 [SMILES: COC(=O)c1ccc(NC(C)c2c(N)cnc3c2cc(-c2ccc(CN4CCC(S(C)(=O)=O)CC4)cc2)n3S(=O)(=O)c2ccccc2)cc1]

To a solution of 1-(2-(4-((4-(methylsulfonyl)piperidin-1-yl)methyl)phenyl)-5-nitro-1-(phenylsulfonyl)-1H-pyrrolo[2,3-b]pyridin-4-yl)ethan-1-one (400 mg, 0.670 mmol) in DCM (5 mL) was added methyl 4-aminobenzoate (304 mg, 2.011 mmol) and titanium tetrachloride (1006 µL, 1.006 mmol), and the resulting mixture was stirred at r.t. for 1 hour. Next, a solution of sodium cyanoborohydride (211 mg, 3.35 mmol) in MeOH (1.00 mL) was added. The reaction mixture was stirred at r.t. for 1 hour then diluted with NaOH 1N solution, filtered, and then extracted with DCM. The organic layer was washed with water, dried over $MgSO_4$, filtered, and then concentrated to dryness. The residue was dissolved in THF (1 mL), MeOH (1.00 mL), and water (1.00 mL). To the resulting suspension was added iron (187 mg, 3.35 mmol) and ammonium chloride (179 mg, 3.35 mmol), and the resulting mixture was stirred at 80° C. for 90 minutes. After this time, the mixture was cooled to r.t., diluted with methanol, filtered, and then concentrated to dryness. The resulting residue was purified by silica gel chromatography using 0-30% methanol in DCM with 1% TEA as additive to afford desired product as brownish oil (164 mg, 34.9%). LC-MS calculated for $C_{36}H_{40}N_5O_6S_2(M+H)^+$: m/z=702.2; found 702.2.

Step 4. 4-(1,4-Dimethyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic Acid

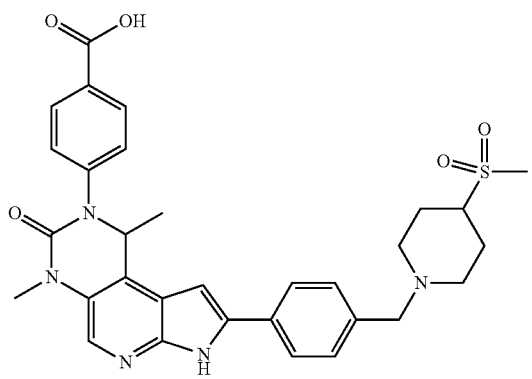

To a solution of methyl 4-((1-(5-amino-2-(4-((4-(methylsulfonyl)piperidin-1-yl)methyl)phenyl)-1-(phenylsulfonyl)-1H-pyrrolo[2,3-b]pyridin-4-yl)ethyl)amino)benzoate (100 mg, 0.142 mmol) in THF (2.85 mL) was added triethylamine (59.6 µL, 0.427 mmol) and triphosgene (21.14 mg, 0.071 mmol), and the resulting mixture was stirred at r.t. for 10 minutes. After this time, the mixture was quenched with 1N NaOH then extracted with DCM. The organic layer was concentrated to dryness and the resulting residue was dissolved in 1 mL DMF. Iodomethane (13.36 µL, 0.214 mmol) was added followed by addition of sodium hydride (8.55 mg, 0.214 mmol). The resulting solution was then stirred at r.t. for 30 minutes, quenched with water, and extracted with ethyl acetate. The resulting solution was then concentrated to dryness, then dissolved in 1:1 1N NaOH and methanol and stirred at 80° C. for 1 hour. After this time, the mixture was cooled to r.t., diluted with methanol, and purified by prep-LCMS (XBridge C18 column, eluting with a gradient of acetonitrile/water containing 0.1% $NH_4OH$, at flow rate of 60 mL/min) to afford the title compound as a racemic mixture. LC-MS calculated for $C_{31}H_{34}N_5O_5S$ $(M+H)^+$: m/z=588.2; found 588.1. $^1H$ NMR (600 MHz, DMSO-d6) δ 12.16 (s, 1H), 8.11 (s, 1H), 7.98-7.93 (m, 2H), 7.89 (d, J=8.0 Hz, 2H), 7.52-7.46 (m, 2H), 7.39 (d, J=8.1 Hz, 2H), 7.08 (s, 1H), 5.49-5.37 (m, 1H), 3.52 (s, 2H), 3.44 (s, 3H), 3.10-3.01 (m, 1H), 2.96 (dt, J=12.5, 3.3 Hz, 2H), 2.92 (s, 3H), 2.04-1.96 (m, 4H), 1.63 (qd, J=12.2, 3.9 Hz, 2H), 1.49 (d, J=6.5 Hz, 3H).

Example 11. 4-(9-(4-Methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-(pyridin-3-yl)benzamide, Bistrifluoroacetic Acid Salt

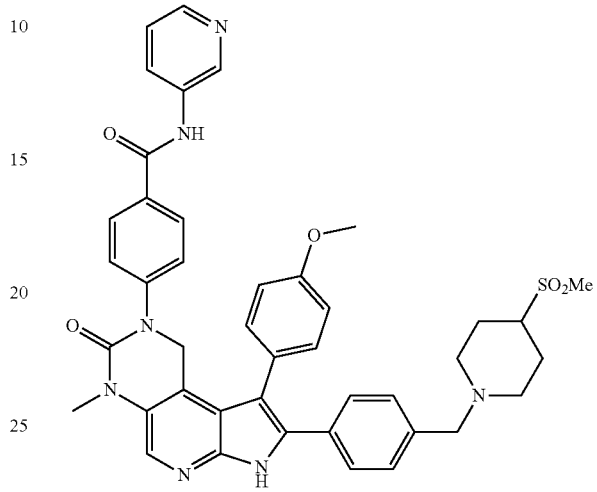

Step 1. 5-Nitro-1-(phenylsulfonyl)-4-vinyl-1H-pyrrolo[2,3-b]pyridine

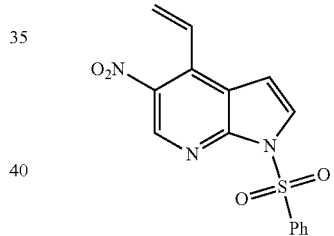

A mixture of 4-chloro-5-nitro-1-(phenylsulfonyl)-1H-pyrrolo[2,3-b]pyridine (7.00 g, 20.7 mmol) (Enamine) and 4,4,5,5-tetramethyl-2-vinyl-1,3,2-dioxaborolane (4.79 g, 31.1 mmol) in 1,4-dioxane (72 mL) and water (22 mL) was treated with tribasic potassium phosphate (13.2 g, 62.2 mmol) and degassed with nitrogen for 15 min. The reaction mixture was treated with dicyclohexyl(2',4',6'-triisopropyl-biphenyl-2-yl)phosphine-(2'-aminobiphenyl-2-yl)(chloro)palladium (1:1) (XPhos Pd G2) (1.63 g, 2.07 mmol), degassed with nitrogen for 15 min, and stirred at 70° C. for 2.5 h. The reaction mixture was then diluted with ethyl acetate (70 mL) and water (30 mL) and filtered through Celite. The aqueous layer was separated and extracted with ethyl acetate (2×50 mL). The combined organic extracts were washed with saturated sodium chloride solution, dried over magnesium sulfate, filtered, and concentrated to a brown solid. The solid was suspended in methanol (35 mL) and stirred for 2 h. The solid was isolated by filtration, washed with methanol (3×5 mL), and dried under high vacuum to afford the desired product (6.16 g, 90.2%) as a brown solid. LCMS for $C_{15}H_{12}N_3O_4S$ $(M+H)^+$: m/z=330.1; Found: 330.0.

Step 2. 5-Nitro-1-(phenylsulfonyl)-1H-pyrrolo[2,3-b]pyridine-4-carbaldehyde

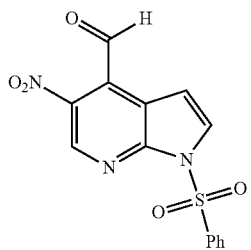 [SMILES: O=Cc1c([N+](=O)[O-])cnc2c1ccn2S(=O)(=O)c1ccccc1]

To a solution of 5-nitro-1-(phenylsulfonyl)-4-vinyl-1H-pyrrolo[2,3-b]pyridine (6.16 g, 18.7 mmol) in THF (130 mL) was added water (26.0 mL) and potassium osmate dihydrate (0.138 g, 0.374 mmol). Sodium periodate (12.0 g, 56.1 mmol) was then added and the resulting mixture was stirred for 22 h. The reaction mixture was diluted with dichloromethane (200 mL) and water (200 mL), and the organic layer was collected. Additional dichloromethane and 20% sodium thiosulfate solution was added to the aqueous layer, and the organic layer was collected. The aqueous layer was then back-extracted with dichloromethane. The combined extracts were washed with 20% sodium thiosulfate solution and brine, dried over magnesium sulfate, filtered, and concentrated to give the desired product (5.64 g, 91.1% yield) as a brown solid. LCMS for $C_{14}H_{10}N_3O_5S$ (M+H)$^+$: m/z=332.0; Found: 332.0.

Step 3. tert-Butyl 4-(((5-nitro-1-(phenylsulfonyl)-1H-pyrrolo[2,3-b]pyridin-4-yl)methyl)amino)benzoate

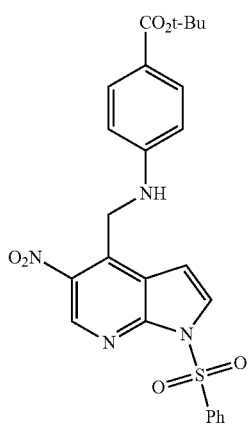

To a solution of 5-nitro-1-(phenylsulfonyl)-1H-pyrrolo[2,3-b]pyridine-4-carbaldehyde (5.64 g, 17.0 mmol) and tert-butyl 4-aminobenzoate (3.29 g, 17.0 mmol) in dichloromethane (155 mL) was added acetic acid (0.975 mL, 17.0 mmol). The resulting mixture was stirred for 64 h and was cooled to 0° C. Sodium cyanoborohydride (1.28 g, 20.4 mmol) was added, the cooling bath was removed, and the reaction mixture was stirred for 1 h, at which time additional sodium cyanoborohydride (0.267 g, 4.26 mmol) was added. The mixture was stirred for an additional 30 min, then cooled with ice, diluted with 200 mL of saturated sodium bicarbonate solution, and warmed to ambient temperature. The resulting solids were filtered, the filtrate were separated, and the aqueous layer was extracted with dichloromethane (2×150 mL). The combined dichloromethane extracts were washed with saturated sodium chloride solution, dried over sodium sulfate, filtered, and concentrated to give a brown foam. Purification by flash column chromatography using ethyl acetate in hexanes (0% to 100%) afforded the desired product (4.91 g, 56.7%) as a yellow foam. LC/MS for $C_{25}H_{25}N_4O_6S$ (M+H)$^+$: m/z=509.1; Found: 509.2.

Step 4. tert-Butyl 4-(((5-amino-1-(phenylsulfonyl)-1H-pyrrolo[2,3-b]pyridin-4-yl)methyl)amino)benzoate

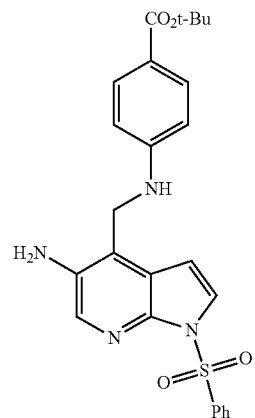 [SMILES: CC(C)(C)OC(=O)c1ccc(NCc2c([N+](=O)[O-])cnc3c2ccn3S(=O)(=O)c2ccccc2)cc1]

To a mixture of tert-butyl 4-(((5-nitro-1-(phenylsulfonyl)-1H-pyrrolo[2,3-b]pyridin-4-yl)methyl)amino)benzoate (4.75 g, 9.35 mmol) and iron (3.68 g, 65.9 mmol) in methanol (31.8 mL), THF (31.8 mL), and water (31.8 mL) was added ammonium chloride (3.66 g, 68.4 mmol). The resulting mixture was refluxed at 70° C. for 2 h. The mixture was diluted with saturated sodium chloride solution (50 mL) and ethyl acetate (50 mL), then filtered through Celite. The Celite was washed with EtOAc (200 mL). The filtrate was transferred to a separatory funnel with saturated sodium chloride solution (50 mL) and the layers were separated. The ethyl acetate layer was dried over sodium sulfate, filtered, and concentrated to afford the desired product (4.62 g, >100%) as a yellow foam. Assumed 100% yield and carried on to step 5. LCMS for $C_{25}H_{27}N_4O_4S$ (M+H)$^+$: m/z=479.2; Found: 479.2.

Step 5. tert-Butyl 4-(3-oxo-7-(phenylsulfonyl)-1,3,4,7-tetrahydro-2H-pyrrolo[3',2':5,6]pyrido[3,4-d]pyrimidin-2-yl)benzoate

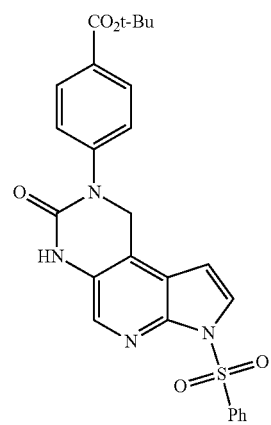 [SMILES: CC(C)(C)OC(=O)c1ccc(N2Cc3c(cnc4c3ccn4S(=O)(=O)c3ccccc3)NC2=O)cc1]

To a suspension of tert-butyl 4-(((5-amino-1-(phenylsulfonyl)-1H-pyrrolo[2,3-b]pyridin-4-yl)methyl)amino)

benzoate (4.47 g, 9.34 mmol) in THF (46.7 mL) was added carbonyldiimidazole (7.57 g, 46.7 mmol). The resulting suspension was stirred at ambient temperature for 18 h. The suspension was cooled with ice while water (125 mL) was added dropwise to quench any excess carbonyldiimidazole. The suspension was filtered and the tan solid was washed with water (3×30 mL). The solid was concentrated from acetonitrile (2×) to provide the desired product (4.28 g, 90.9%) as a tan solid. LCMS for $C_{26}H_{25}N_4O_5S$ (M+H)$^+$: m/z=505.2; Found: 505.1.

Step 6. tert-Butyl 4-(4-methyl-3-oxo-7-(phenylsulfonyl)-1,3,4,7-tetrahydro-2H-pyrrolo[3',2':5,6]pyrido[3,4-d]pyrimidin-2-yl)benzoate

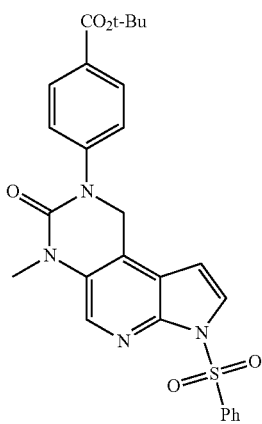 [SMILES: CN1C(=O)N(c2ccc(C(=O)OC(C)(C)C)cc2)Cc2c1cnc1c2ccn1S(=O)(=O)c1ccccc1]

To a suspension of tert-butyl 4-(3-oxo-7-(phenylsulfonyl)-1,3,4,7-tetrahydro-2H-pyrrolo[3',2':5,6]pyrido[3,4-d]pyrimidin-2-yl)benzoate (3.30 g, 6.54 mmol) in DMF (32.7 mL) and THF (32.7 mL) was added cesium carbonate (6.39 g, 19.6 mmol) and methyl iodide (2.86 mL, 45.8 mmol). The resulting suspension was stirred for 1.5 h. The suspension was diluted with ethyl acetate (200 mL) and water (200 mL). The layers were separated, and the ethyl acetate layer was washed with saturated sodium chloride solution, dried over sodium sulfate, filtered, and concentrated to an orange solid. Purification by flash column chromatography using methanol in dichloromethane (0% to 10%) gave the desired product (3.39 g, 100%) as a tan solid. LCMS for $C_{27}H_{27}N_4O_5S$ (M+H)$^+$: m/z=519.2; Found: 519.2.

Step 7. tert-Butyl 4-(8-bromo-4-methyl-3-oxo-7-(phenylsulfonyl)-1,3,4,7-tetrahydro-2H-pyrrolo[3',2':5,6]pyrido[3,4-d]pyrimidin-2-yl)benzoate

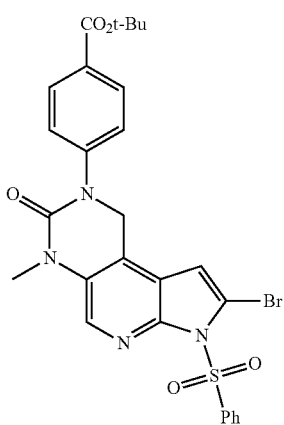 [SMILES: CN1C(=O)N(c2ccc(C(=O)OC(C)(C)C)cc2)Cc2c1cnc1c2cc(Br)n1S(=O)(=O)c1ccccc1]

To a solution of tert-butyl 4-(4-methyl-3-oxo-7-(phenylsulfonyl)-1,3,4,7-tetrahydro-2H-pyrrolo[3',2':5,6]pyrido[3,4-d]pyrimidin-2-yl)benzoate (2.71 g, 5.22 mmol) in THF (35 mL) at −78° C. was added LDA (2M solution in THF/heptane/ethylbenzene, 3.92 mL, 7.83 mmol). The resulting mixture was stirred at −78° C. for 1.5 min, a solution of 1,2-dibromo-1,1,2,2-tetrachloroethane (2.55 g, 7.83 mmol) in THF (7.00 mL) was added, and the resulting mixture was stirred at −78° C. for 1 h. Saturated ammonium chloride solution was added dropwise at −78° C. and the reaction mixture was warmed to ambient temperature. The mixture was diluted with ethyl acetate (200 mL) and water (100 mL). The layers were separated and the ethyl acetate layer was washed with saturated sodium chloride solution, dried over sodium sulfate, filtered, and concentrated to a tan foam. Purification by flash column chromatography using ethyl acetate (containing 5% methanol) in hexanes (0-75%) gave the desired product (3.12 g, 61.5%) as a tan solid. LCMS for $C_{27}H_{26}BrN_4O_5S$ (M+H)$^+$: m/z=597.1, 599.1; Found: 597.1, 599.1.

Step 8. tert-Butyl 4-(4-methyl-8-(4-((4-(methylsulfonyl)piperidin-1-yl)methyl)phenyl)-3-oxo-7-(phenylsulfonyl)-1,3,4,7-tetrahydro-2H-pyrrolo[3',2':5,6]pyrido[3,4-d]pyrimidin-2-yl)benzoate

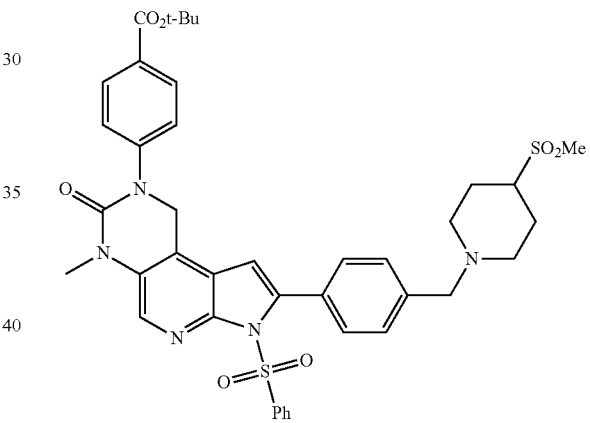

A mixture of tert-butyl 4-(8-bromo-4-methyl-3-oxo-7-(phenylsulfonyl)-1,3,4,7-tetrahydro-2H-pyrrolo[3',2':5,6]pyrido[3,4-d]pyrimidin-2-yl)benzoate (2.16 g, 3.62 mmol), 4-(methylsulfonyl)-1-(4-(4,4,5,5-tetramethyl-1,3,2-dioxaborolan-2-yl)benzyl)piperidine (1.65 g, 4.35 mmol), and cesium fluoride (2.75 g, 18.1 mmol) in 1,4-dioxane (45 mL) and water (6.00 mL) was degassed by bubbling with nitrogen for 10 min. Dichloro[1,1'-bis(dicyclohexylphosphino)ferrocene]palladium(II) (0.274 g, 0.362 mmol) (Pd127) was added and the mixture was degassed with nitrogen for 10 min, then refluxed at 110° C. for 8.5 h. The reaction mixture was diluted with EtOAc (50 mL) and filtered through a 0.45 micron filter cartridge. The filtrate was diluted with ethyl acetate (100 mL) and water (20 mL) and the layers were separated. The ethyl acetate layer was washed with saturated sodium chloride solution, dried over sodium sulfate, filtered, and concentrated to a dark brown foam. Purification by flash column chromatography using ethyl acetate (containing 5% methanol) in hexanes (0-100%) gave the desired product (2.07 g, 74.2%) as a rust colored foam. LCMS for $C_{40}H_{44}N_5O_7S_2$(M+H)$^+$: m/z=770.3; Found: 770.4.

Step 9. tert-Butyl 4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate

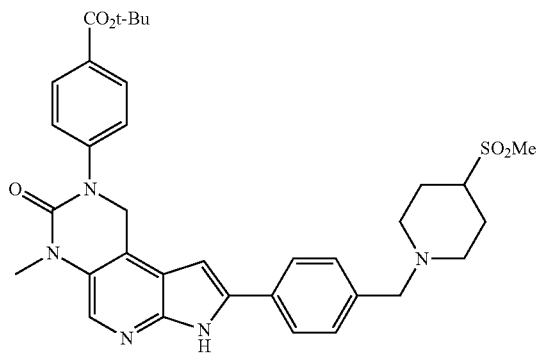 [SMILES: CN1C(=O)N(c2ccc(C(=O)OC(C)(C)C)cc2)Cc2c1cnc1[nH]c(-c3ccc(CN4CCC(S(C)(=O)=O)CC4)cc3)cc21]

To a solution of tert-butyl 4-(4-methyl-8-(4-((4-(methylsulfonyl)piperidin-1-yl)methyl)phenyl)-3-oxo-7-(phenylsulfonyl)-1,3,4,7-tetrahydro-2H-pyrrolo[3',2':5,6]pyrido[3,4-d]pyrimidin-2-yl)benzoate (2.02 g, 2.62 mmol) in THF (17.5 mL) and methanol (17.5 mL) at 0° C. was added a 3 M solution of potassium hydroxide (17.5 mL, 52.4 mmol) in water. The ice bath was removed and the thick suspension was stirred for 2 h. THF (15 mL) was added which dissolved some of the solids and produced a finer suspension. The reaction mixture was stirred for an additional 2 h, THF (5 mL) was added to dissolve all solids and the mixture was stirred for an additional 2.5 h. The mixture was diluted with dichloromethane (100 mL) and water (100 mL) and stirred until all solids dissolved. The mixture was transferred to a separatory funnel and the layers were separated. The aqueous layer was extracted with dichloromethane (100 mL) and the combined dichloromethane extracts were dried over sodium sulfate, filtered, and concentrated to afford the desired product (1.32 g, 80.0%) as a tan solid. LCMS for $C_{34}H_{40}N_5O_5S$ (M+H)$^+$: m/z=630.3; Found: 630.3.

Step 10. tert-Butyl 4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate

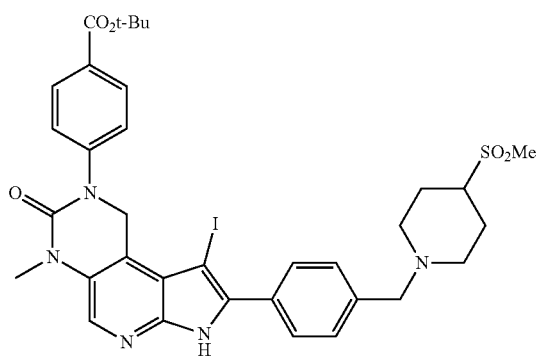 [SMILES: CN1C(=O)N(c2ccc(C(=O)OC(C)(C)C)cc2)Cc2c1cnc1[nH]c(-c3ccc(CN4CCC(S(C)(=O)=O)CC4)cc3)c(I)c21]

A suspension of tert-butyl 4-(4-methyl-8-(4-((4-(methylsulfonyl)piperidin-1yl)methyl)phenyl)-3-oxo-1,3,4,7-tetrahydro-2H-pyrrolo[3',2':5,6]pyrido[3,4-d]pyrimidin-2-yl)benzoate (1.32 g, 2.10 mmol) in THF (52.4 mL) was evacuated and refilled with nitrogen six times. NIS (0.707 g, 3.14 mmol) was added and the flask was evacuated and refilled with nitrogen six more times. The resulting suspension slowly became a solution after NIS addition. The mixture was stirred for 30 min and, while still under nitrogen, diluted with a solution of 10% sodium thiosulfate in water (20 mL) and ethyl acetate (100 mL). The mixture was stirred for 15 min under nitrogen, transferred to a separatory funnel with EtOAc (20 mL), and the layers were separated. The ethyl acetate layer was washed with saturated sodium bicarbonate solution and saturated sodium chloride solution. The ethyl acetate layer was then dried over sodium sulfate, filtered, and concentrated to provide the desired product (1.56 g, 98.5%) as a brown/orange solid. LCMS for $C_{34}H_{39}IN_5O_5S$ (M+H)$^+$: m/z=756.2; Found: 756.2.

Step 11. tert-Butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate

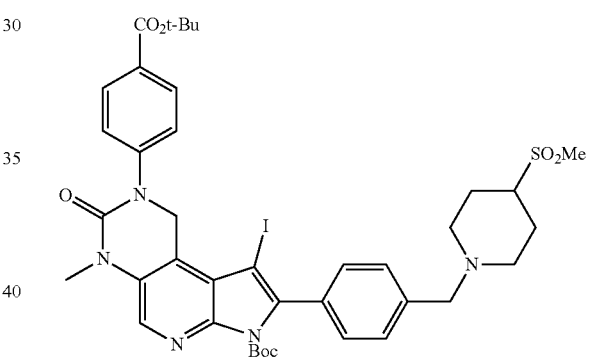

To a solution of tert-butyl 4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate (1.56 g, 2.06 mmol) in dichloromethane (27.4 mL) was added di-tert-butyl dicarbonate (1.35 g, 6.17 mmol) and 4-dimethylaminopyridine (0.126 g, 1.03 mmol). The mixture was stirred at ambient temperature for 1.5 h and was diluted with dichloromethane (100 mL). A mixture of water (50 mL)/saturated sodium bicarbonate solution (50 mL) was added and the layers were separated. The aqueous layer was extracted with additional dichloromethane (50 mL). The combined dichloromethane extracts were washed with saturated sodium chloride solution, dried over sodium sulfate, filtered, and concentrated to a brown foam. Purification by flash column chromatography using methanol in dichloromethane (0-10%) afforded the desired product (1.51 g, 86.0%) as a tan foam. LCMS for $C_{39}H_{47}IN_5O_7S$ (M+H)$^+$: m/z=856.2; Found: 856.1.

Step 12. tert-Butyl 2-(4-(tert-butoxycarbonyl)phenyl)-9-(4-methoxyphenyl)-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate Step 13. 4-(9-(4-Methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

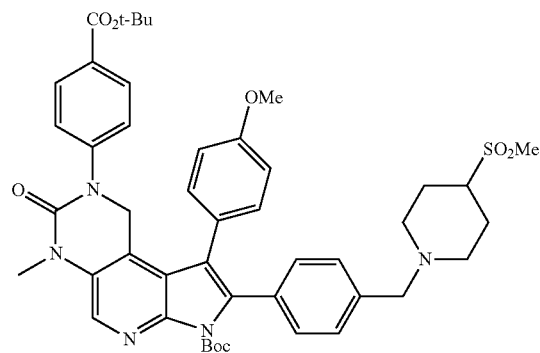 [SMILES: COc1ccc(-c2c(-c3ccc(CN4CCC(S(C)(=O)=O)CC4)cc3)n(C(=O)OC(C)(C)C)c3ncc4c(c23)CN(c2ccc(C(=O)OC(C)(C)C)cc2)C(=O)N4C)cc1]

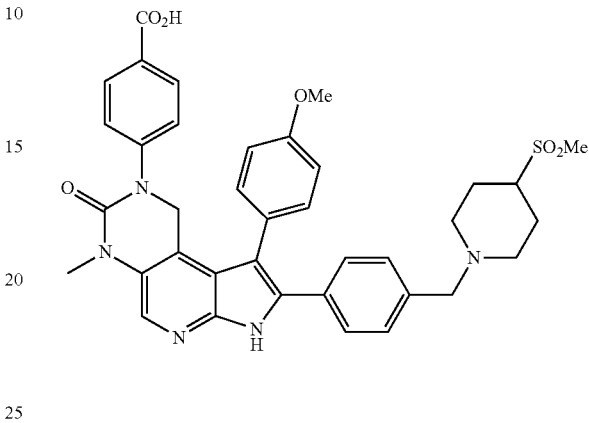

A solution of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (0.166 g, 0.194 mmol) and (4-methoxyphenyl)boronic acid (0.088 g, 0.582 mmol) in 1,4-dioxane (2.8 mL) was treated with a 1.0 M solution of potassium carbonate (0.970 mL, 0.970 mmol) in water. The mixture was bubbled with nitrogen for 5 min and was treated with dichloro[1,1'-bis(diphenylphosphino)ferrocene]palladium (II) dichloromethane adduct (0.024 g, 0.029 mmol). The mixture was bubbled with nitrogen for an additional 5 min and heated at 80° C. for 1.5 h. The reaction mixture was diluted with ethyl acetate (40 mL), filtered through a 0.45 micron filter cartridge, and the solids were rinsed with additional ethyl acetate (10 mL). The filtrate was washed with saturated sodium chloride solution (10 mL), dried over sodium sulfate, filtered, and concentrated to an orange foam. Purification by flash column chromatography using ethyl acetate (containing 5% methanol) in hexanes (0-100%) afforded the desired product (0.141 g, 87.0%) as a slightly tan solid. LCMS for $C_{46}H_{54}N_5O_8S$ (M+H)$^+$: m/z=836.4; Found: 836.5.

To a solution of tert-butyl 2-(4-(tert-butoxycarbonyl)phenyl)-9-(4-methoxyphenyl)-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (0.141 g, 0.169 mmol) in dichloromethane (1.69 mL) was added trifluoroacetic acid (1.69 mL, 21.9 mmol), dropwise, and the resulting solution was stirred for 1.5 h. The solution was concentrated and reconcentrated from acetonitrile (4×) to provide the desired product (0.145 g, >100%) as a brown solid, which was used in the next step without further purification. LCMS for $C_{37}H_{38}N_5O_6S$ (M+H)$^+$: m/z=680.3; Found: 680.3.

Step 14. 4-(9-(4-Methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-(pyridin-3-yl)benzamide Bistrifluoroacetic Acid Salt A solution of 4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid, trifluoroacetic acid salt (0.006 g, 7.56 µmol) and triethylamine (10.5 µL, 0.076 mmol) in N,N-dimethylformamide (0.300 mL) was treated with 3-aminopyridine (3.56 mg, 0.038 mmol) and HATU (4.31 mg, 0.011 mmol). The resulting mixture was stirred for 3 h. The reaction mixture was diluted with acetonitrile and water and was acidified with trifluoroacetic acid. The solution was purified via preparative LCMS (XBridge C18 Column, eluting with a gradient of acetonitrile in water with 0.1% trifluoroacetic acid, at flow rate of 60 mL/min) to afford the desired product (3.4 mg, 45.7%) as a yellow tinted solid. LCMS for $C_{42}H_{42}N_7O_5S$ (M+H)$^+$: m/z=756.3; Found: 756.3.

Example 12

Example 12 of Table 3 was prepared according to the procedures described in Example 11.

TABLE 3

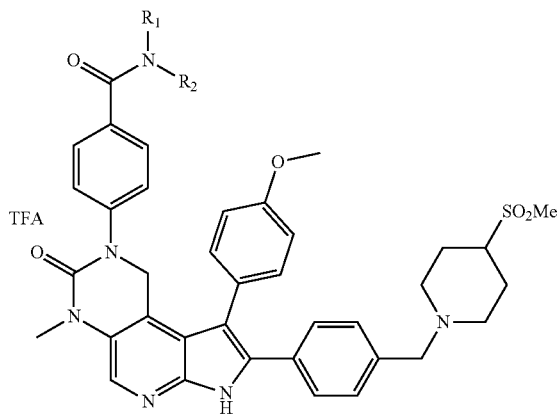

| Ex. No. | Name | R₁ | R₂ | LCMS [M + H]⁺ | ¹H NMR Spectrum |
|---|---|---|---|---|---|
| 12 | 4-(9-(4-methoxyphenyl)-4-methyl-8-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-methylbenzamide, trifluroacetate | CH₃ | H | 693.3 | $^1$H NMR (400 MHz, DMSO-d$_6$) δ 12.26 (s, 1H), 9.44-9.39 (m, 1H), 8.42-8.35 (m, 1H), 8.19 (s, 1H), 7.74 (d, J = 8.5 Hz, 2H), 7.57 (d, J = 8.0 Hz, 2H), 7.44 (d, J = 8.0 Hz, 2H), 7.29 (d, J = 8.5 Hz, 2H), 7.11 (d, J = 8.6 Hz, 2H), 7.00 (d, J = 8.6 Hz, 2H), 4.51 (s, 2H), 4.31-4.25 (m, 2H), 3.82 (s, 3H), 3.52 (d, J = 12.1 Hz, 2H), 3.45-3.32 (m, 4H), 3.05-2.90 (m, 5H), 2.81-2.76 (m, 3H), 2.24 (d, J = 13.8 Hz, 2H), 1.91-1.77 (m, 2H). |

Example 13. N-(2-(2-Benzylhydrazineyl)-2-oxo-ethyl)-4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2': 5,6]pyrido[3,4-d]pyrimidin-2-yl)benzamide, TFA

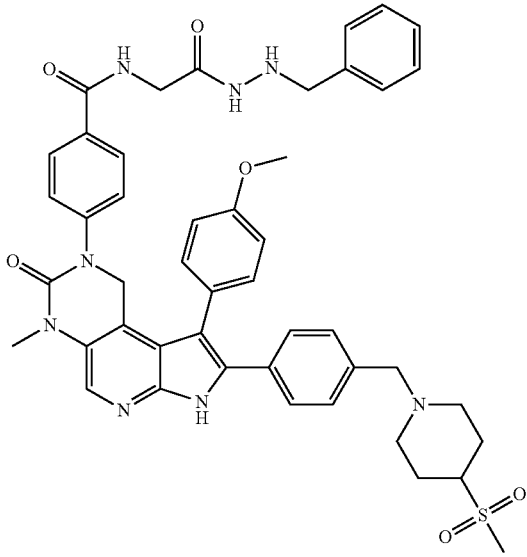 [SMILES: COc1ccc(-c2c(-c3ccc(CN4CCC(S(C)(=O)=O)CC4)cc3)[nH]c3ncc4c(c23)CN(c2ccc(C(=O)NCC(=O)NNCc3ccccc3)cc2)C(=O)N4C)cc1]

Step 1. tert-Butyl (4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoyl)glycinate

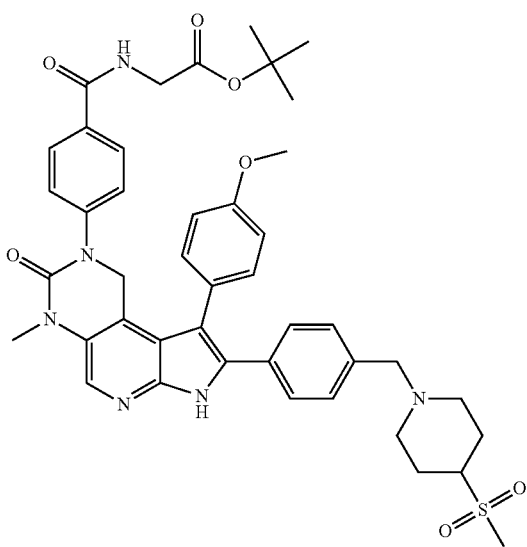 [SMILES: COc1ccc(-c2c(-c3ccc(CN4CCC(S(C)(=O)=O)CC4)cc3)[nH]c3ncc4c(c23)CN(c2ccc(C(=O)NCC(=O)OC(C)(C)C)cc2)C(=O)N4C)cc1]

The title compound was prepared according to the procedures described in Example 11, Step 14, using tert-butyl glycinate in place of 3-aminopyridine as the starting material. LCMS for $C_{43}H_{49}N_6O_7S$ (M+H)$^+$: m/z=793.3; Found: 793.3.

Step 2. (4-(9-(4-Methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoyl)glycine Trifluoroacetic Acid Salt

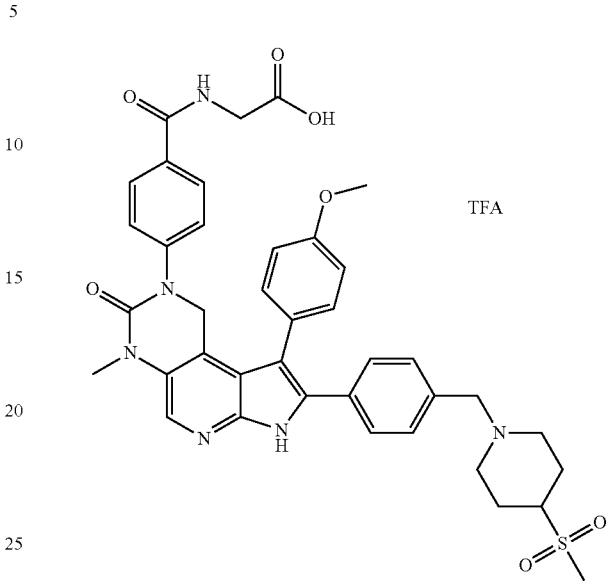

The title compound was prepared according to the procedures described in Example 11, Step 13, using tert-butyl (4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoyl)glycinate in place of tert-butyl 2-(4-(tert-butoxycarbonyl)phenyl)-9-(4-methoxyphenyl)-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate as the starting material. LCMS for $C_{39}H_{41}N_6O_7S$ (M+H)$^+$: m/z=737.3; Found: 737.3.

Step 3. tert-Butyl 1-benzylhydrazine-1-carboxylate

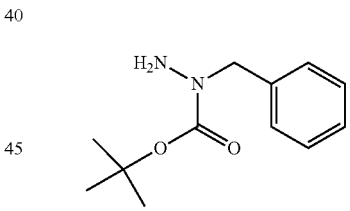

A solution of benzylhydrazine, 2HCl (0.350 g, 1.79 mmol) in THF (8.97 mL) was treated with Boc-anhydride (0.458 mL, 1.97 mmol) followed by dropwise addition of a solution of sodium bicarbonate (0.603 g, 7.18 mmol) in water (4.69 mL, 260 mmol), and the resulting mixture was stirred for 14 h. The reaction mixture was diluted with EtOAc (50 mL), water (10 mL), and sat. NaHCO$_3$ solution (20 mL). The organic layer was separated and washed with sat. NaCl solution, dried over anhydrous sodium sulfate, filtered, and concentrated to a tan oil. Purification by flash column chromatography using MTBE in hexanes (0-100%) afforded the desired product (384 mg, 96.2%) as a colorless oil containing ~10% of tert-butyl 2-benzylhydrazine-1-carboxylate. The product was further purified by preparative LCMS (XBridge® C18 column, eluting with a gradient of acetonitrile/water 0.1% ammonium hydroxide, at flow rate of 60 mL/min) to remove the tert-butyl 2-benzylhydrazine-1-carboxylate. LCMS for $C_8H_{11}N_2O_2$(M+H)$^+$: m/z=167.2; Found: 167.1.

Step 4. N-(2-(2-Benzylhydrazineyl)-2-oxoethyl)-4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzamide Trifluoroacetic Acid Salt

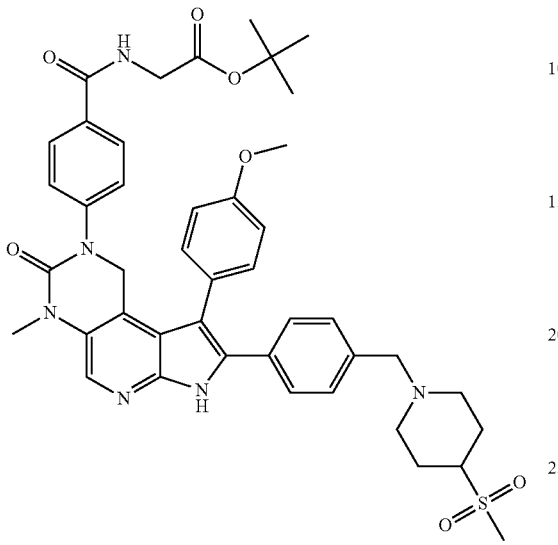

The title compound was prepared according to the procedure described in Example 11, Step 14, using (4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoyl) glycine trifluoroacetic acid in place of 4-(9-(4-methoxyphenyl)-4-methyl-8-(4-((4-(methylsulfonyl) piperidin-1-yl)methyl)phenyl)-3-oxo-1,3,4,7-tetrahydro-2H-pyrrolo[3',2':5,6]pyrido[3,4-d]pyrimidin-2-yl)benzoic acid, trifluoroacetic acid salt and tert-butyl 1-benzylhydrazine-1-carboxylate in place of 3-aminopyridine as the starting materials. LCMS for $C_{46}H_{49}N_8O_6S$ $(M+H)^+$: m/z=841.3; Found: 841.3.

Example 14. 4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-((1-cyanocyclopropyl)methyl)benzamide Trifluoroacetic Acid

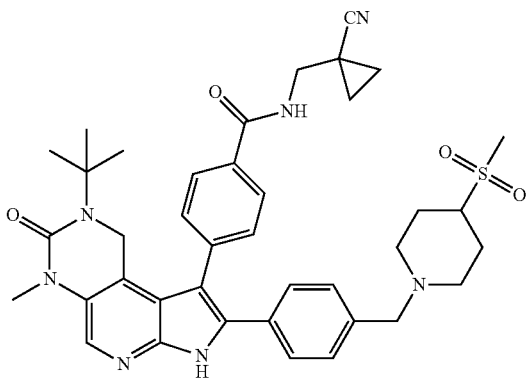 [SMILES: CN1C(=O)N(C(C)(C)C)Cc2c1cnc1[nH]c(-c3ccc(CN4CCC(S(C)(=O)=O)CC4)cc3)c(-c3ccc(C(=O)NCC4(C#N)CC4)cc3)c21]

Step 1. 2-Methyl-N-((5-nitro-1-(phenylsulfonyl)-1H-pyrrolo[2,3-b]pyridin-4-yl)methyl)propan-2-amine

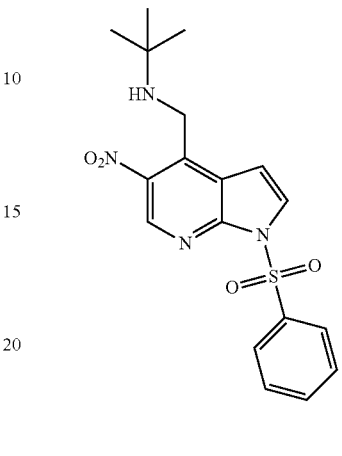

The title compound was prepared according to the procedures described in Example #11, Step 3, using tert-butylamine as the starting material in place of tert-butyl 4-aminobenzoate. LCMS for $C_{18}H_{21}N_4O_4S$ $(M+H)^+$: m/z=389.1; Found: 389.1.

Step 2. 4-(((tert-Butylamino)methyl)-1-(phenylsulfonyl)-1H-pyrrolo[2,3-b]pyridin-5-amine

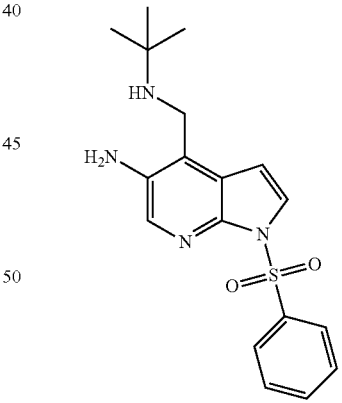

The title compound was prepared according to the procedures described in Example 11, Step 4, using 2-methyl-N-((5-nitro-1-(phenylsulfonyl)-1H-pyrrolo[2,3-b]pyridin-4-yl)methyl)propan-2-amine as the starting material in place of tert-butyl 4-(((5-nitro-1-(phenylsulfonyl)-1H-pyrrolo[2,3-b]pyridin-4-yl)methyl)amino)benzoate. LCMS for $C_{18}H_{23}N_4O_2S$ $(M+H)^+$: m/z=359.2; Found: 359.1.

Step 3. 2-(tert-Butyl)-7-(phenylsulfonyl)-1,2,4,7-tetrahydro-3H-pyrrolo[3',2':5,6]pyrido[3,4-d]pyrimidin-3-one Step 5. 8-Bromo-2-(tert-butyl)-4-methyl-7-(phenylsulfonyl)-1,2,4,7-tetrahydro-3H-pyrrolo[3',2':5,6]pyrido[3,4-d]pyrimidin-3-one

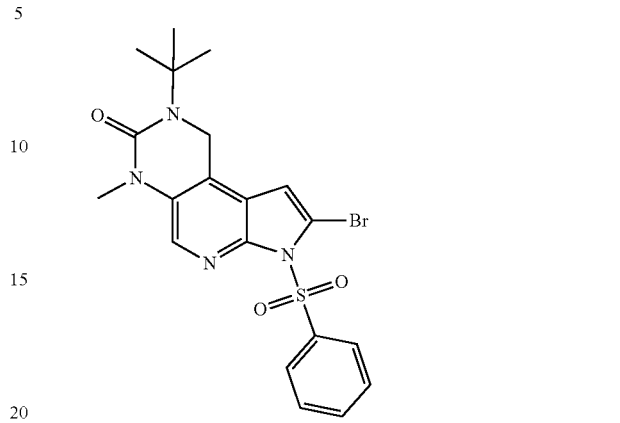

The title compound was prepared according to the procedures described in Example 11, Step 7, using 2-(tert-butyl)-4-methyl-7-(phenylsulfonyl)-1,2,4,7-tetrahydro-3H-pyrrolo[3',2':5,6]pyrido[3,4-d]pyrimidin-3-one as the starting material in place of tert-butyl 4-(4-methyl-3-oxo-7-(phenylsulfonyl)-1,3,4,7-tetrahydro-2H-pyrrolo[3',2':5,6]pyrido[3,4-d]pyrimidin-2-yl)benzoate. LCMS for $C_{20}H_{22}BrN_4O_3S$ (M+H)$^+$: m/z=477.1, 479.1; Found: 477.0, 479.1.

Step 6. 2-(tert-Butyl)-4-methyl-8-(4-((4-((methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one

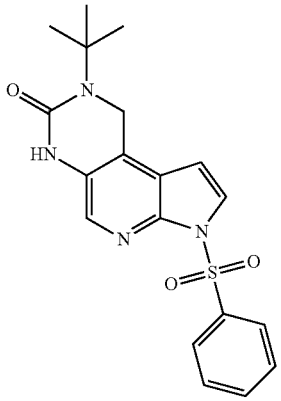 [SMILES: CC(C)(C)N1Cc2c(cnc3c2ccn3S(=O)(=O)c2ccccc2)NC1=O]

The title compound was prepared according to the procedures described in Example 11, Step 5, using 4-(((tert-butylamino)methyl)-1-(phenylsulfonyl)-1H-pyrrolo[2,3-b]pyridin-5-amine as the starting material in place of tert-butyl 4-(((5-amino-1-(phenylsulfonyl)-1H-pyrrolo[2,3-b]pyridin-4-yl)methyl)amino)benzoate. LCMS for $C_{19}H_{21}N_4O_3S$ (M+H)$^+$: m/z=385.1; Found: 385.1.

Step 4. 2-(tert-Butyl)-4-methyl-7-(phenylsulfonyl)-1,2,4,7-tetrahydro-3H-pyrrolo[3',2':5,6]pyrido[3,4-d]pyrimidin-3-one

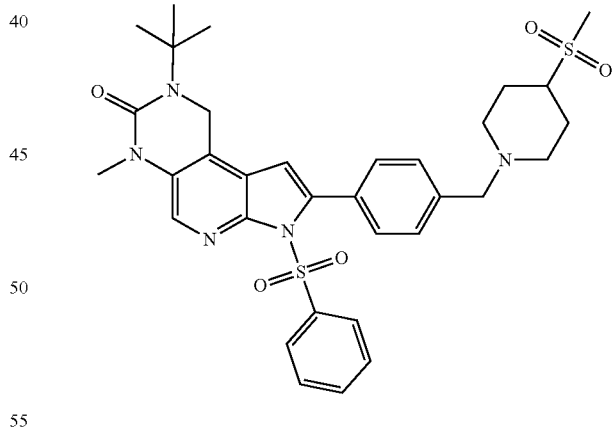

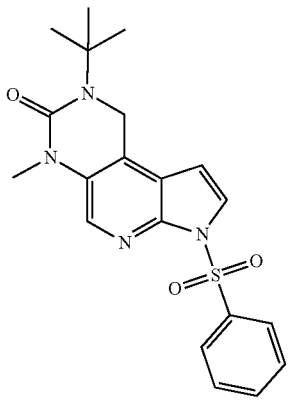 [SMILES: CN1C(=O)N(C(C)(C)C)Cc2c1cnc1c2ccn1S(=O)(=O)c1ccccc1]

The title compound was prepared according to the procedures described in Example 11, Step 6, using 2-(tert-butyl)-7-(phenylsulfonyl)-1,2,4,7-tetrahydro-3H-pyrrolo[3',2':5,6]pyrido[3,4-d]pyrimidin-3-one as the starting material in place of tert-butyl 4-(3-oxo-7-(phenylsulfonyl)-1,3,4,7-tetrahydro-2H-pyrrolo[3',2':5,6]pyrido[3,4-d]pyrimidin-2-yl)benzoate. LCMS for $C_{20}H_{23}N_4O_3S$ (M+H)$^+$: m/z=399.1; Found: 399.1.

The title compound was prepared according to the procedures described in Example 11, Step 8, using 8-bromo-2-(tert-butyl)-4-methyl-7-(phenylsulfonyl)-1,2,4,7-tetrahydro-3H-pyrrolo[3',2':5,6]pyrido[3,4-d]pyrimidin-3-one as the starting material in place of tert-butyl 4-(8-bromo-4-methyl-3-oxo-7-(phenylsulfonyl)-1,3,4,7-tetrahydro-2H-pyrrolo[3',2':5,6]pyrido[3,4-d]pyrimidin-2-yl)benzoate. LCMS for $C_{33}H_{40}N_5O_5S_2$ (M+H)$^+$: m/z=650.2; Found: 650.3.

Step 7. 2-(tert-Butyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

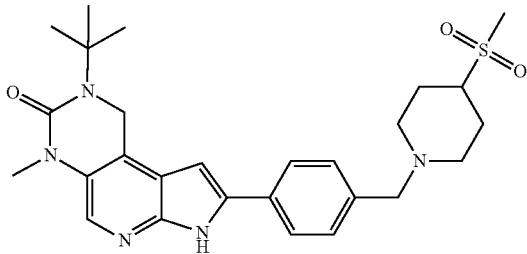 [SMILES: CN1C(=O)N(C(C)(C)C)Cc2c1cnc1[nH]c(-c3ccc(CN4CCC(S(C)(=O)=O)CC4)cc3)cc21]

The title compound was prepared according to the procedures described in Example 11, Step 9, using 2-(tert-butyl)-4-methyl-8-(4-((4-(methylsulfonyl)piperidin-1-yl)methyl)phenyl)-7-(phenylsulfonyl)-1,2,4,7-tetrahydro-3H-pyrrolo[3',2':5,6]pyrido[3,4-d]pyrimidin-3-one as the starting material in place of tert-butyl 4-(4-methyl-8-(4-((4-(methylsulfonyl)piperidin-1-yl)methyl)phenyl)-3-oxo-7-(phenylsulfonyl)-1,3,4,7-tetrahydro-2H-pyrrolo[3',2':5,6]pyrido[3,4-d]pyrimidin-2-yl)benzoate. LCMS for $C_{27}H_{36}N_5O_3S$ (M+H)$^+$: m/z=510.3; Found: 510.3.

Step 8. 2-(tert-Butyl)-9-iodo-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one

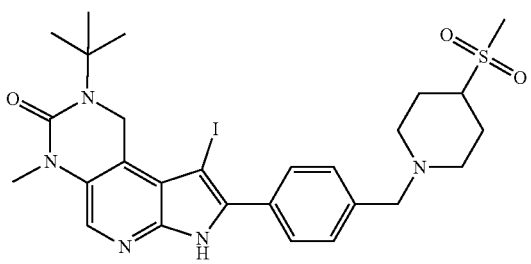

To a solution of 2-(tert-butyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one (0.238 g, 0.467 mmol) and N,N-diisopropylethylamine (0.245 mL, 1.401 mmol) in DMF (3.11 mL) was added NIS (0.158 g, 0.700 mmol). The reaction mixture was stirred at room temperature for 40 minutes, then additional NIS (0.026 g, 0.25 eq) was added. The mixture was stirred at room temperature for 1 h. 10% Sodium bisulfate was added to reaction mixture, followed by deionized water, sat. aq. sodium bicarbonate solution, and ethyl acetate. The product was extracted with ethyl acetate (3×). The combined extracts were washed with brine, then dried over magnesium sulfate, filtered, and concentrated to a brown solid. Methanol (5.0 mL) was added and the resulting mixture was stirred for 3 h. The solids were isolated by filtration and washed with methanol (2×2.0 mL). Air was pulled through the solids for 15 min and the solids were placed on high vacuum for 2 h to afford the desired product (181 mg, 60.9%) as a light tan solid. LCMS for $C_{27}H_{35}IN_5O_3S$ (M+H)$^+$: m/z=636.1; Found: 636.1.

Step 9. tert-Butyl 2-(tert-butyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate

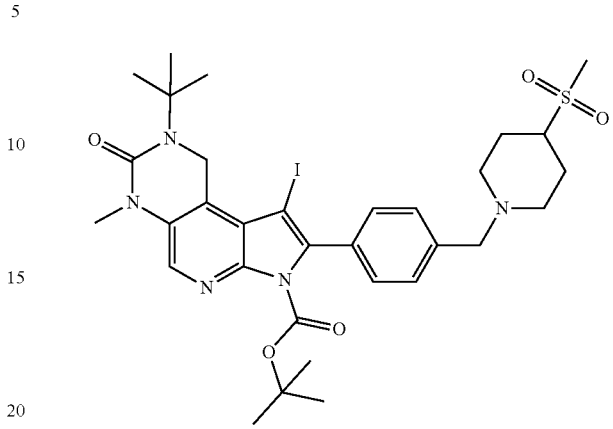

The title compound was prepared according to the procedures described in Example 11, Step 11, using 2-(tert-butyl)-9-iodo-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one as the starting material in place of tert-butyl 4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate. LCMS for $C_{32}H_{43}IN_5O_5S$ (M+H)$^+$: m/z=736.2; Found: 736.3.

Step 10. tert-Butyl 2-(tert-butyl)-9-(4-(methoxycarbonyl)phenyl)-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate

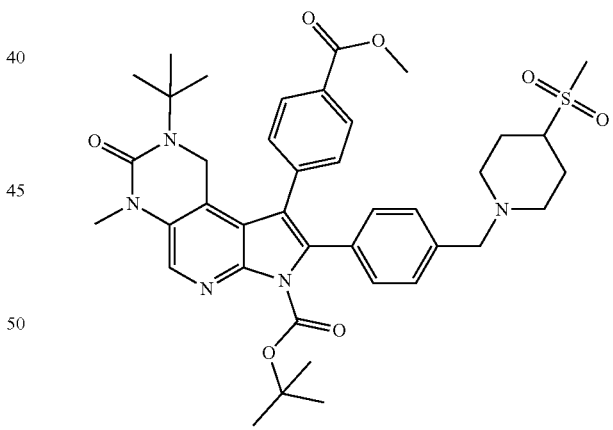

A vial containing dichloro[1,1'-bis(diphenylphosphino)ferrocene]palladium (II) dichloromethane adduct (3.33 mg, 4.08 μmol) and methyl 4-(4,4,5,5-tetramethyl-1,3,2-dioxaborolan-2-yl)benzoate (0.014 g, 0.054 mmol) was charged with a solution of tert-butyl 2-(tert-butyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (0.020 g, 0.027 mmol) in 1,4-dioxane (0.544 mL), followed by 1.0 M potassium carbonate in water (0.082 mL, 0.082 mmol). The mixture was bubbled with nitrogen for 5 min and the sealed vial was heated at 80° C. for 6 h. The reaction mixture was diluted with ethyl acetate and filtered through a 0.45 micron filter cartridge. The solids were rinsed with ethyl acetate and the filtrate was concentrated to a brown oil. Purification by flash column chromatography using ethyl acetate (containing 5% methanol) in hexanes (0% to 100%) afforded the desired product (15 mg, 74.3%) as a brown oil. LCMS for $C_{40}H_{50}N_5O_7S$ $(M+H)^+$: m/z=744.3; Found: 744.4.

Step 11. 4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzoic acid

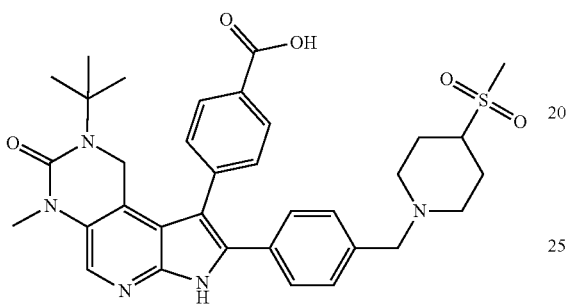

A solution of tert-butyl 2-(tert-butyl)-9-(4-(methoxycarbonyl)phenyl)-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (15 mg, 0.020 mmol) in dry THF (0.50 mL) was treated with sodium methoxide (25 wt % in methanol, 0.025 mL, 0.109 mmol). The mixture was stirred at room temp for 40 min. Methanol (0.5 mL) was added to reaction mixture, followed by sodium hydroxide (1.0 N in water, 0.136 mL, 0.136 mmol) and the resulting mixture was stirred at room temp for 18 h. 1 N HCl (~0.3 mL) was added, bringing reaction mixture to pH 5-6. The mixture was then concentrated and placed on high vacuum overnight to afford the desired product (30 mg) as an impure tan solid that contained inorganic salts. LCMS for $C_{34}H_{40}N_5O_5S$ $(M+H)^+$: m/z=630.3; Found: 630.3.

Step 12. 4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-((1-cyanocyclopropyl)methyl)benzamide Trifluoroacetic Acid Salt A mixture of 4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzoic acid (9.9 mg, 42.3 wt %, 6.67 µmol), 1-(aminomethyl)cyclopropane-1-carbonitrile, hydrochloride (2.65 mg, 0.020 mmol), and HATU (3.80 mg, 10.00 µmol) in DMF (0.167 mL) was treated with triethylamine (5.58 µL, 0.040 mmol). The reaction mixture was stirred at room temperature for 40 minutes, then methanol and deionized water were added to the reaction mixture. The resulting solution was purified via preparative LCMS (XBridge C18 Column, eluting with a gradient of acetonitrile in water with 0.1% trifluoroacetic acid, at flow rate of 60 mL/min) to afford the desired product (2.8 mg, 51.1%) as a yellow solid. $^1$H NMR (400 MHz, DMSO-d$_6$) δ 12.30 (s, 1H), 9.41 (s, 1H), 8.99 (s, 1H), 8.07 (s, 1H), 8.01 (d, J=7.9 Hz, 2H), 7.57-7.49 (m, 4H), 7.45 (d, J=8.1 Hz, 2H), 4.28 (s, 2H), 4.02 (s, 2H), 3.28 (s, 3H), 2.99 (s, 3H), 2.24 (d, J=13.8 Hz, 2H), 1.84 (d, J=13.3 Hz, 2H), 1.28-1.22 (m, 2H), 1.16 (t, J=3.4 Hz, 2H), 1.10 (s, 9H). LCMS for $C_{39}H_{46}N_7O_4S$ $(M+H)^+$: m/z=708.3; Found: 708.3.

Example 15. 4-(9-(Methoxycarbonyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

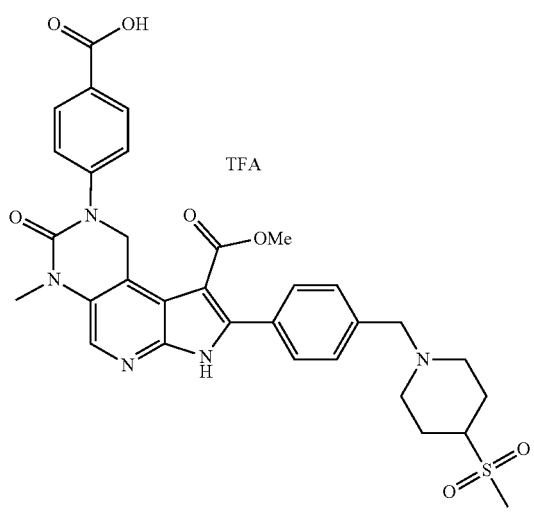 [SMILES: COC(=O)c1c(-c2ccc(CN3CCC(S(C)(=O)=O)CC3)cc2)[nH]c2ncc3c(c12)CN(c1ccc(C(=O)O)cc1)C(=O)N3C]

A solution of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (Example 11, Step 11, 0.008 g, 9.35 µmol), triethylamine (6.51 µL, 0.047 mmol), and dichloro[1,1'-bis(diphenylphosphino)ferrocene]palladium (II) dichloromethane adduct (1.145 mg, 1.402 µmol) in methanol (0.234 mL) was bubbled with nitrogen for 5 min and then bubbled with carbon monoxide for 5 min. The reaction mixture was stirred at 65° C. overnight, cooled to RT, and diluted with ethyl acetate. The reaction mixture was filtered through a 0.45 micron filter cartridge that was rinsed with ethyl acetate. The filtrate was concentrated to a brown oil, which was then dissolved in DCM (0.50 mL) and TFA (0.50 mL) and stirred for 40 min. The reaction mixture was concentrated and purified via preparative LCMS (XBridge C18 Column, eluting with a gradient of acetonitrile in water with 0.1% trifluoroacetic acid, at flow rate of 60 mL/min) to afford the desired product (1.70 mg, 23.1%). LCMS for $C_{32}H_{34}N_5O_7S$ (M+H)$^+$: m/z=632.2; Found: 632.2.

Example 16. N-(4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzyl)acetamide

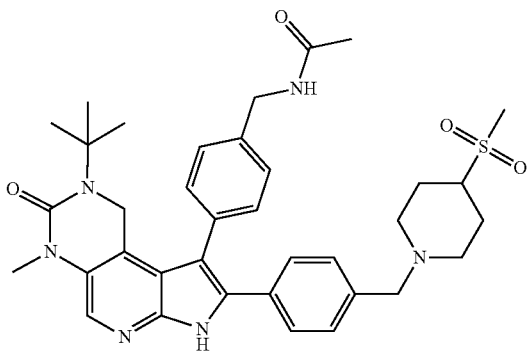 [SMILES: CC(=O)NCc1ccc(-c2c(-c3ccc(CN4CCC(S(C)(=O)=O)CC4)cc3)[nH]c3ncc4c(c23)CN(C(C)(C)C)C(=O)N4C)cc1]

Step 2. N-(4-(4,4,5,5-Tetramethyl-1,3,2-dioxaborolan-2-yl)benzyl)acetamide

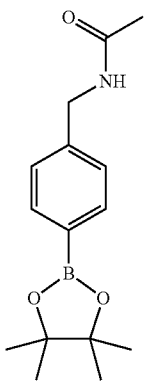 [SMILES: CC(=O)NCc1ccc(B2OC(C)(C)C(C)(C)O2)cc1]

A solution of 4-dimethylaminopyridine (1.048 mg, 8.58 μmol) and (4-(4,4,5,5-tetramethyl-1,3,2-dioxaborolan-2-yl)phenyl)methanamine (0.020 g, 0.086 mmol) [Combi-Blocks, cat #PN-2443] in dichloromethane (0.572 mL) and triethylamine (0.018 mL, 0.129 mmol) was treated with acetic anhydride (0.024 mL, 0.257 mmol), and the mixture was stirred at room temp over a weekend. Purification of the reaction mixture by flash column chromatography using methanol in dichloromethane (0% to 20%) afforded the desired product (18 mg, 76.3%) as an oily white solid. LCMS for $C_{15}H_{23}BNO_3$ (M+H)$^+$: m/z=276.2; Found: 276.3.

Step 2. N-(4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzyl)acetamide A solution of tert-butyl 2-(tert-butyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (6.0 mg, 8.16 μmol), N-(4-(4,4,5,5-tetramethyl-1,3,2-dioxaborolan-2-yl)benzyl)acetamide (6.73 mg, 0.024 mmol), and dichloro[1,1'-bis(diphenylphosphino)ferrocene]palladium (II) dichloromethane adduct (0.999 mg, 1.22 μmol) in 1,4-dioxane (0.181 mL), and potassium carbonate (1.0 M in water, 0.041 mL, 0.041 mmol) was bubbled with nitrogen for 5 min. The sealed vial was heated at 80° C. for 6 h, then cooled to room temperature and held overnight. Ethyl acetate was added to the reaction mixture, which was then filtered through a 0.45 micron filter cartridge. The solids were rinsed with ethyl acetate and the filtrate was concentrated to a brown oil. The oil was dissolved in dry THF (0.50 mL), sodium methoxide (25 wt % in methanol, 0.028 mL, 0.12 mmol) was added, and the mixture was stirred at room temp for 30 minutes. The mixture was then diluted with methanol, deionized water, and 1 N HCl (0.1 mL). The resulting solution was purified via preparative LCMS (XBridge C18 Column, eluting with a gradient of acetonitrile in water with 0.1% trifluoroacetic acid, at flow rate of 60 mL/min) to afford a crude material. The crude material was purified via preparative LCMS (XBridge C18 Column, eluting with a gradient of acetonitrile in water with 0.1% ammonium hydroxide, at flow rate of 60 mL/min) to afford the desired product (2.3 mg, 42.9%) as a white solid. $^1$H NMR (400 MHz, DMSO-d$_6$) δ 12.04 (s, 1H), 8.42 (t, J=6.2 Hz, 1H), 7.99 (s, 1H), 7.41 (d, J=8.1 Hz, 2H), 7.32 (s, 4H), 7.22 (d, J=8.1 Hz, 2H), 4.32 (d, J=6.1 Hz, 2H), 3.96 (s, 2H), 3.45 (s, 2H), 3.26 (s, 3H), 3.04 (t, J=12.4 Hz, 1H), 2.91 (s, 3H), 2.89 (s, 2H), 2.00-1.93 (m, 4H), 1.90 (s, 3H), 1.66-1.53 (m, 2H), 1.11 (s, 9H). LCMS for $C_{36}H_{45}N_6O_4S$ (M+H)$^+$: m/z=657.3; Found: 657.3.

Examples 17-18

Examples 17-18 of Table 4 were prepared according to procedures described in Example 16.

TABLE 4

| Ex. No. | Name | R | LCMS [M + H]+ | 1H NMR Spectrum |
|---|---|---|---|---|
| 17 | 4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-methylbenzenesulfonamide, trifluoroacetic acid salt | | 679.2 | — |
| 18 | 9-(4-(4-Acetylpiperazin-1-yl)phenyl)-2-(tert-butyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one, trifluoroacetic acid salt | | 712.4 | 1H NMR (400 MHz, DMSO-d6) δ 12.11 (s, 1H), 9.45 (s, 1H), 8.02 (s, 1H), 7.60 (d, J = 8.1 Hz, 2H), 7.43 (d, J = 7.9 Hz, 2H), 7.26 (d, J = 8.4 Hz, 2H), 7.07 (d, J = 8.6 Hz, 2H), 4.27 (s, 2H), 4.02 (s, 2H), 3.26 (s, 3H), 3.21 (t, J = 5.4 Hz, 2H), 3.15 (t, J = 5.2 Hz, 2H), 2.99 (s, 3H), 2.25 (d, J = 13.8 Hz, 2H), 2.07 (s, 3H), 1.84 (q, J = 13.0 Hz, 2H), 1.13 (s, 9H). |

Example 19. 2-(4-(4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)phenyl)-1H-pyrazol-1-yl)propanamide Trifluoroacetic Acid Salt

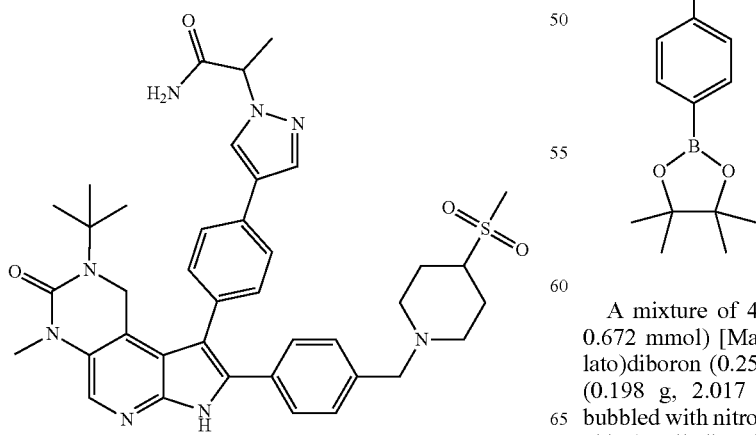

Step 1. 4-(4-(4,4,5,5-Tetramethyl-1,3,2-dioxaborolan-2-yl)phenyl)-1H-pyrazole

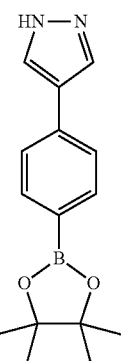

A mixture of 4-(4-bromophenyl)-1H-pyrazole (0.150 g, 0.672 mmol) [Matrix Scientific, cat #016087], bis(pinacolato)diboron (0.256 g, 1.009 mmol), and potassium acetate (0.198 g, 2.017 mmol) in 1,4-dioxane (4.48 mL) was bubbled with nitrogen for 5 min. Dichlorobis(triphenylphosphine)-palladium(II) (0.071 g, 0.101 mmol) was added and the resulting mixture was bubbled with nitrogen for an additional 5 min. The mixture was then heated in a sealed vial at 110° C. for 18 h. THF was added, and the reaction mixture was filtered. The solids were rinsed with additional THF and the filtrate was concentrated to a hazy yellow oil. Purification by flash column chromatography using ethyl acetate in hexanes (0% to 100%) afforded the desired product (136 mg, 74.9%) as a gummy white solid. LCMS for $C_{15}H_{20}BN_2O_2(M+H)^+$: m/z=271.2; Found: 271.1.

Step 2. 2-(4-(4-(2-(tert-Butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)phenyl)-1H-pyrazol-1-yl)propanamide Trifluoroacetic Acid Salt

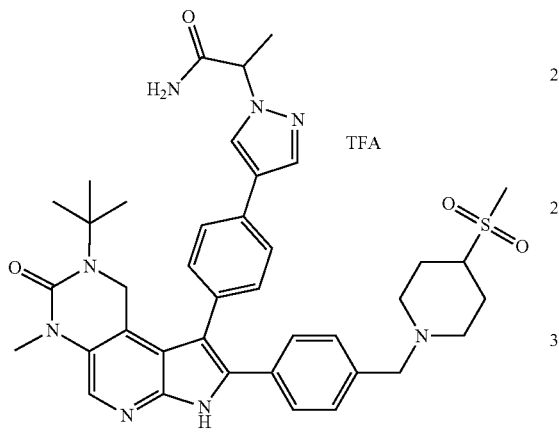

A mixture of 2-bromopropionamide (5.06 mg, 0.033 mmol), 4-(4-(4,4,5,5-tetramethyl-1,3,2-dioxaborolan-2-yl)phenyl)-1H-pyrazole (0.009 g, 0.033 mmol), and cesium carbonate (0.033 g, 0.100 mmol) in dry acetonitrile (0.133 mL) was heated in sealed vial at 75° C. for 17 h. The mixture was cooled to room temperature and concentrated. To the residue was added dichloro[1,1'-bis(diphenylphosphino)ferrocene]palladium (II) dichloromethane adduct (0.999 mg, 1.22 µmol), followed by a solution of tert-butyl 2-(tert-butyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (6.0 mg, 8.16 µmol) in 1,4-dioxane (0.181 mL) and potassium carbonate (1.0 M in water, 0.041 mL, 0.041 mmol). The mixture was bubbled with nitrogen for 5 min and heated in a sealed vial at 80° C. for 6 h. Ethyl acetate was added and the reaction mixture was filtered through a 0.45 micron filter cartridge. The solids were rinsed with additional ethyl acetate and the filtrate was concentrated. The resulting residue was dissolved in dry THF (0.50 mL), sodium methoxide (25 wt % in methanol, 0.019 mL, 0.082 mmol) was added, and the mixture was stirred at room temp for 20 min. Methanol, deionized water, and 1 N HCl (~0.1 mL) were added, and the resulting solution was purified via preparative LCMS (XBridge C18 Column, eluting with a gradient of acetonitrile in water with 0.1% trifluoroacetic acid, at flow rate of 60 mL/min) to afford the racemic desired product (0.9 mg, 13.2%) as a yellow solid. LCMS for $C_{39}H_{47}N_8O_4S$ $(M+H)^+$: m/z=723.3; Found: 723.2.

Example 20. 4-(9-(1-Acetyl-1,2,3,6-tetrahydropyridin-4-yl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

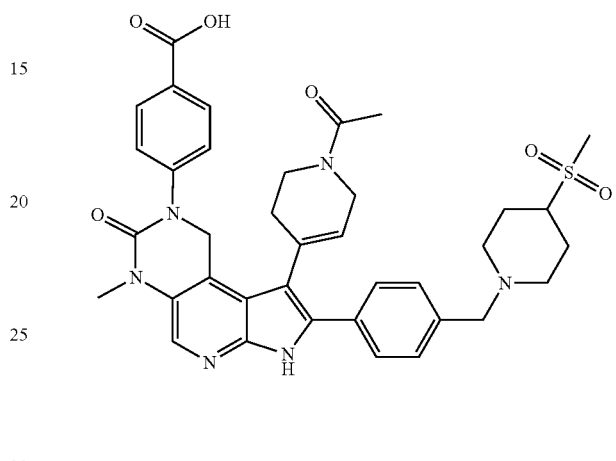

A mixture of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (Example 11, Step 11, 8.0 mg, 9.35 µmol), dichloro[1,1'-bis(diphenylphosphino)ferrocene]palladium (II) dichloromethane adduct (1.15 mg, 1.40 µmol), and 1-(4-(4,4,5,5-tetramethyl-1,3,2-dioxaborolan-2-yl)-3,6-dihydropyridin-1(2H)-yl)ethan-1-one (7.04 mg, 0.028 mmol) was stirred in 1,4-dioxane (0.21 mL) and potassium carbonate (1.0 M in water, 0.047 mL, 0.047 mmol). The mixture was bubbled with nitrogen for 5 min and heated in a sealed vial at 80° C. for 6 h. The mixture was diluted with ethyl acetate and filtered through a 0.45 micron filter cartridge. The solids were rinsed with additional ethyl acetate and concentrated. The resulting residue was dissolved in dichloromethane (0.50 mL), TFA (0.50 mL) was added, and the resulting mixture was stirred at room temp for 45 min, and then concentrated. The residue was dissolved in methanol and deionized water. The resulting solution was purified via preparative LCMS (XBridge C18 Column, eluting with a gradient of acetonitrile in water with 0.1% trifluoroacetic acid, at flow rate of 60 mL/min) to afford the desired product (6.2 mg, 81.8%) as a light tan solid. $^1$H NMR (400 MHz, DMSO-d$_6$) δ 12.22 (s, 1H), 9.59 (s, 1H), 8.18 (s, 1H), 7.95 (dd, J=8.4, 5.5 Hz, 2H), 7.88 (dd, J=8.3, 4.6 Hz, 2H), 7.59 (d, J=8.0 Hz, 2H), 7.47 (d, J=8.4 Hz, 1H), 7.39 (d, J=8.4 Hz, 1H), 5.94-5.87 (m, 1H), 5.19-5.12 (m, 2H), 4.38-4.33 (m, 2H), 4.17-4.11 (m, 1H), 3.65-3.53 (m, 3H), 3.47-3.37 (m, 4H), 3.10-2.94 (m, 5H), 2.32-2.12 (m, 4H), 2.04 (d, J=10.6 Hz, 3H), 1.95-1.81 (m, 2H). LCMS for $C_{37}H_{41}N_6O_6S$ $(M+H)^+$: m/z=697.3; Found: 697.3.

Examples 21-23

Examples 21-23 of Table 5 were prepared according to procedures described in to Example 20.

TABLE 5

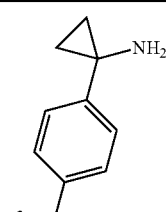

| Ex. No. | Name | R | LCMS [M + H]⁺ | ¹H NMR Spectrum |
|---|---|---|---|---|
| 21 | 4-(9-(4-(1-Aminocyclopropyl)phenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid trifluoroacetic acid salt (1:2) | 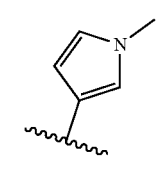 [SMILES: *c1ccn(C)c1] | 705.2 | — |
| 22 | 4-(4-Methyl-9-(1-methyl-1H-pyrrol-3-yl)-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid trifluoroacetic acid salt | 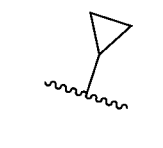 | 653.2 | ¹H NMR (400 MHz, DMSO-$d_6$) δ 12.09 (s, 1H), 9.49 (s, 1H), 8.14 (s, 1H), 7.90 (d, J = 8.5 Hz, 2H), 7.81 (d, J = 7.9 Hz, 2H), 7.46 (d, J = 8.1 Hz, 2H), 7.25 (d, J = 8.6 Hz, 2H), 6.87-6.84 (m, 1H), 6.75-6.72 (m, 1H), 6.04-6.01 (m, 1H), 4.69 (s, 2H), 4.33-4.26 (m, 1H), 3.66 (s, 3H), 3.58-3.50 (m, 2H), 2.99 (m, 4H), 3.41 (s, 3H), 2.25 (d, J = 13.5 Hz, 2H), 1.92-1.79 (m, 2H). |
| 23 | 4-(9-Cyclopropyl-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid, trifluoroacetic acid salt | | 614.2 | ¹H NMR (500 MHz, DMSO-$d_6$) δ 11.87 (s, 1H), 9.63 (s, 1H), 8.13 (s, 1H), 7.98 (d, J = 8.3 Hz, 2H), 7.89 (d, J = 7.9 Hz, 2H), 7.62 (d, J = 7.9 Hz, 2H), 7.55 (d, J = 8.4 Hz, 2H), 5.53 (s, 2H), 4.42-4.38 (m, 2H), 3.12-2.96 (m, 5H), 2.33-2.26 (m, 2H), 2.21-2.12 (m, 2H), 1.96-1.82 (m, 2H), 1.24 (s, 1H), 0.92 (d, J = 7.5 Hz, 2H), 0.22 (d, J = 5.2 Hz, 2H). |

163

Example 24. 4-(9-Cyano-4-methyl-8-(4-((4-(methyl-sulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

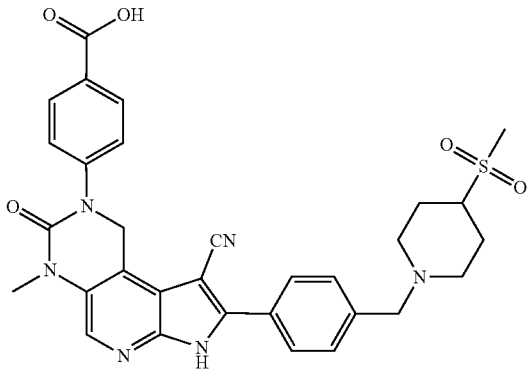 [SMILES: CN1C(=O)N(c2ccc(C(=O)O)cc2)Cc2c1cnc1[nH]c(-c3ccc(CN4CCC(S(C)(=O)=O)CC4)cc3)c(C#N)c21]

A solution of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate (Example 11, Step 11, 8.0 mg, 9.35 µmol), zinc cyanide (1.65 mg, 0.014 mmol), and tetrakis(triphenylphosphine)palladium(0) (1.08 mg, 0.935 µmol) in DMF (0.623 mL) was bubbled with nitrogen for 5 min. The mixture was capped and heated in the microwave at 150° C. for 1 h. Acetonitrile was added, and the reaction mixture was filtered through 0.45 micron filter cartridge. The solids were rinsed with ethyl acetate and the filtrate was concentrated to a yellow oil. The resulting oil was placed on high vacuum for 1 h, then dissolved in a mixture of dichloromethane (0.50 mL) and TFA (0.50 mL), then stirred at room temp for 1 h. The reaction mixture was concentrated and the resulting residue was dissolved in acetonitrile and water. The solution was purified via preparative LCMS (XBridge C18 Column, eluting with a gradient of acetonitrile in water with 0.1% trifluoroacetic acid, at flow rate of 60 mL/min) to afford the desired product (2.8 mg, 42.0%) as a yellow solid. LCMS for $C_{31}H_{31}NA_6O_5S$ (M+H)$^+$: m/z=599.2; Found: 599.1.

Example 25. 4-(9-Iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

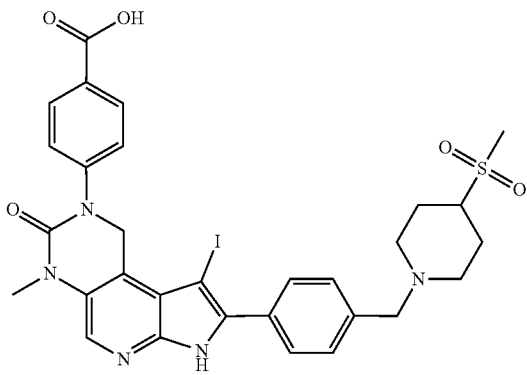 [SMILES: CN1C(=O)N(c2ccc(C(=O)O)cc2)Cc2c1cnc1[nH]c(-c3ccc(CN4CCC(S(C)(=O)=O)CC4)cc3)c(I)c21]

164

Step 1. 4-(4-Methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid Trifluoroacetic Acid Salt

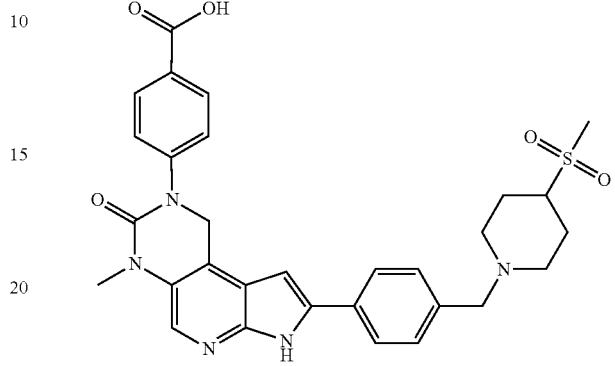

A solution of tert-butyl 4-(4-methyl-8-(4-((4-(methylsulfonyl)piperidin-1-yl)methyl)phenyl)-3-oxo-7-(phenylsulfonyl)-1,3,4,7-tetrahydro-2H-pyrrolo[3',2':5,6]pyrido[3,4-d]pyrimidin-2-yl)benzoate (Example 11, Step 8, 0.17 g, 0.221 mmol) in THF (4.0 mL), methanol (4.00 mL), and 1.78 M KOH in water (4.0 mL, 7.12 mmol) was stirred overnight, affording a precipitate. Dichloromethane and deionized water were added to the reaction mixture. The organic layer was collected to isolate tert-Butyl 4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate (Example 11, Step 9). The aqueous layer was treated with TFA (0.60 mL, 7.79 mmol), which afforded solids. The solids were dissolved by DMF (10 mL) addition, and the resulting solution was purified via preparative LCMS (XBridge C18 Column, eluting with a gradient of acetonitrile in water with 0.1% trifluoroacetic acid, at flow rate of 60 mL/min) to afford the desired product (20 mg, 11.3%). LCMS for $C_{30}H_{32}N_5O_5S$ (M+H)$^+$: m/z=574.2; Found: 573.9.

Step 2. 4-(9-Iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid, Trifluoroacetic Acid Salt To a solution of 4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid trifluoroacetic acid salt (10 mg, 0.0146 mmol) in DMF (1.0 mL) was added NIS (3.20 mg, 0.0142 mmol). The reaction mixture was diluted with methanol and purified via preparative LCMS (XBridge C18 Column, eluting with a gradient of acetonitrile in water with 0.1% trifluoroacetic acid, at flow rate of 60 mL/min) to afford the desired product (3.0 mg, 25.3%). LCMS for $C_{30}H_{31}IN_5O_5S$ (M+H)$^+$: m/z=700.1; Found: 700.1.

Example 26. 4-(8-Cyclopropyl-9-(4-methoxyphenyl)-4-methyl-3-oxo-1,3,4,7-tetrahydro-2H-pyrrolo[3',2':5,6]pyrido[3,4-d]pyrimidin-2-yl)benzoic acid

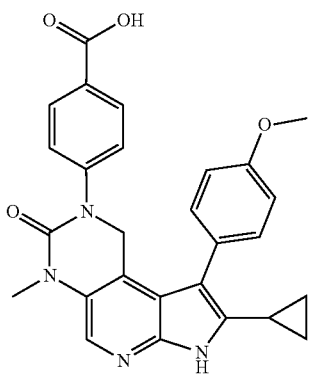 [SMILES: COc1ccc(-c2c(C3CC3)[nH]c3ncc4c(c23)CN(c2ccc(C(=O)O)cc2)C(=O)N4C)cc1]

Step 1. tert-Butyl 4-(8-cyclopropyl-4-methyl-3-oxo-7-(phenylsulfonyl)-1,3,4,7-tetrahydro-2H-pyrrolo[3',2':5,6]pyrido[3,4-d]pyrimidin-2-yl)benzoate

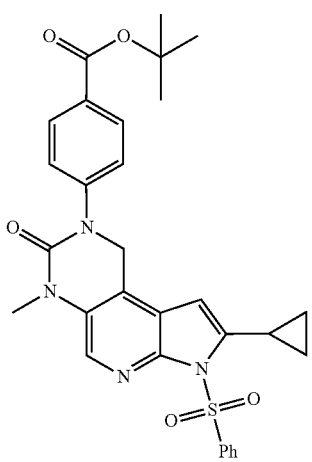 [SMILES: CN1C(=O)N(c2ccc(C(=O)OC(C)(C)C)cc2)Cc2c1cnc1c2cc(C2CC2)n1S(=O)(=O)c1ccccc1]

The title compound was prepared according to the procedures described in Example 11, Step 12, using tert-butyl 4-(8-bromo-4-methyl-3-oxo-7-(phenylsulfonyl)-1,3,4,7-tetrahydro-2H-pyrrolo[3',2':5,6]pyrido[3,4-d]pyrimidin-2-yl)benzoate and potassium cyclopropyltrifluoroborate in place of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate and (4-methoxyphenyl)boronic acid as the starting materials. LCMS for $C_{30}H_{31}N_4O_5S$ (M+H)$^+$: m/z=559.2; Found: 559.2.

Step 2. tert-Butyl 4-(8-cyclopropyl-4-methyl-3-oxo-1,3,4,7-tetrahydro-2H-pyrrolo[3',2':5,6]pyrido[3,4-d]pyrimidin-2-yl)benzoate

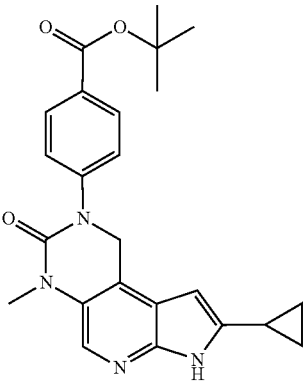 [SMILES: CN1C(=O)N(c2ccc(C(=O)OC(C)(C)C)cc2)Cc2c1cnc1[nH]c(C3CC3)cc21]

The title compound was prepared according to the procedures described in Example 11, Step 9, using tert-butyl 4-(8-cyclopropyl-4-methyl-3-oxo-7-(phenylsulfonyl)-1,3,4,7-tetrahydro-2H-pyrrolo[3',2':5,6]pyrido[3,4-d]pyrimidin-2-yl)benzoate in place of tert-butyl 4-(4-methyl-8-(4-((4-(methylsulfonyl)piperidin-1-yl)methyl)phenyl)-3-oxo-7-(phenylsulfonyl)-1,3,4,7-tetrahydro-2H-pyrrolo[3',2':5,6]pyrido[3,4-d]pyrimidin-2-yl)benzoate as the starting material. LCMS for $C_{24}H_{27}N_4O_3$ (M+H)$^+$: m/z=419.2; Found: 419.2.

Step 3. tert-Butyl 4-(8-cyclopropyl-9-iodo-4-methyl-3-oxo-1,3,4,7-tetrahydro-2H-pyrrolo[3',2':5,6]pyrido[3,4-d]pyrimidin-2-yl)benzoate

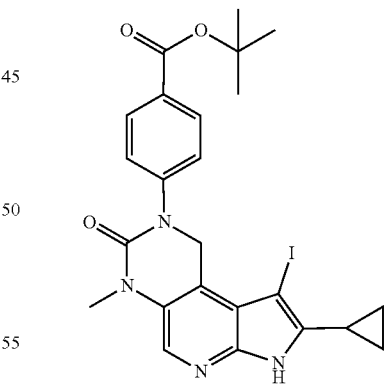

The title compound was prepared according to the procedures described in Example 11, Step 10, using tert-butyl 4-(8-cyclopropyl-4-methyl-3-oxo-1,3,4,7-tetrahydro-2H-pyrrolo[3',2':5,6]pyrido[3,4-d]pyrimidin-2-yl)benzoate in place of tert-butyl 4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate as the starting material. LCMS for $C_{24}H_{26}IN_4O_3$(M+H)$^+$: m/z=545.1; Found: 545.1.

Step 4. tert-Butyl 2-(4-(tert-butoxycarbonyl)phenyl)-8-cyclopropyl-9-iodo-4-methyl-3-oxo-1,2,3,4-tetrahydro-7H-pyrrolo[3',2':5,6]pyrido[3,4-d]pyrimidine-7-carboxylate

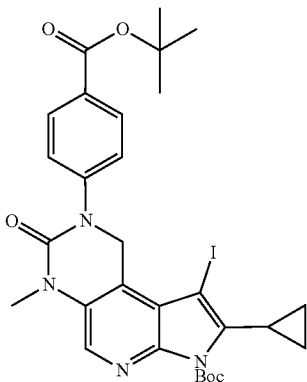 [SMILES: CN1C(=O)N(c2ccc(C(=O)OC(C)(C)C)cc2)Cc2c1cnc1c2c(I)c(C2CC2)n1C(=O)OC(C)(C)C]

The title compound was prepared according to the procedures described in Example 11, Step 11, using tert-butyl 4-(8-cyclopropyl-9-iodo-4-methyl-3-oxo-1,3,4,7-tetrahydro-2H-pyrrolo[3',2':5,6]pyrido[3,4-d]pyrimidin-2-yl)benzoate in place of tert-butyl 4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoate as the starting material. LCMS for $C_{29}H_{34}IN_4O_5(M+H)^+$: m/z=645.2; Found: 645.1.

Step 5. 4-(8-Cyclopropyl-9-(4-methoxyphenyl)-4-methyl-3-oxo-1,3,4,7-tetrahydro-2H-pyrrolo[3',2':5,6]pyrido[3,4-d]pyrimidin-2-yl)benzoic Acid The title compound was prepared according to the procedures described in Example 20, using tert-butyl 2-(4-(tert-butoxycarbonyl)phenyl)-8-cyclopropyl-9-iodo-4-methyl-3-oxo-1,2,3,4-tetrahydro-7H-pyrrolo[3',2':5,6]pyrido[3,4-d]pyrimidine-7-carboxylate and (4-methoxyphenyl)boronic acid in place of tert-butyl 2-(4-(tert-butoxycarbonyl)phenyl)-9-iodo-4-methyl-8-(4-((4-(methylsulfonyl)piperidin-1-yl)methyl)phenyl)-3-oxo-1,2,3,4-tetrahydro-7H-pyrrolo[3',2':5,6]pyrido[3,4-d]pyrimidine-7-carboxylate and 1-(4-(4,4,5,5-tetramethyl-1,3,2-dioxaborolan-2-yl)-3,6-dihydropyridin-1(2H)-yl)ethan-1-one as the starting materials. LCMS for $C_{27}H_{25}N_4O_4$ $(M+H)^+$: m/z=469.2; Found: 469.1.

Example A. JAK2 LanthaScreen JH1 Binding Assay

JAK2 JH1 binding assay utilizes catalytic domain (JH1, amino acids 826-1132) of human JAK2 expressed as N-terminal FLAG-tagged, biotinylated protein in a baculovirus expression system (Carna Biosciences, Product #08-445-20N). The assay was conducted in black 384-well polystyrene plates in a final reaction volume of 20 μL. JAK2 JH1 (1.5 nM) was incubated with compounds (100 nL serially diluted in DMSO) in the presence of 50 nM Fluorescent JAK2-JH1 Tracer and 0.5 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 2 hours at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example B. JAK2 LanthaScreen JH2-WT Binding Assay

JAK2 JH2-WT binding assay utilizes pseudo-kinase domain (JH2, amino-acids 536-812 with 3 surface mutations W659A, W777A, F794H) of human Wild Type JAK2 expressed as C-terminal His-Avi-tagged, biotinylated protein in a baculovirus expression system (BPS Bioscience, Catalog #79463). The assay was conducted in black 384-well polystyrene plates in a final reaction volume of 20 μL. JAK2 JH2-WT (0.145 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example C. JAK2 LanthaScreen JH2-V617F Binding Assay

JAK2 JH2-V617F binding assay utilizes pseudo-kinase domain (JH2, amino-acids 536-812 with 3 surface mutations W659A, W777A, F794H) of human V617F mutant JAK2 expressed as C-terminal His-Avi-tagged, biotinylated protein in a baculovirus expression system (BPS Bioscience, Catalog #79498). The assay was conducted in black 384-well polystyrene plates in a final reaction volume of 20 μL. JAK2 JH2-V617F (0.26 nM) was incubated with compounds (100 nL serially diluted in DMSO) in the presence of 50 nM Fluorescent JAK2-JH2 Tracer (MedChem Express Catalog #HY-102055) and 0.25 nM Streptavidin-Tb cryptate (Cisbio Part #610SATLB) in assay buffer (50 mM Tris, pH=7.5, 10 mM MgCl$_2$, 0.01% Brij-35, 0.1% BSA, 1 mM EGTA, 5% Glycerol and 5 mM DTT). Non-specific binding was accessed in the presence of 2 mM ATP. After incubation for 1 hour at 25° C., LanthaScreen signals were read on a PHERAstar FS plate reader (BMG LABTECH). Data was analyzed with IDBS XLfit and GraphPad Prism 5.0 software using a four parameter dose response curve to determine IC50 for each compound.

Example D. JAK2 HTRF Enzyme Activity Assay

JAK2 enzyme activity assays utilize catalytic domain (JH1, amino acids 808-1132) of human JAK2 expressed as N-terminal His-tagged protein in a baculovirus expression system (BPS Bioscience, Catalog #40450). The assays was conducted in black 384-well polystyrene plates in a final reaction volume of 20 μL. JAK2 (0.015 nM) was incubated with compounds (100 nL serially diluted in DMSO) in the presence of ATP (30 μM or 1 mM) and 500 nM Biotin-labeled EQEDEPEGDYFEWLE (SEQ ID NO.: 1) peptide (BioSource International, custom synthesis) in assay buffer (50 mM Tris, pH=7.5, 10 mM MgCl$_2$, 0.01% Brij-35, 0.1% BSA, 1 mM EGTA, 5% Glycerol and 5 mM DTT) for 60 minutes at 25° C. The reactions were stopped by the addition of 10 μL of detection buffer (50 mM Tris, pH 7.8, 0.5 mg/mL BSA, 150 mM NaCl), supplemented with EDTA, LANCE Eu-W1024 anti-phosphotyrosine (PY20), (PerkinElmer, Catalog #AD0067) and Streptavidin SureLight APC (PerkinElmer Catalog #CR130-100), for a final concentration of 15 mM, 1.5 nM and 75 nM, respectively. HTRF signals were read after 30 minutes incubation at room temperature on a PHERAstar FS plate reader (BMG LABTECH). Data was analyzed with IDBS XLfit and GraphPad Prism 5.0 software using a four parameter dose response curve to determine IC50 for each compound.

The compounds of the disclosure were tested in one or more of the assays described in Examples A-D, and the resulting data are shown in Table A.

TABLE A

| Ex. No. | JH1 BIND IC$_{50}$ (nM) | JH2 BIND WT IC$_{50}$ (nM) | JH2 BIND V617F IC$_{50}$ (nM) | ENZYME IC$_{50}$ (nM) |
|---|---|---|---|---|
| 1 | + | ++ | +++ | + |
| 2 | + | ++ | +++ | + |
| 3 | ++++ | + | + | ++++ |
| 4 | ++ | ++ | ++ | ++ |
| 5 | + | ++ | +++ | + |
| 6 | ++ | ++++ | +++++ | ++ |
| 7 | + | +++ | ++++ | + |
| 8 | ++ | ++ | +++ | ++ |
| 9 | ++ | ++ | ++ | ++ |
| 10 | ++++ | + | ++ | ++++ |
| 11 | +++++ | + | + | +++++ |
| 12 | ++++ | + | + | ++++ |
| 13 | ++++ | + | + | ++++ |
| 14 | + | + | + | + |
| 15 | +++++ | ++ | ++ | +++++ |
| 16 | + | + | + | + |
| 17 | + | + | + | + |
| 18 | + | + | + | + |
| 19 | + | + | + | + |
| 20 | +++++ | + | + | +++++ |
| 21 | ++++ | + | + | +++++ |
| 22 | ++++ | + | + | ++++ |
| 23 | +++++ | + | + | +++++ |
| 24 | +++++ | ++ | ++ | +++++ |
| 25 | +++ | + | + | ++++ |
| 26 | +++++ | ++ | ++ | +++++ |

+ refers to IC$_{50}$ of ≤100 nM
++ refers to IC$_{50}$ of >100 nM to ≤500 nM
+++ refers to IC$_{50}$ of >500 nM to ≤1000 nM
++++ refers to IC$_{50}$ of >1000 nM to ≤2500 nM
+++++ refers to IC$_{50}$ of >2500 nM Example E. Cell Culture and STAT5 (Tyr694) Phosphorylation Cell Based Assay Ba/F3 cells expressing human JAK2 V617F/EPOR (mouse JAK2 WT knocked out by CRISPR) are cultured in RPMI media with 10% FBS, 11 g/mL Puromycin, 1 mg/mL Geneticin (Thermo Fisher). Ba/F3 cells expressing human JAK2 WT/EPOR are cultured in RPMI media with 10% FBS, 1 μg/mL Puromycin, 1 mg/mL Geneticin and 2 ng/mL EPO. 24 hours before the assay, the culture medium for JAK2 V617F/EPOR Ba/F3 cells are changed to RPMI with 10% FBS without antibiotic (assay medium 1). Culture medium for Ba/F3 cells expressing human JAK2 WT/EPOR are changed to RPMI with 10% FBS and 2 ng/mL EPO (R&D systems) without antibiotic (assay medium 2). 50 nL/well test compounds in DMSO are transferred to the 384 white low volume cell culture plate (Greiner Bio-one) by ECHO liquid handler (Labcyte). The cells are centrifuged, resuspended in the corresponding fresh assay medium and dispensed at L/well (6×10$^6$ cells/mL) with 0.5% DMSO in the final assay. After the treated cells are incubated at 37° C., 5% CO$_2$ for 2 hours, 4 μL/well supplemented lysis buffer (100× blocking buffer diluted 25 fold in 4× lysis buffer, Perkin-Elmer) are added and incubated at room temperature for 60 min with gentle shaking on orbital shaker at 600 rpm. Phospho-STAT5 Cryptate antibody and Phospho-STAT5 d2 antibody (1:1 vol/vol, Perkin-Elmer) are premixed and diluted 20 fold within the detection buffer. 4 μL of the premixed antibody solution are added to each well followed with 16 hours incubation at room temperature. The product activity is determined by measuring the fluorescence at 620 nm and 665 nm on Pherastar microplate reader (BMG Labtech). A ratio is calculated (665/620 nm) for each well. Wells with DMSO serve as the positive controls and wells containing high concentration of control compound are used as negative controls. IC$_{50}$ determination is performed by fitting the curve of percent control activity versus the log of the compound concentration using the Genedata Screener software.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

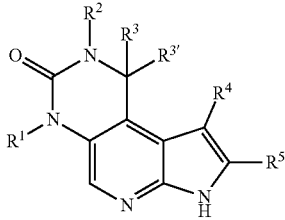

or a pharmaceutically acceptable salt thereof, wherein:
$R^1$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^1$ are each optionally substituted with 1, 2, 3, 4, 5, 6, 7, or 8 independently selected $R^M$ substituents;
$R^2$ is selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^2$ are each optionally substituted with 1, 2, 3, 4, 5, 6, 7, or 8 independently selected $R^{2A}$ substituents;
each $R^{2A}$ is independently selected from halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a21}$, $SR^{a21}$, $NHOR^{a21}$, $C(O)R^{b21}$, $C(O)NR^{c21}R^{d21}$, $C(O)NR^{c21}(OR^{a21})$, $C(O)OR^{a21}$, $OC(O)R^{b21}$, $OC(O)NR^{c21}R^{d21}$, $NR^{c21}R^{d21}$, $NR^{c21}NR^{c21}R^{d21}$, $NR^{c21}C(O)R^{b21}$, $NR^{c21}C(O)OR^{a21}$, $NR^{c21}C(O)NR^{c21}R^{d21}$, $C(=NR^{e21})R^{b21}$, $C(=NR^{e21})NR^{c21}R^{d21}$, $NR^{c21}C(=NR^{e21})NR^{c21}R^{d21}$, $NR^{c21}C(=NR^{e21})R^{b21}$, $NR^{c21}S(O)R^{b21}$, $NR^{c21}S(O)NR^{c21}R^{d21}$, $NR^{c21}S(O)_2R^{b21}$, $NR^{c21}S(O)(=NR^{e21})R^{b21}$, $NR^{c21}S(O)_2NR^{c21}R^{d21}$, $S(O)R^{b21}$, $S(O)NR^{c21}R^{d21}$, $S(O)_2R^{b21}$, $S(O)_2NR^{c21}R^{d21}$, $OS(O)(=NR^{e21})R^{b21}$, and $OS(O)_2R^{b21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, 4, 5, 6, 7, or 8 independently selected $R^{2B}$ substituents;
each $R^{a21}$, $R^{c21}$, and $R^{d21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{c21}$ and $R^{d21}$ are each optionally substituted with 1, 2, 3, 4, 5, 6, 7, or 8 independently selected $R^{2B}$ substituents;
or, any $R^{c21}$ and $R^{d21}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2B}$ substituents;
each $R^{b21}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b21}$ are each optionally substituted with 1, 2, 3, 4, 5, 6, 7, or 8 independently selected $R^{2B}$ substituents;
each $R^{e21}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;
each $R^{2B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a22}$, $SR^{a22}$, $NHOR^{a22}$, $C(O)R^{b22}$, $C(O)NR^{c22}R^{d22}$, $C(O)NR^{c22}(OR^{a22})$, $C(O)OR^{a22}$, $OC(O)R^{b22}$, $OC(O)NR^{c22}R^{d22}$, $NR^{c22}R^{d22}$, $NR^{c22}NR^{c22}R^{d22}$, $NR^{c22}C(O)R^{b22}$, $NR^{c22}C(O)OR^{a22}$, $NR^{c22}C(O)NR^{c22}R^{d22}$, $C(=NR^{e22})R^{b22}$, $C(=NR^{e22})NR^{c22}R^{d22}$, $NR^{c22}C(=NR^{e22})NR^{c22}R^{d22}$, $NR^{c22}C(=NR^{e22})R^{b22}$, $NR^{c22}S(O)R^{b22}$, $NR^{c22}S(O)NR^{c22}R^{d22}$, $NR^{c22}S(O)_2R^{b22}$, $NR^{c22}S(O)(=NR^{e22})R^{b22}$, $NR^{c22}S(O)_2NR^{c22}R^{d22}$, $S(O)R^{b22}$, $S(O)_2R^{b22}$, $S(O)_2NR^{c22}R^{d22}$, $OS(O)(=NR^{e22})R^{b22}$, and $OS(O)_2R^{b22}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2B}$ are each optionally substituted with 1, 2, 3, 4, 5, 6, 7, or 8 independently selected $R^{2C}$ substituents;

each $R^{a22}$, $R^{c22}$, and $R^{d22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a22}$, $R^{c22}$ and $R^{d22}$ are each optionally substituted with 1, 2, 3, 4, 5, 6, 7, or 8 independently selected $R^{2C}$ substituents;

or, any $R^{c22}$ and $R^{d22}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{2C}$ substituents;

each $R^{b22}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b22}$ are each optionally substituted with 1, 2, 3, 4, 5, 6, 7, or 8 independently selected $R^{2C}$ substituents;

each $R^{e22}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{2C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a23}$, $SR^{a23}$, $NHOR^{a23}$, $C(O)R^{b23}$, $C(O)NR^{c23}R^{d23}$, $C(O)NR^{c23}(OR^{a23})$, $C(O)OR^{a23}$, $OC(O)R^{b23}$, $OC(O)NR^{c23}R^{d23}$, $NR^{c23}R^{d23}$, $NR^{c23}NR^{c23}R^{d23}$, $NR^{c23}C(O)R^{b23}$, $NR^{c23}C(O)OR^{a23}$, $NR^{c23}C(O)NR^{c23}R^{d23}$, $C(=NR^{e23})R^{b23}$, $C(=NR^{e23})NR^{c23}R^{d23}$, $NR^{c23}C(=NR^{e23})NR^{c23}R^{d23}$, $NR^{c23}C(=NR^{e23})R^{b23}$, $NR^{c23}S(O)R^{b23}$, $NR^{c23}S(O)NR^{c23}R^{d23}$, $NR^{c23}S(O)_2R^{b23}$, $NR^{c23}S(O)(=NR^{e23})R^{b23}$, $NR^{c23}S(O)_2NR^{c23}R^{d23}$, $S(O)R^{b23}$, $S(O)NR^{c23}R^{d23}$, $S(O)_2R^{b23}$, $S(O)_2NR^{c23}R^{d23}$, $OS(O)(=NR^{e23})R^{b23}$, and $OS(O)_2R^{b23}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{2C}$ are each optionally substituted with 1, 2, 3, or 4 independently selected $R^M$ substituents;

each $R^{a23}$, $R^{c23}$, and $R^{d23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a23}$, $R^{c23}$ and $R^{d23}$ are each optionally substituted with 1, 2, 3, or 4 independently selected $R^M$ substituents;

or, any $R^{c23}$ and $R^{d23}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b23}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b23}$ are each optionally substituted with 1, 2, 3, or 4 independently selected $R^M$ substituents;

each $R^{e23}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^3$ and $R^{3'}$ are each independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a3}$, $SR^{a3}$, $NHOR^{a3}$, $C(O)R^{b3}$, $C(O)NR^{c3}R^{d3}$, $C(O)NR^{c3}(OR^{a3})$, $C(O)OR^{a3}$, $OC(O)R^{b3}$, $OC(O)NR^{c3}R^{d3}$, $NR^{c3}R^{d3}$, $NR^{c3}NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}C(=NR^{e3})R^{b3}$, $NR^{c3}S(O)R^{b3}$, $NR^{c3}S(O)NR^{c3}R^{d3}$, $NR^{c3}S(O)_2R^{b3}$, $NR^{c3}S(O)(=NR^{e3})R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, $OS(O)(=NR^{e3})R^{b3}$, and $OS(O)_2R^{b3}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^3$ are each optionally substituted with 1, 2, 3, 4, 5, 6, 7, or 8 independently selected $R^{3A}$ substituents;

or, $R^3$ and $R^{3'}$ attached to the same C atom, together with the C atom to which they are attached, form a 3-10 membered cycloalkyl or a 4-10 membered heterocycloalkyl group, wherein the 3-10 membered cycloalkyl or 4-10 membered heterocycloalkyl group is optionally substituted with 1, 2, 3, 4, 5, 6, 7, or 8 independently selected $R^{3A}$ substituents;

each $R^{a3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a3}$, $R^{c3}$ and $R^{d3}$ are each optionally substituted with 1, 2, 3, 4, 5, 6, 7, or 8 independently selected $R^{3A}$ substituents;

or, any $R^{c3}$ and $R^{d3}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3A}$ substituents;

each $R^{b3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b3}$ are each optionally substituted with 1, 2, 3, 4, 5, 6, 7, or 8 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a31}$, $SR^{a31}$, $NHOR^{a31}$, $C(O)R^{b31}$, $C(O)NR^{c31}R^{d31}$, $C(O)NR^{c31}(OR^{a31})$, $C(O)OR^{a31}$, $OC(O)R^{b31}$, $OC(O)NR^{c31}R^{d31}$, $NR^{c31}R^{d31}$, $NR^{c31}NR^{c31}R^{d31}$, $NR^{c31}C(O)R^{b31}$, $NR^{c31}C(O)OR^{a31}$, $NR^{c31}C(O)NR^{c31}R^{d31}$, $C(=NR^{e31})R^{b31}$, $C(=NR^{e31})NR^{c31}R^{d31}$, $NR^{c31}C(=NR^{e31})NR^{c31}R^{d31}$, $NR^{c31}C(=NR^{e31})R^{b31}$, $NR^{c31}S(O)R^{b31}$, $NR^{c31}S(O)NR^{c31}R^{d31}$, $NR^{c31}S(O)_2R^{b31}$, $NR^{c31}S(O)(=NR^{e31})R^{b31}$, $NR^{c31}S(O)_2NR^{c31}R^{d31}$, $S(O)R^{b31}$, $S(O)NR^{c31}R^{d31}$, $S(O)_2R^{b31}$, $S(O)_2NR^{c31}R^{d31}$, $OS(O)(=NR^{e31})R^{b31}$, and $OS(O)_2R^{b31}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3A}$ are each optionally substituted with 1, 2, 3, 4, 5, 6, 7, or 8 independently selected $R^{3B}$ substituents;

each $R^{a31}$, $R^{c31}$, and $R^{d31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a31}$, $R^{c31}$ and $R^{d31}$ are each optionally substituted with 1, 2, 3, 4, 5, 6, 7, or 8 independently selected $R^{3B}$ substituents;

or, any $R^{c31}$ and $R^{d31}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3B}$ substituents;

each $R^{b31}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b31}$ are each optionally substituted with 1, 2, 3, 4, 5, 6, 7, or 8 independently selected $R^{3B}$ substituents;

each $R^{e31}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a32}$, $SR^{a32}$, $NHOR^{a32}$, $C(O)R^{b32}$, $C(O)NR^{c32}R^{d32}$, $C(O)NR^{c32}(OR^{a32})$, $C(O)OR^{a32}$, $OC(O)R^{b32}$, $OC(O)NR^{c32}R^{d32}$, $NR^{c32}R^{d32}$, $NR^{c32}NR^{c32}R^{d32}$, $NR^{c32}C(O)R^{b32}$, $NR^{c32}C(O)OR^{a32}$, $NR^{c32}C(O)NR^{c32}R^{d32}$, $C(=NR^{e32})R^{b32}$, $C(=NR^{e32})NR^{c32}R^{d32}$, $NR^{c32}C(=NR^{e32})NR^{c32}R^{d32}$, $NR^{c32}C(=NR^{e32})R^{b32}$, $NR^{c32}S(O)R^{b32}$, $NR^{c32}S(O)NR^{c32}R^{d32}$, $NR^{c32}S(O)_2R^{b32}$, $NR^{c32}S(O)(=NR^{e32})R^{b32}$, $NR^{c32}S(O)_2NR^{c32}R^{d32}$, $S(O)R^{b32}$, $S(O)NR^{c32}R^{d32}$, $S(O)_2R^{b32}$, $S(O)_2NR^{c32}R^{d32}$, $OS(O)(=NR^{e32})R^{b32}$, and $OS(O)_2R^{b32}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{3B}$ are each optionally substituted with 1, 2, 3, 4, 5, 6, 7, or 8 independently selected $R^{3C}$ substituents;

each $R^{a32}$, $R^{c32}$, and $R^{d32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a32}$, $R^{c32}$ and $R^{d32}$ are each optionally substituted with 1, 2, 3, 4, 5, 6, 7, or 8 independently selected $R^{3C}$ substituents;

or, any $R^{c32}$ and $R^{d32}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{3C}$ substituents;

each $R^{b32}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b32}$ are each optionally substituted with 1, 2, 3, 4, 5, 6, 7, or 8 independently selected $R^{3C}$ substituents;

each $R^{e32}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{3C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a33}$, $SR^{a33}$, $NHOR^{a33}$, $C(O)R^{b33}$, $C(O)NR^{c33}R^{d33}$, $C(O)NR^{c33}(OR^{a33})$, $C(O)OR^{a33}$, $OC(O)R^{b33}$, $OC(O)NR^{c33}R^{d33}$, $NR^{c33}R^{d33}$, $NR^{c33}NR^{c33}R^{d33}$, $NR^{c33}C(O)R^{b33}$, $NR^{c33}C(O)OR^{a33}$, $NR^{c33}C(O)NR^{c33}R^{d33}$, $C(=NR^{e33})R^{b33}$, $C(=NR^{e33})NR^{c33}R^{d33}$, $NR^{c33}C(=NR^{e33})NR^{c33}R^{d33}$, $NR^{c33}C(=NR^{e33})R^{b33}$, $NR^{c33}S(O)R^{b33}$, $NR^{c33}S(O)NR^{c33}R^{d33}$, $NR^{c33}S(O)_2R^{b33}$, $NR^{c33}S(O)(=NR^{e33})R^{b33}$, $NR^{c33}S(O)_2NR^{c33}R^{d33}$, $S(O)R^{b33}$, $S(O)NR^{c33}R^{d33}$, $S(O)_2R^{b33}$, $S(O)_2NR^{c33}R^{d33}$, $OS(O)(=NR^{e33})R^{b33}$, and $OS(O)_2R^{b33}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{3C}$ are each optionally substituted with 1, 2, 3, or 4 independently selected $R^M$ substituents;

each $R^{a33}$, $R^{c33}$, and $R^{d33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a33}$, $R^{c33}$ and $R^{d33}$ are each optionally substituted with 1, 2, 3, or 4 independently selected $R^M$ substituents;

or, any $R^{c33}$ and $R^{d33}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b33}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b33}$ are each optionally substituted with 1, 2, 3, or 4 independently selected $R^M$ substituents;

each $R^{e33}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^4$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, $SR^{a4}$, $NHOR^{a4}$, $C(O)R^{b4}$, $C(O)NR^{c4}R^{d4}$, $C(O)NR^{c4}(OR^{a4})$, $C(O)OR^{a4}$, $OC(O)R^{b4}$, $OC(O)NR^{c4}R^{d4}$, $NR^{c4}R^{d4}$, $NR^{c4}NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}C(=NR^{e4})R^{b4}$, $NR^{c4}S(O)R^{b4}$, $NR^{c4}S(O)NR^{c4}R^{d4}$, $NR^{c4}S(O)_2R^{b4}$, $NR^{c4}S(O)(=NR^{e4})R^{b4}$, $NR^{c4}S(O)_2NR^{c4}R^{d4}$, $S(O)R^{b4}$, $S(O)NR^{c4}R^{d4}$, $S(O)_2NR^{c4}R^{d4}$, $OS(O)(=NR^{e4})R^{b4}$, and $OS(O)_2R^{b4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, 4, 5, 6, 7, or 8 independently selected $R^{44}$ substituents;

each $R^{a4}$, $R^{c4}$, and $R^{d4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a4}$, $R^{c4}$ and $R^{d4}$ are each optionally substituted with 1, 2, 3, 4, 5, 6, 7, or 8 independently selected $R^{4A}$ substituents;

or, any $R^{c4}$ and $R^{d4}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4A}$ substituents;

each $R^{b4}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b4}$ are each optionally substituted with 1, 2, 3, 4, 5, 6, 7, or 8 independently selected $R^{4A}$ substituents;

each $R^{e4}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a41}$, $SR^{a41}$, $NHOR^{a41}$, $C(O)R^{b41}$, $C(O)NR^{c41}R^{d41}$, $C(O)NR^{c41}(OR^{a41})$, $C(O)OR^{a41}$, $OC(O)R^{b41}$, $OC(O)NR^{c41}R^{d41}$, $NR^{c41}R^{d41}$, $NR^{c41}NR^{c41}R^{d41}$, $NR^{c41}C(O)R^{b41}$, $NR^{c41}C(O)OR^{a41}$, $NR^{c41}C(O)NR^{c41}R^{d41}$, $C(=NR^{e41})R^{b41}$, $C(=NR^{e41})NR^{c41}R^{d41}$, $NR^{c41}C(=NR^{e41})NR^{c41}R^{d41}$, $NR^{c41}C(=NR^{e41})R^{b41}$, $NR^{c41}S(O)R^{b41}$, $NR^{c41}S(O)NR^{c41}R^{d41}$, $NR^{c41}S(O)_2R^{b41}$, $NR^{c41}S(O)(=NR^{e41})R^{b41}$, $NR^{c41}S(O)_2NR^{c41}R^{d41}$, $S(O)R^{b41}$, $S(O)NR^{c41}R^{d41}$, $S(O)_2R^{b41}$, $S(O)_2NR^{c41}R^{d41}$, $OS(O)(=NR^{e41})R^{b41}$, and $OS(O)_2R^{b41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4A}$ are each optionally substituted with 1, 2, 3, 4, 5, 6, 7, or 8 independently selected $R^{4B}$ substituents;

each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, 4, 5, 6, 7, or 8 independently selected $R^{4B}$ substituents;

or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents;

each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b41}$ are each optionally substituted with 1, 2, 3, 4, 5, 6, 7, or 8 independently selected $R^{4B}$ substituents;

each $R^{e41}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a42}$, $SR^{a42}$, $NHOR^{a42}$, $C(O)R^{b42}$, $C(O)NR^{c42}R^{d42}$, $C(O)NR^{c42}(OR^{a42})$, $C(O)OR^{a42}$, $OC(O)R^{b42}$, $OC(O)NR^{c42}R^{d42}$, $NR^{c42}R^{d42}$, $NR^{c42}NR^{c42}R^{d42}$ $NR^{c42}C(O)R^{b42}$, $NR^{c42}C(O)OR^{a42}$, $NR^{c42}C(O)NR^{c42}R^{d42}$, $C(=NR^{e42})R^{b42}$, $C(=NR^{e42})NR^{c42}R^{d42}$, $NR^{c42}C(=NR^{e42})NR^{c42}R^{d42}$, $NR^{c42}C(=NR^{e42})R^{b42}$, $NR^{c42}S(O)R^{b42}$, $NR^{c42}S(O)NR^{c42}R^{d42}$, $NR^{c42}S(O)_2R^{b42}$, $NR^{c42}S(O)(=NR^{e42})R^{b42}$, $NR^{c42}S(O)_2NR^{c42}R^{d42}$, $S(O)R^{b42}$, $S(O)NR^{c42}R^{d42}$, $S(O)_2R^{b42}$, $S(O)_2NR^{c42}R^{d42}$, $OS(O)(=NR^{e42})R^{b42}$, and $OS(O)_2R^{b42}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{4B}$ are each optionally substituted with 1, 2, 3, 4, 5, 6, 7, or 8 independently selected $R^{4C}$ substituents;

each $R^{a42}$, $R^{c42}$, and $R^{d42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a42}$, $R^{c42}$ and $R^{d42}$ are each optionally substituted with 1, 2, 3, 4, 5, 6, 7, or 8 independently selected $R^{4C}$ substituents;

or, any $R^{c42}$ and $R^{d42}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4C}$ substituents;

each $R^{b42}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b42}$ are each optionally substituted with 1, 2, 3, 4, 5, 6, 7, or 8 independently selected $R^{4C}$ substituents;

each $R^{e42}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{4C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a43}$, $SR^{a43}$, $NHOR^{a43}$, $C(O)R^{b43}$, $C(O)NR^{c43}R^{d43}$, $C(O)NR^{c43}(OR^{a43})$, $C(O)OR^{a43}$, $OC(O)R^{b43}$, $OC(O)NR^{c43}R^{d43}$, $NR^{c43}R^{d43}$, $NR^{c43}NR^{c43}R^{d43}$, $NR^{c43}C(O)R^{b43}$, $NR^{c43}C(O)OR^{a43}$, $NR^{c43}C(O)NR^{c43}R^{d43}$, $C(=NR^{e43})R^{b43}$, $C(=NR^{e43})NR^{c43}R^{d43}$, $NR^{c43}C(=NR^{e43})NR^{c43}R^{d43}$, $NR^{c43}C(=NR^{e43})R^{b43}$, $NR^{c43}S(O)R^{b43}$, $NR^{c43}S(O)NR^{c43}R^{d43}$, $NR^{c43}S(O)_2R^{b43}$, $NR^{c43}S(O)(=NR^{e43})R^{b43}$, $NR^{c43}S(O)_2NR^{c43}R^{d43}$, $S(O)R^{b43}$, $S(O)NR^{c43}R^{d43}$, $S(O)_2R^{b43}$, $S(O)_2NR^{c43}R^{d43}$, $OS(O)(=NR^{e43})R^{b43}$, and $OS(O)_2R^{b43}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{4C}$ are each optionally substituted with 1, 2, 3, or 4 independently selected $R^M$ substituents;

each $R^{a43}$, $R^{c43}$, and $R^{d43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a43}$, $R^{c43}$ and $R^{d43}$ are each optionally substituted with 1, 2, 3, or 4 independently selected $R^M$ substituents;

or, any $R^{c43}$ and $R^{d43}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b43}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b43}$ are each optionally substituted with 1, 2, 3, or 4 independently selected $R^M$ substituents;

each $R^{e43}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

$R^5$ is selected from H, D, halo, $C_{2-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a5}$, $SR^{a5}$, $NHOR^{a5}$, $C(O)R^{b5}$, $C(O)NR^{c5}R^{d5}$, $C(O)NR^{c5}(OR^{a5})$, $C(O)OR^{a5}$, $OC(O)R^{b5}$, $OC(O)NR^{c5}R^{d5}$, $NR^{c5}R^{d5}$, $NR^{c5}NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}C(=NR^{e5})R^{b5}$, $NR^{c5}S(O)R^{b5}$, $NR^{c5}S(O)NR^{c5}R^{d5}$, $NR^{c5}S(O)_2R^{b5}$, $NR^{c5}S(O)(=NR^{e5})R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$, $OS(O)(=NR^{e5})R^{b5}$, and $OS(O)_2R^{b5}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, 4, 5, 6, 7, or 8 independently selected $R^{5A}$ substituents;

each $R^{a5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a5}$, $R^{c5}$ and $R^{d5}$ are each optionally substituted with 1, 2, 3, 4, 5, 6, 7, or 8 independently selected $R^{5A}$ substituents;

or, any $R^{c5}$ and $R^{d5}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5A}$ substituents;

each $R^{b5}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b5}$ are each optionally substituted with 1, 2, 3, 4, 5, 6, 7, or 8 independently selected $R^{5A}$ substituents;

each $R^{e5}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5A}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a51}$, $SR^{a51}$, $NHOR^{a51}$, $C(O)R^{b51}$, $C(O)NR^{c51}R^{d51}$, $C(O)NR^{c51}(OR^{a51})$, $C(O)OR^{a51}$, $OC(O)R^{b51}$, $OC(O)NR^{c51}R^{d51}$, $NR^{c51}R^{d51}$, $NR^{c51}NR^{c51}R^{d51}$, $NR^{c51}C(O)R^{b51}$, $NR^{c51}C(O)OR^{a51}$, $NR^{c51}C(O)NR^{c51}R^{d51}$, $C(=NR^{e51})R^{b51}$, $C(=NR^{e51})NR^{c51}R^{d51}$, $NR^{c51}C(=NR^{e51})NR^{c51}R^{d51}$, $NR^{c51}C(=NR^{e51})R^{b51}$, $NR^{c51}S(O)R^{b51}$, $NR^{c51}S(O)NR^{c51}R^{d51}$, $NR^{c51}S(O)_2R^{b51}$, $NR^{c51}S(O)(=NR^{e51})R^{b51}$, $NR^{c51}S(O)_2NR^{c51}R^{d51}$, $S(O)R^{b51}$, $S(O)NR^{c51}R^{d51}$, $S(O)_2R^{b51}$, $S(O)_2NR^{c51}R^{d51}$, $OS(O)(=NR^{e51})R^{b51}$, and $OS(O)_2R^{b51}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, 4, 5, 6, 7, or 8 independently selected $R^{5B}$ substituents;

each $R^{a51}$, $R^{c51}$, and $R^{d51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a51}$, $R^{c51}$ and $R^{d51}$ are each optionally substituted with 1, 2, 3, 4, 5, 6, 7, or 8 independently selected $R^{5B}$ substituents;

or, any $R^{c51}$ and $R^{d51}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5B}$ substituents;

each $R^{b51}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b51}$ are each optionally substituted with 1, 2, 3, 4, 5, 6, 7, or 8 independently selected $R^{5B}$ substituents;

each $R^{e51}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5B}$ is independently selected from D, halo, oxo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a52}$, $SR^{a52}$, $NHOR^{a52}$, $C(O)R^{b52}$, $C(O)NR^{c52}R^{d52}$, $C(O)NR^{c52}(OR^{a52})$, $C(O)OR^{a52}$, $OC(O)R^{b52}$, $OC(O)NR^{c52}R^{d52}$, $NR^{c52}R^{d52}$, $NR^{c52}NR^{c52}R^{d52}$, $NR^{c52}C(O)R^{b52}$, $NR^{c52}C(O)OR^{a52}$, $NR^{c52}C(O)NR^{c52}R^{d52}$, $C(=NR^{e52})R^{b52}$, $C(=NR^{e52})NR^{c52}R^{d52}$, $NR^{c52}C(=NR^{e52})NR^{c52}R^{d52}$, $NR^{c52}C(=NR^{e52})R^{b52}$, $NR^{c52}S(O)R^{b52}$, $NR^{c52}S(O)NR^{c52}R^{d52}$, $NR^{c52}S(O)(=NR^{e52})R^{b52}$, $NR^{c52}S(O)_2NR^{c52}R^{d52}$, $S(O)R^{b52}$, $S(O)NR^{c52}R^{d52}$, $S(O)_2R^{b52}$, $S(O)_2NR^{c52}R^{d52}$, $OS(O)(=NR^{e52})R^{b52}$, and $OS(O)_2R^{b52}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5B}$ are each optionally substituted with 1, 2, 3, 4, 5, 6, 7, or 8 independently selected $R^{5C}$ substituents;

each $R^{a52}$, $R^{c52}$, and $R^{d52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a52}$, $R^{c52}$ and $R^{d52}$ are each optionally substituted with 1, 2, 3, 4, 5, 6, 7, or 8 independently selected $R^{5C}$ substituents;

or, any $R^{c52}$ and $R^{d52}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{5C}$ substituents;

each $R^{b52}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{b52}$ are each optionally substituted with 1, 2, 3, 4, 5, 6, 7, or 8 independently selected $R^{5C}$ substituents;

each $R^{e52}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{5C}$ is independently selected from D, halo, oxo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a53}$, $SR^{a53}$, $NHOR^{a53}$, $C(O)R^{b53}$, $C(O)NR^{c53}R^{d53}$, $C(O)NR^{c53}(OR^{a53})$, $C(O)OR^{a53}$, $OC(O)R^{b53}$, $OC(O)NR^{c53}R^{d53}$, $NR^{c53}R^{d53}$, $NR^{c53}R^{d53}$, $NR^{c53}C(O)R^{b53}$, $NR^{c53}C(O)OR^{a53}$, $NR^{c53}C(O)NR^{c53}R^{d53}$, $C(=NR^{e53})R^{b53}$, $C(=NR^{e53})NR^{c53}R^{d53}$, $NR^{c53}C(=NR^{e53})NR^{c53}R^{d53}$, $NR^{c53}C(=NR^{e53})R^{b53}$, $NR^{c53}S(O)R^{b53}$, $NR^{c53}S(O)NR^{c53}R^{d53}$, $NR^{c53}S(O)_2R^{b53}$, $NR^{c53}S(O)(=NR^{e53})R^{b53}$, $NR^{c53}S(O)_2NR^{c53}R^{d53}$, $S(O)R^{b53}$, $S(O)NR^{c53}R^{d53}$, $S(O)_2R^{b53}$, $S(O)_2NR^{c53}R^{d53}$, $OS(O)(=NR^{e53})R^{b53}$, and $OS(O)_2R^{b53}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- of $R^{5C}$ are each optionally substituted with 1, 2, 3, or 4 independently selected $R^M$ substituents;

each $R^{a53}$, $R^{c53}$, and $R^{d53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a53}$, $R^{c53}$ and $R^{d53}$ are each optionally substituted with 1, 2, 3, or 4 independently selected $R^M$ substituents;

or, any $R^{c53}$ and $R^{d53}$ attached to the same N atom, together with the N atom to which they are attached, form a 5-6 membered heteroaryl or a 4-7 membered heterocycloalkyl group, wherein the 5-6 membered heteroaryl or 4-7 membered heterocycloalkyl group is optionally substituted with 1, 2, 3, or 4 independently selected $R^M$ substituents;

each $R^{b53}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{b53}$ are each optionally substituted with 1, 2, 3, or 4 independently selected $R^M$ substituents;

each $R^{e53}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-; and each $R^M$ is independently selected from H, D, OH, halo, oxo, CN, C(O)OH, $NH_2$, $NO_2$, $SF_5$, $C_{1-6}$ alkyl, $C_{1-6}$alkoxy, $C_{1-6}$haloalkoxy, $C_{1-6}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

2. The compound of claim 1, or a pharmaceutically acceptable salt thereof, wherein $R^1$ is selected from H, $C_{1-6}$ alkyl, $C_{1-6}$ haloalkyl, $C_{2-6}$ alkenyl, and $C_{2-6}$ alkynyl.

3. The compound of claim 1, or a pharmaceutically acceptable salt thereof, wherein $R^1$ is selected from H and $C_{1-6}$ alkyl.

4. The compound of claim 1, or a pharmaceutically acceptable salt thereof, wherein $R^1$ is selected from H and methyl.

5. The compound of claim 1, or a pharmaceutically acceptable salt thereof, wherein $R^2$ is selected from H, $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl-, wherein the $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl- of $R^2$ are each optionally substituted with 1, 2, 3, or 4 independently selected $R^{2A}$ substituents.

6. The compound of claim 1, or a pharmaceutically acceptable salt thereof, wherein $R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl- of $R^2$ are each optionally substituted with 1, 2, 3, or 4 independently selected $R^{2A}$ substituents.

7. The compound of claim 1, or a pharmaceutically acceptable salt thereof, wherein $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1, 2, 3, or 4 independently selected $R^{2A}$ substituents.

8. The compound of claim 1, or a pharmaceutically acceptable salt thereof, wherein each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b21}$, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents.

9. The compound of claim 1, or a pharmaceutically acceptable salt thereof, wherein each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents.

10. The compound of claim 1, or a pharmaceutically acceptable salt thereof, wherein $R^{a21}$, $R^{b21}$, $R^{c21}$, and $R^{d21}$ are each independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents.

11. The compound of claim 1, or a pharmaceutically acceptable salt thereof, wherein $R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents.

12. The compound of claim 1, or a pharmaceutically acceptable salt thereof, wherein $R^{a21}$, $R^{b21}$, $R^{c21}$, and $R^{d21}$ are each independently selected from H, methyl, ethyl, phenyl, pyridinyl, cyclopropyl, cyclohexyl, dihydroisobenzofuranyl, tetrahydrofuranyl, tetrahydropyranyl, phenylmethyl, cyclohexylmethyl, tetrahydropyranylmethyl, cyclopropylmethyl, and pyridinylmethyl of $R^{a21}$, $R^{b21}$, $R^{c21}$, and $R^{d21}$ are each optionally substituted with 1, 2, 3, or 4 independently selected $R^{2B}$ substituents.

13. The compound of claim 1, or a pharmaceutically acceptable salt thereof, wherein each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN; and each $R^{a22}$, $R^{c22}$, and $R^{d22}$ is independently selected from H and $C_{1-6}$ alkyl.

14. The compound of claim 1, or a pharmaceutically acceptable salt thereof, wherein each $R^{2B}$ is independently selected from methyl, hydroxy, methoxy, dimethylamino, CN, and C(O)OH.

15. The compound of claim 1, or a pharmaceutically acceptable salt thereof, wherein $R^2$ is selected from H, methyl, ethyl, isopropyl, tert-butyl, phenyl, cyclohexyl, piperidinyl, phenyl, pyridinylmethyl, phenylmethyl, and phenylethyl, wherein the methyl, ethyl, isopropyl, tert-butyl, phenyl, cyclohexyl, piperidinyl, phenyl, pyridinylmethyl, phenylmethyl, and phenylethyl of $R^2$ are each optionally substituted with 1, 2, 3, or 4 independently selected $R^{2A}$ substituents; and each $R^{2A}$ is independently selected from fluoro, chloro, bromo, methyl, ethyl, piperazinyl, morpholinyl, piperidinyl, morpholinylmethyl, dimethylamino, C(O)OH, $C(O)NHCH_3$, $C(O)NHOCH_3$, $C(O)NHCH_2CH_2OH$, $C(O)NHCH_2CH_2OCH_3$, $C(O)N(CH_3)CH_2CH_2OH$, $C(O)N(CH_3)CH_2CH_2OCH_3$, $C(O)NHCH_2C(O)NHNHCH_2$-phenyl, C(O)NH-cyclopropyl, C(O)NH-cyclohexyl, C(O)NH-phenyl, C(O)NH-pyridinyl, $C(O)N(CH_3)$-pyridinyl, C(O)NH-dihydroisobenzofuranyl, C(O)NH-tetrahydrofuranyl, C(O)NH-tetrahydropyranyl, $C(O)N(CH_3)$-tetrahydropyranyl, C(O)NH-(cyclopropylmethyl), C(O)NH-(cyclohexylmethyl), C(O)NH-(phenylmethyl), C(O)NH-(tetrahydropyranylmethyl), C(O)NH-(pyridinylmethyl), NHC(O)-tetrahydropyranyl, $NHC(O)CH_2CN$, $NHC(O)CH_2CH_3$, $NHCH_2C(O)OH$, $NHCH_2CH_2OCH_3$, and $S(O)_2NH_2$, wherein the methyl, ethyl, piperazinyl, morpholinyl, piperidinyl, morpholinylmethyl, C(O)NH-cyclopropyl, C(O)NH-cyclohexyl, C(O)NH-phenyl, C(O)NH-pyridinyl, $C(O)N(CH_3)$-pyridinyl, C(O)NH-dihydroisobenzofuranyl, C(O)NH-tetrahydrofuranyl, C(O)NH-tetrahydropyranyl, $C(O)N(CH_3)$-tetrahydropyranyl, C(O)NH-(cyclopropylmethyl), C(O)NH-(cyclohexylmethyl), C(O)NH-(phenylmethyl), C(O)NH-(tetrahydropyranylmethyl), C(O)NH-(pyridinylmethyl), and NHC(O)-tetrahydropyranyl, are each optionally substituted with 1, 2, or 3 substituents independently selected from fluoro, methyl, hydroxy, hydroxymethyl, cyano, cyanomethyl, methoxy, and C(O)OH.

16. The compound of claim 1, or a pharmaceutically acceptable salt thereof, wherein $R^3$ is selected from H, $C_{1-6}$ alkyl, $C_{1-6}$ haloalkyl, $C_{2-6}$ alkenyl, and $C_{2-6}$ alkynyl.

17. The compound of claim 1, or a pharmaceutically acceptable salt thereof, wherein $R^3$ is selected from H and $C_{1-6}$ alkyl.

18. The compound of claim 1, or a pharmaceutically acceptable salt thereof, wherein $R^3$ is selected from H and methyl.

19. The compound of claim 1, or a pharmaceutically acceptable salt thereof, wherein $R^{3'}$ is selected from H, $C_{1-6}$ alkyl, $C_{1-6}$ haloalkyl, $C_{2-6}$ alkenyl, and $C_{2-6}$ alkynyl.

20. The compound of claim 1, or a pharmaceutically acceptable salt thereof, wherein $R^{3'}$ is selected from H and $C_{1-6}$ alkyl.

21. The compound of claim 1, or a pharmaceutically acceptable salt thereof, wherein $R^{3'}$ is H.

22. The compound of claim 1, or a pharmaceutically acceptable salt thereof, wherein $R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents.

23. The compound of claim 1, or a pharmaceutically acceptable salt thereof, wherein $R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;
each $R^{a4}$ and $R^{b4}$ is independently selected from H and $C_{1-6}$ alkyl.

24. The compound of claim 1, or a pharmaceutically acceptable salt thereof, wherein $R^4$ is selected from H, methyl, ethenyl, isopropenyl, cyano, iodo, cyclopropyl, cyclohexenyl, phenyl, dihydropyridinyl, pyrazolyl, pyrrolyl, and methoxycarbonyl, wherein the methyl, ethenyl, isopropenyl, cyclopropyl, cyclohexenyl, phenyl, dihydropyridinyl, pyrazolyl, and pyrrolyl of $R^4$ are each optionally substituted with 1, 2, 3, or 4 independently selected $R^{4A}$ substituents.

25. The compound of claim 1, or a pharmaceutically acceptable salt thereof, wherein each $R^{4A}$ is independently selected from halo, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, $C_{3-10}$ cycloalkyl, 5-10 membered heteroaryl, 4-10 membered heterocycloalkyl, CN, $NO_2$, $OR^{a41}$, $C(O)R^{b41}$, $C(O)NR^{c41}R^{d41}$, $NR^{c41}R^{d41}$, $NR^{c41}C(O)R^{b41}$, $NR^{c41}S(O)R^{b41}$, $NR^{c41}S(O)_2R^{b41}$, $S(O)R^{b41}$, $S(O)NR^{c41}R^{d41}$, $S(O)_2R^{b41}$, and $S(O)_2NR^{c41}R^{d41}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, of $R^{4A}$ are each optionally substituted with 1, 2, 3, or 4 independently selected $R^{4B}$ substituents.

26. The compound of claim 1, or a pharmaceutically acceptable salt thereof, wherein each $R^{4A}$ is independently selected from halo, $C_{1-6}$ alkyl, phenyl, $C_{3-6}$ cycloalkyl, 5-6 membered heteroaryl, 4-6 membered heterocycloalkyl, CN, $OR^{a41}$, $C(O)R^{b41}$, $C(O)NR^{c41}R^{d41}$, $NR^{c41}C(O)R^{b41}$, $S(O)_2R^{b41}$, and $S(O)_2NR^{c41}R^{d41}$, wherein the $C_{1-6}$ alkyl, phenyl, $C_{3-6}$ cycloalkyl, 5-6 membered heteroaryl, and 4-6 membered heterocycloalkyl, of $R^{4A}$ are each optionally substituted with 1, 2, 3, or 4 independently selected $R^{4B}$ substituents.

27. The compound of claim 1, or a pharmaceutically acceptable salt thereof, wherein:
each $R^{a41}$, $R^{c41}$, and $R^{d41}$ is independently selected from H, $C_{1-6}$ alkyl, $C_{1-6}$ haloalkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a41}$, $R^{c41}$ and $R^{d41}$ are each optionally substituted with 1, 2, 3, or 4 independently selected $R^{4B}$ substituents;
or, any $R^{c41}$ and $R^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected $R^{4B}$ substituents; and
each $R^{b41}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl of $R^{b41}$ are each optionally substituted with 1, 2, 3, or 4 independently selected $R^{4B}$ substituents.

28. The compound of claim 1, wherein each $R^{4B}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a42}$, $SR^{a42}$, $C(O)R^{b42}$, $C(O)NR^{c42}R^{d42}$, $C(O)OR^{a42}$, $OC(O)R^{b42}$, $OC(O)NR^{c42}R^{d42}$, $NR^{c42}R^{d42}$ $NR^{c42}C(O)R^{b42}$, and $NR^{c42}C(O)OR^{a42}$, wherein the $C_{1-6}$ alkyl, $C_{2-6}$ alkenyl, and $C_{2-6}$ alkynyl of $R^{4B}$ are each optionally substituted with 1, 2, 3, or 4 independently selected $R^{4C}$ substituents.

29. The compound of claim 1, wherein:
each $R^{a42}$, $R^{c42}$, and $R^{d42}$ is independently selected from H, $C_{1-6}$ alkyl, $C_{1-6}$ haloalkyl, $C_{2-6}$ alkenyl, and $C_{2-6}$ alkynyl; and
each $R^{b42}$ is independently selected from H, $C_{1-6}$ alkyl, $C_{1-6}$ haloalkyl, $C_{2-6}$ alkenyl, and $C_{2-6}$ alkynyl.

30. The compound of claim 1, wherein each $R^{4C}$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a43}$, $C(O)R^{b43}$, $C(O)NR^{c43}R^{d43}$, and $C(O)OR^{a43}$; and
each $R^{a43}$, $R^{b43}$, $R^{c43}$, and $R^{d43}$ is independently selected from H and $C_{1-6}$ alkyl.

31. The compound of claim 1, or a pharmaceutically acceptable salt thereof, wherein each $R^{4A}$ is independently selected from chloro, fluoro, methyl, hydroxy, methoxy, cyano, C(O)OH, morpholinyl, piperazinyl, cyclopropyl, phenyl, pyrazolyl, $C(O)NH_2$, $C(O)N(CH_3)_2$, $C(O)NH_2$-(cyclopropylmethyl), $C(O)NHCH_2CH_3$, $C(O)NHCH_2CH_2OH$, $NHC(O)CH_3$, $SO_2CH_3$, $SO_2CH_2CH_3$, $SO_2NHCH_3$, $SO_2N(CH_3)_2$, $SO_2$-isopropyl, $SO_2$-cyclopropyl, and $SO_2$-morpholinyl, wherein the methyl, morpholinyl, piperazinyl, cyclopropyl, phenyl, pyrazolyl, $C(O)NH_2$-(cyclopropylmethyl), $SO_2$-isopropyl, $SO_2$-cyclopropyl, and $SO_2$-morpholinyl of $R^{4A}$ are each optionally substituted with 1 or 2 substituents independently selected from methyl, hydroxy, cyano, dimethylamino, $C(O)CH_3$, $NHC(O)CH_3$, $C(O)NHCH_3$, and $CH(CH_3)C(O)NH_2$.

32. The compound of claim 1, or a pharmaceutically acceptable salt thereof, wherein $R^5$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^{5A}$ substituents.

33. The compound of claim 1, or a pharmaceutically acceptable salt thereof, wherein $R^5$ is selected from H, halo, phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents.

34. The compound of claim 1, or a pharmaceutically acceptable salt thereof, wherein $R^5$ is selected from H, halo, and phenyl which is optionally substituted by 1 or 2 independently selected $R^{5A}$ substituents.

35. The compound of claim 1, or a pharmaceutically acceptable salt thereof, wherein each $R^{5A}$ is independently selected from $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{5A}$ are each optionally substituted with 1, 2, 3, or 4 independently selected $R^{5B}$ substituents.

36. The compound of claim 1, or a pharmaceutically acceptable salt thereof, wherein each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1, 2, 3, or 4 independently selected $R^{5B}$ substituents.

37. The compound of claim 1, or a pharmaceutically acceptable salt thereof, wherein each $R^{5A}$ is piperidinylmethyl, which is optionally substituted by 1 or 2 independently selected $R^{5B}$ groups.

38. The compound of claim 1, or a pharmaceutically acceptable salt thereof, wherein each $R^{5B}$ is independently selected from $C(O)R^{b52}$, $C(O)NR^{c52}R^{d52}$, $C(O)OR^{a22}$, $NR^{c52}S(O)R^{b52}$, $R^{c52}S(O)_2R^{b52}$, $S(O)R^{b52}$, $S(O)NR^{c52}R^{d52}$, $S(O)_2R^{b52}$, and $S(O)_2NR^{c52}R^{d52}$.

39. The compound of claim 1, or a pharmaceutically acceptable salt thereof, wherein each $R^{a52}$, $R^{b52}$, $R^{c52}$, and $R^{d52}$ is independently selected from H and $C_{1-6}$ alkyl.

40. The compound of claim 1, or a pharmaceutically acceptable salt thereof, wherein each $R^{5B}$ is $S(O)_2R^{52}$, wherein each $R^{b52}$ is independently selected from H and $C_{1-6}$ alkyl.

41. The compound of claim 1, or a pharmaceutically acceptable salt thereof, wherein each $R^{5B}$ is methylsulfonyl.

42. The compound of claim 1, or a pharmaceutically acceptable salt thereof, wherein $R^5$ is selected from H, bromo, and phenyl which is optionally substituted by piperidinylmethyl, wherein the piperidinylmethyl is optionally substituted by methylsulfonyl.

43. The compound of claim 1, or a pharmaceutically acceptable salt thereof, wherein:

$R^1$ is selected from H, $C_{1-6}$ alkyl, $C_{1-6}$ haloalkyl, $C_{2-6}$ alkenyl, and $C_{2-6}$ alkynyl;

$R^2$ is selected from H, $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl-, wherein the $C_{1-6}$ alkyl, $C_{6-10}$ aryl, $C_{3-10}$ cycloalkyl, 4-10 membered heterocycloalkyl, $C_{6-10}$ aryl-$C_{1-6}$ alkyl-, and (5-10 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, $C(O)R^{b21}$, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, $S(O)R^{b21}$, $S(O)NR^{c21}R^{d21}$, $S(O)_2R^{b21}$, and $S(O)_2NR^{c21}R^{d21}$ wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$ and $R^{d21}$ are each independently selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$ wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H, $C_{1-6}$ alkyl, $C_{1-6}$ haloalkyl, $C_{2-6}$ alkenyl, and $C_{2-6}$ alkynyl;

$R^{3'}$ is selected from H, $C_{1-6}$ alkyl, $C_{1-6}$ haloalkyl, $C_{2-6}$ alkenyl, and $C_{2-6}$ alkynyl;

$R^4$ is selected from H, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a4}$, and $C(O)OR^{a4}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, NO$_2$, OR$^{a41}$, C(O)R$^{b41}$, C(O)NR$^{c41}$R$^{d41}$, NR$^{c41}$R$^{d41}$, NR$^{c41}$C(O)R$^{b41}$, NR$^{c41}$S(O)R$^{b41}$, NR$^{c41}$S(O)$_2$R$^{b41}$, S(O)R$^{b41}$, S(O)NR$^{c41}$R$^{d41}$, S(O)$_2$R$^{b41}$, and S(O)$_2$NR$^{c41}$R$^{d41}$, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl, of R$^{4A}$ are each optionally substituted with 1, 2, 3, or 4 independently selected R$^{4B}$ substituents;

each R$^{a41}$, R$^{c41}$, and R$^{d41}$ is independently selected from H, C$_{1-6}$ alkyl, C$_{1-6}$ haloalkyl, C$_{2-6}$ alkenyl, C$_{2-6}$ alkynyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, C$_{2-6}$ alkenyl, C$_{2-6}$ alkynyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a41}$, R$^{c41}$ and R$^{d41}$ are each optionally substituted with 1, 2, 3, or 4 independently selected R$^{4B}$ substituents;

or, any R$^{c41}$ and R$^{d41}$ attached to the same N atom, together with the N atom to which they are attached, form a 5-10 membered heteroaryl or a 4-10 membered heterocycloalkyl group, wherein the 5-10 membered heteroaryl or 4-10 membered heterocycloalkyl group is optionally substituted with 1, 2, 3, or 4 independently selected R$^{4B}$ substituents;

each R$^{b41}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl of R$^{b41}$ are each optionally substituted with 1, 2, 3, or 4 independently selected R$^{4B}$ substituents;

each R$^{4B}$ is independently selected from halo, C$_{1-6}$ alkyl, C$_{1-6}$ haloalkyl, C$_{2-6}$ alkenyl, C$_{2-6}$ alkynyl, CN, NO$_2$, OR$^{a42}$, SR$^{a42}$, C(O)R$^{b42}$, C(O)NR$^{c42}$R$^{d42}$, C(O)OR$^{a42}$, OC(O)R$^{b42}$, OC(O)NR$^{c42}$R$^{d42}$, NR$^{c42}$R$^{d42}$, NR$^{c42}$C(O)R$^{b42}$, and NR$^{c42}$C(O)OR$^{a42}$, wherein the C$_{1-6}$ alkyl, C$_{2-6}$ alkenyl, and C$_{2-6}$ alkynyl of R$^{4B}$ are each optionally substituted with 1, 2, 3, or 4 independently selected R$^{4C}$ substituents;

each R$^{a42}$, R$^{c42}$, and R$^{d42}$ is independently selected from H, C$_{1-6}$ alkyl, C$_{1-6}$ haloalkyl, C$_{2-6}$ alkenyl, and C$_{2-6}$ alkynyl;

each R$^{b42}$ is independently selected from H, C$_{1-6}$ alkyl, C$_{1-6}$ haloalkyl, C$_{2-6}$ alkenyl, and C$_{2-6}$ alkynyl;

each R$^{4C}$ is independently selected from halo, C$_{1-6}$ alkyl, C$_{1-6}$ haloalkyl, C$_{2-6}$ alkenyl, C$_{2-6}$ alkynyl, CN, NO$_2$, OR$^{a43}$, C(O)R$^{b43}$, C(O)NR$^{c43}$R$^{d43}$, and C(O)OR$^{a43}$;

each R$^{a43}$, R$^{b43}$, R$^{c43}$, and R$^{d43}$ is independently selected from H and C$_{1-6}$ alkyl;

R$^5$ is selected from H, halo, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^5$ are each optionally substituted with 1, 2, 3, or 4 independently selected R$^{5A}$ substituents;

each R$^{5A}$ is independently selected from C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{5A}$ are each optionally substituted with 1, 2, 3, or 4 independently selected R$^{5B}$ substituents;

each R$^{5B}$ is independently selected from C(O)R$^{b22}$, C(O)NR$^{c52}$R$^{d52}$, C(O)OR$^{a52}$, NR$^{c52}$S(O)R$^{b52}$, NR$^{c52}$S(O)$_2$R$^{b52}$, S(O)R$^{b52}$, S(O)NR$^{c52}$R$^{d52}$, S(O)$^2$R$^{b52}$, and S(O)$^2$NR$^{c52}$R$^{d52}$, and each R$^{a52}$, R$^{b52}$, R$^{c52}$, and R$^{d52}$ is independently selected from H and C$_{1-6}$ alkyl.

44. The compound of claim 1, or a pharmaceutically acceptable salt thereof, wherein:

R$^1$ is selected from H and C$_{1-6}$ alkyl;

R$^2$ is selected from H, C$_{1-6}$ alkyl, phenyl, C$_{3-6}$ cycloalkyl, 4-6 membered heterocycloalkyl, phenyl-C$_{1-6}$ alkyl-, and (5-6 membered heteroaryl)-C$_{1-6}$ alkyl-, wherein the C$_{1-6}$ alkyl, phenyl, C$_{3-6}$ cycloalkyl, 4-6 membered heterocycloalkyl, phenyl-C$_{1-6}$ alkyl, and (5-6 membered heteroaryl)-C$_{1-6}$ alkyl- of R$^2$ are each optionally substituted with 1, 2, 3, or 4 independently selected R$^{2A}$ substituents;

each R$^{2A}$ is independently selected from halo, C$_{1-6}$ alkyl, 5-6 membered heteroaryl, 4-6 membered heterocycloalkyl, (4-6 membered heterocycloalkyl)-C$_{1-6}$ alkyl-, C(O)NR$^{c21}$R$^{d21}$, C(O)NR$^{c21}$(OR$^{a21}$), C(O)OR$^{a21}$, NR$^{c21}$R$^{d21}$, NR$^{c21}$C(O)R$^{b21}$, and S(O)$_2$NR$^{c21}$R$^{d21}$, wherein the C$_{1-6}$ alkyl, 5-6 membered heteroaryl, 4-6 membered heterocycloalkyl, and (4-6 membered heterocycloalkyl)-C$_{1-6}$ alkyl- of R$^{2A}$ are each optionally substituted with 1, 2, 3, or 4 independently selected R$^{2B}$ substituents;

R$^{a21}$, R$^{b21}$, R$^{c21}$, and R$^{d21}$ are each independently selected from H, C$_{1-6}$ alkyl, phenyl, C$_{3-6}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl-, wherein the C$_{1-6}$ alkyl, phenyl, C$_{3-6}$ cycloalkyl, 5-10 membered heteroaryl, 4-10 membered heterocycloalkyl, C$_{6-10}$ aryl-C$_{1-6}$ alkyl-, C$_{3-10}$ cycloalkyl-C$_{1-6}$ alkyl-, (5-10 membered heteroaryl)-C$_{1-6}$ alkyl-, and (4-10 membered heterocycloalkyl)-C$_{1-6}$ alkyl- of R$^{a21}$, R$^{b21}$, R$^{c21}$, and R$^{d21}$ are each optionally substituted with 1, 2, 3, or 4 independently selected R$^{2B}$ substituents;

each R$^{2B}$ is independently selected from halo, C$_{1-6}$ alkyl, CN, OR$^{a22}$, C(O)OR$^{a22}$, NR$^{c22}$R$^{d22}$, wherein the C$_{1-6}$ alkyl is optionally substituted with 1 or 2 R$^{2C}$ substituents independently selected from OH and CN;

each R$^{a22}$, R$^{c22}$, and R$^{d22}$ is independently selected from H and C$_{1-6}$ alkyl;

R$^3$ is selected from H and C$_{1-6}$ alkyl;

R$^{3'}$ is selected from H and C$_{1-6}$ alkyl;

R$^4$ is selected from H, halo, C$_{1-6}$ alkyl, C$_{2-6}$ alkenyl, phenyl, C$_{3-6}$ cycloalkyl, 5-6 membered heteroaryl, 4-6 membered heterocycloalkyl, CN, and C(O)OR$^{a4}$, wherein the C$_{1-6}$ alkyl, C$_{2-6}$ alkenyl, phenyl, C$_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from halo, $C_{1-6}$ alkyl, phenyl, $C_{3-6}$ cycloalkyl, 5-6 membered heteroaryl, 4-6 membered heterocycloalkyl, CN, $OR^{a41}$, $C(O)R^{b41}$, $C(O)NR^{c41}R^{d41}$, $NR^{c41}C(O)R^{b41}$, $S(O)_2R^{b41}$, and $S(O)_2NR^{c41}R^{d41}$ wherein the $C_{1-6}$ alkyl, phenyl, $C_{3-6}$ cycloalkyl, 5-6 membered heteroaryl, and 4-6 membered heterocycloalkyl, of $R^{4A}$ are each optionally substituted with 1, 2, 3, or 4 independently selected $R^{4B}$ substituents;

each $R^{4B}$ is independently selected from $C_{1-6}$ alkyl, CN, $OR^{a42}$, $C(O)R^{b42}$, $C(O)NR^{c42}R^{d42}$, $NR^{c42}R^{d42}$, and $NR^{c42}C(O)R^{b42}$, wherein the $C_{1-6}$ alkyl of $R^{4B}$ is optionally substituted with 1 or 2 independently selected $R^{4C}$ substituents;

each $R^{a42}$, $R^{b42}$, $R^{c42}$, and $R^{d42}$ is independently selected from H and $C_{1-6}$ alkyl;

each $R^{4C}$ is an independently selected $C(O)NR^{c43}R^{d43}$ substituent;

each $R^{c43}$ and $R^{d43}$ is independently selected from H and $C_{1-6}$ alkyl, $R^5$ is selected from H, halo, phenyl, $C_{3-6}$ cycloalkyl, 5-6 membered heteroaryl, and 4-6 membered heterocycloalkyl, wherein the phenyl, $C_{3-6}$ cycloalkyl, 5-6 membered heteroaryl, and 4-6 membered heterocycloalkyl of $R^5$ are each optionally substituted with 1, 2, 3, or 4 independently selected $R^{5A}$ substituents;

each $R^{5A}$ is independently selected from phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl-, wherein the phenyl-$C_{1-6}$ alkyl-, $C_{3-6}$ cycloalkyl-$C_{1-6}$ alkyl-, (5-6 membered heteroaryl)-$C_{1-6}$ alkyl-, and (4-6 membered heterocycloalkyl)-$C_{1-6}$ alkyl- of $R^{5A}$ are each optionally substituted with 1 or 2 independently selected $R^{5B}$ substituents;

each $R^{5B}$ is $S(O)_2R^{b52}$; and each $R^{b52}$ is independently selected from H and $C_{1-6}$ alkyl.

45. The compound of claim 1, or a pharmaceutically acceptable salt thereof, wherein:

$R^1$ is selected from H and $C_{1-6}$ alkyl;

$R^2$ is selected from H, $C_{1-6}$ alkyl, phenyl, $C_{3-6}$ cycloalkyl, 4-6 membered heterocycloalkyl, phenyl-$C_{1-6}$ alkyl-, and (5-6 membered heteroaryl)-$C_{1-6}$ alkyl-, wherein the $C_{1-6}$ alkyl, phenyl, $C_{3-6}$ cycloalkyl, 4-6 membered heterocycloalkyl, phenyl-$C_{1-6}$ alkyl, and (5-6 membered heteroaryl)-$C_{1-6}$ alkyl- of $R^2$ are each optionally substituted with 1, 2, 3, or 4 independently selected $R^{2A}$ substituents;

each $R^{2A}$ is independently selected from halo, $C_{1-6}$ alkyl, 5-6 membered heteroaryl, 4-6 membered heterocycloalkyl, (4-6 membered heterocycloalkyl)-$C_{1-6}$ alkyl-, $C(O)NR^{c21}R^{d21}$, $C(O)NR^{c21}(OR^{a21})$, $C(O)OR^{a21}$, $NR^{c21}R^{d21}$, $NR^{c21}C(O)R^{b21}$, and $S(O)_2NR^{c21}R^{d21}$, wherein the $C_{1-6}$ alkyl, 5-6 membered heteroaryl, 4-6 membered heterocycloalkyl, and (4-6 membered heterocycloalkyl)-$C_{1-6}$ alkyl- of $R^{2A}$ are each optionally substituted with 1, 2, 3, or 4 independently selected $R^{2B}$ substituents;

$R^{a21}$, $R^{b21}$, $R^{c21}$, and $R^{d21}$ are each independently selected from H, $C_{1-6}$ alkyl, phenyl, $C_{3-6}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a21}$, $R^{b21}$, $R^{c21}$, and $R^{d21}$ are each optionally substituted with 1, 2, 3, or 4 independently selected $R^{2B}$ substituents;

each $R^{2B}$ is independently selected from halo, $C_{1-6}$ alkyl, CN, $OR^{a22}$, $C(O)OR^{a22}$, $NR^{c22}R^{d22}$, wherein the $C_{1-6}$ alkyl is optionally substituted with 1 or 2 $R^{2C}$ substituents independently selected from OH and CN;

each $R^{a22}$, $R^{c22}$, and $R^{d22}$ is independently selected from H and $C_{1-6}$ alkyl;

$R^3$ is selected from H and $C_{1-6}$ alkyl;

$R^{3'}$ is H;

$R^4$ is selected from H, halo, $C_{1-6}$ alkyl, $C_{2-6}$ alkenyl, phenyl, $C_{3-6}$ cycloalkyl, 5-6 membered heteroaryl, 4-6 membered heterocycloalkyl, CN, and $C(O)OR^{a4}$, wherein the $C_{1-6}$ alkyl, $C_{2-6}$ alkenyl, phenyl, $C_{3-6}$ cycloalkyl, 5-6 membered heteroaryl, and 4-6 membered heterocycloalkyl of $R^4$ are each optionally substituted with 1, 2, 3, or 4 independently selected $R^{4A}$ substituents;

each $R^{a4}$ is independently selected from H and $C_{1-6}$ alkyl;

each $R^{4A}$ is independently selected from chloro, fluoro, methyl, hydroxy, methoxy, cyano, $C(O)OH$, morpholinyl, piperazinyl, cyclopropyl, phenyl, pyrazolyl, $C(O)NH_2$, $C(O)N(CH_3)_2$, $C(O)NH_2$-(cyclopropylmethyl), $C(O)NHCH_2CH_3$, $C(O)NHCH_2CH_2OH$, $NHC(O)CH_3$, $SO_2CH_3$, $SO_2CH_2CH_3$, $SO_2NHCH_3$, $SO_2N(CH_3)_2$, $SO_2$-isopropyl, $SO_2$-cyclopropyl, and $SO_2$-morpholinyl, wherein the methyl, morpholinyl, piperazinyl, cyclopropyl, phenyl, pyrazolyl, $C(O)NH_2$-(cyclopropylmethyl), $SO_2$-isopropyl, $SO_2$-cyclopropyl, and $SO_2$-morpholinyl of $R^{4A}$ are each optionally substituted with 1 or 2 substituents independently selected from methyl, hydroxy, cyano, dimethylamino, $C(O)CH_3$, $NHC(O)CH_3$, $C(O)NHCH_3$, and $CH(CH_3)C(O)NH_2$;

$R^5$ is selected from H, halo, and phenyl which is optionally substituted by 1 or 2 independently selected $R^{5A}$ substituents;

each $R^{5A}$ is piperidinylmethyl, which is optionally substituted by 1 or 2 independently selected $R^{5B}$ groups;

each $R^{5B}$ is $S(O)_2R^{b52}$; and each $R^{b52}$ is independently selected from H and $C_{1-6}$ alkyl.

46. The compound of claim 1, wherein the compound of Formula I is a compound of Formula II:

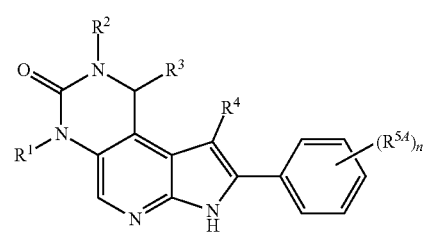

or a pharmaceutically acceptable salt thereof, wherein n is 0, 1, 2, 3, or 4.

47. The compound of claim 1, wherein the compound of Formula I is a compound of Formula III:

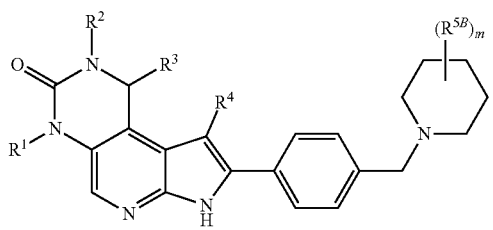

III or a pharmaceutically acceptable salt thereof, wherein m is 0, 1, 2, 3, or 4.

48. The compound of claim 1, wherein the compound of Formula I is a compound of Formula IV:

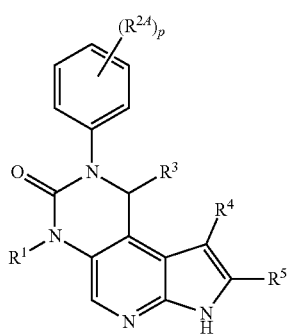

IV or a pharmaceutically acceptable salt thereof, wherein p is 0, 1, 2, 3, or 4.

49. The compound of claim 1, wherein the compound of Formula I is a compound of Formula V:

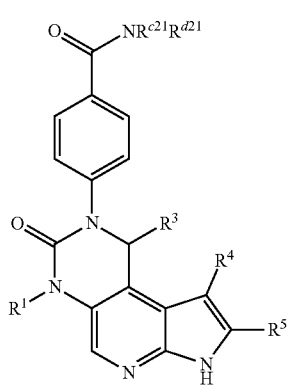

V or a pharmaceutically acceptable salt thereof.

50. The compound of claim 1, wherein the compound of Formula I is a compound of Formula VI:

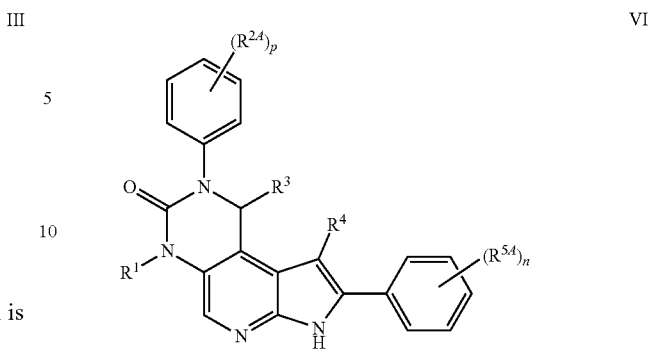

VI or a pharmaceutically acceptable salt thereof, wherein:
n is 0, 1, 2, 3, or 4; and
p is 0, 1, 2, 3, or 4.

51. The compound of claim 1, wherein the compound of Formula I is a compound of Formula VII:

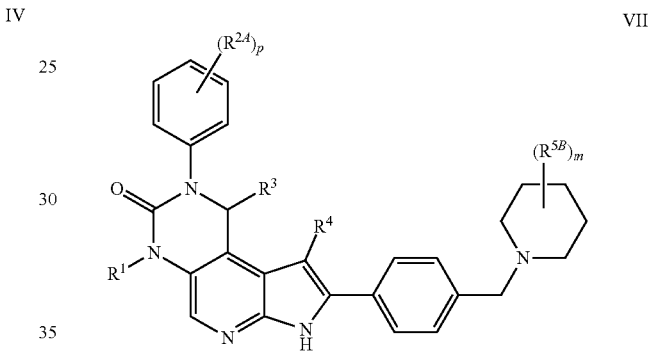

VII or a pharmaceutically acceptable salt thereof, wherein:
m is 0, 1, 2, 3, or 4; and
p is 0, 1, 2, 3, or 4.

52. The compound of claim 1, which is selected from:
4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;
4-methyl-8-(4-((4-(methylsulfonyl)piperidin-1-yl)methyl)phenyl)-2-phenyl-1,2,4,7-tetrahydro-3H-pyrrolo[3',2':5,6]pyrido[3,4-d]pyrimidin-3-one;
4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;
8-(4-((4-(methylsulfonyl)piperidin-1-yl)methyl)phenyl)-2-(pyridin-3-ylmethyl)-1,2,4,7-tetrahydro-3H-pyrrolo[3',2':5,6]pyrido[3,4-d]pyrimidin-3-one;
2-cyclohexyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;
4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)cyclohexane-1-carboxylic acid;
4-(8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)piperidine-1-sulfonamide;
2-(4-((2-methoxyethyl)amino)phenyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;

2-cyano-N-(4-(4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)phenyl)acetamide;

4-(1,4-dimethyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-(pyridin-3-yl)benzamide;

4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)-N-methylbenzamide;

N-(2-(2-benzylhydrazineyl)-2-oxoethyl)-4-(9-(4-methoxyphenyl)-4-methyl-8-(4-((4-(methylsulfonyl)piperidin-1-yl)methyl)phenyl)-3-oxo-1,3,4,7-tetrahydro-2H-pyrrolo[3',2': 5,6]pyrido[3,4-d]pyrimidin-2-yl)benzamide;

4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-((1-cyanocyclopropyl)methyl)benzamide;

4-(9-(methoxycarbonyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

N-(4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)benzyl)acetamide;

4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)-N-methylbenzenesulfonamide;

9-(4-(4-acetylpiperazin-1-yl)phenyl)-2-(tert-butyl)-4-methyl-8-(4-((4-(methylsulfonyl)piperidin-1-yl)methyl)phenyl)-1,2,4,7-tetrahydro-3H-pyrrolo[3',2':5,6]pyrido[3,4-d]pyrimidin-3-one;

2-(4-(4-(2-(tert-butyl)-4-methyl-8-(4-((4-(methylsulfonyl)piperidin-1-yl)methyl)phenyl)-3-oxo-2,3,4,7-tetrahydro-1H-pyrrolo[3',2':5,6]pyrido[3,4-d]pyrimidin-9-yl)phenyl)-1H-pyrazol-1-yl)propanamide;

4-(9-(1-acetyl-1,2,3,6-tetrahydropyridin-4-yl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-(4-(1-aminocyclopropyl)phenyl)-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(4-methyl-9-(1-methyl-1H-pyrrol-3-yl)-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-cyclopropyl-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

4-(9-cyano-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid; and 4-(9-iodo-4-methyl-8-(4-((4-(methylsulfonyl)piperidin-1-yl)methyl)phenyl)-3-oxo-1,3,4,7-tetrahydro-2H-pyrrolo[3',2':5,6]pyrido[3,4-d]pyrimidin-2-yl)benzoic acid;

or a pharmaceutically acceptable salt thereof.

53. The compound of claim 1, which is 4-(8-cyclopropyl-9-(4-methoxyphenyl)-4-methyl-3-oxo-1,3,4,7-tetrahydro-2H-pyrrolo[3',2':5,6]pyrido[3,4-d]pyrimidin-2-yl)benzoic acid, or a pharmaceutically acceptable salt thereof.

54. The compound of claim 1, or a pharmaceutically acceptable salt thereof, wherein the compound is deuterated.

55. A pharmaceutical composition, comprising a compound of claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

Page 1 of 2

PATENT NO. : 11,661,422 B2
APPLICATION NO. : 17/412650
DATED : May 30, 2023
INVENTOR(S) : Kai Liu et al.

It is certified that error appears in the above-identified patent and that said Letters Patent is hereby corrected as shown below:

In the Claims

Column 172, Line 43, Claim 1, before "halo," delete "D,";

Column 173, Line 43, Claim 1, before "halo," delete "D,";

Column 174, Line 41, Claim 1, before "halo," delete "D,";

Column 175, Line 46, Claim 1, before "halo," delete "D,";

Column 176, Line 46, Claim 1, before "halo," delete "D,";

Column 177, Line 47, Claim 1, before "halo," delete "D,";

Column 178, Line 44, Claim 1, before "halo," delete "D,";

Column 179, Line 41, Claim 1, before "halo," delete "D,";

Column 180, Line 41, Claim 1, before "halo," delete "D,";

Column 180, Line 50, Claim 1, delete "$NR^{c42}NR^{c42}R^{d42}$" and insert -- $NR^{c42}NR^{c42}R^{d42}$, --;

Column 181, Line 41, Claim 1, before "halo," delete "D,";

Column 182, Line 38, Claim 1, before "halo," delete "D,";

Column 183, Line 35, Claim 1, before "halo," delete "D,";

Column 184, Line 35, Claim 1, before "halo," delete "D,";

Signed and Sealed this
Twenty-first Day of May, 2024

Katherine Kelly Vidal
*Director of the United States Patent and Trademark Office*

CERTIFICATE OF CORRECTION (continued)
U.S. Pat. No. 11,661,422 B2

Column 185, Line 35, Claim 1, before "halo," delete "D,";

Column 186, Line 33, Claim 1, before "halo," delete "D,";

Column 186, Line 35, Claim 1, delete "$C_{1-6}$alkoxy, $C_{1-6}$haloalkoxy, $C_{1-6}$haloalkyl," and insert -- $C_{1-6}$ alkoxy, $C_{1-6}$ haloalkoxy, $C_{1-6}$ haloalkyl, --;

Column 187, Line 31, Claim 9, delete "$C(O)NR^{c21}R^{a21}$," and insert -- $C(O)NR^{c21}R^{d21}$, --;

Column 189, Line 47, Claim 25, delete "$C(O)NR^{c41}R^{d4}1$," and insert -- $C(O)NR^{c41}R^{d41}$, --;

Column 190, Line 30, Claim 28, delete "$NR^{c42}R^{d42}$" and insert -- $NR^{c42}R^{d42}$, --;

Column 191, Line 47, Claim 38, delete "$C(O)OR^{a22}$" and insert -- $C(O)OR^{a52}$, --;

Column 191, Line 48, Claim 38, delete "$R^{c52}S(O)_2R^{b52}$," and insert -- $NR^{c52}S(O)_2R^{b52}$, --;

Column 191, Line 54, Claim 40, delete "$S(O)_2R^{52}$," and insert -- $S(O)_2R^{b52}$, --;

Column 192, Lines 17-18, Claim 43, delete "$S(O)_2NR^{c21}R^{a21}$" and insert -- $S(O)_2NR^{c21}R^{d21}$, --;

Column 192, Line 26, Claim 43, delete "$R^{c21}$" and insert -- $R^{c21}$, --;

Column 192, Line 41, Claim 43, delete "$NR^{c22}R^{d22}$" and insert -- $NR^{c22}R^{d22}$, --;

Column 194, Line 14, Claim 43, delete "$C(O)R^{b22}$," and insert -- $C(O)R^{b52}$, --;

Column 194, Line 16, Claim 43, delete "$S(O)^2R^{b52}$," and insert -- $S(O)_2R^{b52}$, --;

Column 194, Lines 16-17, Claim 43, delete "$S(O)^2NR^{c52}R^{d52}$," and insert -- $S(O)_2NR^{c52}R^{d52}$; --;

Column 194, Line 27, Claim 44, delete "alkyl," and insert -- alkyl-, --;

Column 195, Line 9, Claim 44, delete "$S(O)_2NR^{c41}R^{d41}$" and insert -- $S(O)_2NR^{c41}R^{d41}$, --;

Column 195, Line 24, Claim 44, delete "alkyl," and insert -- alkyl; --;

Column 195, Line 48, Claim 45, delete "alkyl," and insert -- alkyl-, --;

Column 199, Line 19, Claim 52, delete "[3',2': 5,6]" and insert -- [3',2':5,6] --.